United States Patent [19]

Arisawa et al.

[11] Patent Number: 5,486,466
[45] Date of Patent: Jan. 23, 1996

[54] PROCESS FOR THE PREPARATION OF DNA GYRASE INHIBITORS

[75] Inventors: Mikio Arisawa, Kamakura, Japan; Erwin Götschi; Paul Hebeisen, both of Reinach, Switzerland; Tsutomu Kamiyama, Yokohama, Japan; Helmut Link; Raffaello Masciadri, both of Basel, Switzerland; Hisao Shimada, Fujisawa; Junko Watanabe, Yokohama, both of Japan

[73] Assignee: Hoffmann-La Roche Inc., Nutley, N.J.

[21] Appl. No.: 339,442

[22] Filed: Nov. 14, 1994

Related U.S. Application Data

[62] Division of Ser. No. 177,483, Jan. 6, 1994, Pat. No. 5,399,741, which is a division of Ser. No. 952,537, Dec. 9, 1992, Pat. No. 5,294,609, filed as PCT/EP92/00809, filed on Apr. 9, 1992.

[30] Foreign Application Priority Data

Apr. 17, 1991 [EP] European Pat. Off. .............. 91106105

[51] Int. Cl.$^6$ .............................. C12P 13/04; C12N 1/20
[52] U.S. Cl. ...................... 435/106; 435/253.5; 435/886; 514/10; 514/183; 514/431
[58] Field of Search ............................. 435/106, 253.5, 435/886; 514/183, 431, 10, 183

[56] References Cited

U.S. PATENT DOCUMENTS

| | | |
|---|---|---|
| 3,239,350 | 3/1966 | Hodge et al. . |
| 3,678,159 | 7/1972 | Niida et al. ............................. 435/886 |
| 4,175,007 | 11/1979 | Zimmerman et al. .................. 435/105 |
| 4,332,891 | 6/1982 | Kamogashira ......................... 435/886 |
| 4,534,970 | 8/1985 | Labeda et al. ......................... 435/169 |
| 5,266,484 | 11/1993 | Inoue et al. ........................... 435/253.5 |
| 5,294,609 | 3/1994 | Arisawa et al. ....................... 514/183 |

*Primary Examiner*—Herbert J. Lilling
*Attorney, Agent, or Firm*—George M. Gould; George W. Johnston; Alan P. Kass

[57] ABSTRACT

Bicyclic derivatives of the general formula

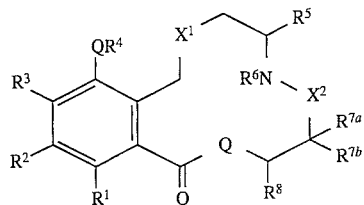

wherein $X^1$ is —S— or —SO—;

$X^2$ is —CO— or —CS—;

$R^1$ is hydrogen, halogen or lower alkyl optionally substituted by halogen or lower alkoxy;

$R^2$ and $R^3$ are each independently hydrogen, lower alkyl, halogen, amino, lower alkylamino, di-lower alkylamino, acylamino, lower alkexy, lower alkoxymethoxy or a group $OR^4$;

$R^4$ is hydrogen or an easily hydrolyzable group;

$R^5$ is hydrogen, optionally esterified carboxy or amidated (thio)carboxy, optionally substituted alkyl, optionally substituted alkenyl, optionally substituted acyl or heterocyclyl;

$R^6$ and $R^{7a}$ are each independently hydrogen or lower alkyl;

$R^{7b}$ is hydrogen, optionally substituted hydroxy, —NR—A or —N=B, in which R is hydrogen or lower alkyl, A is hydrogen, optionally substituted alkyl, lower cycloalkyl, iminoyl, (thio)acyl, esterified carboxy or amidated (thio)carboxy and B is lower alkylidene;

$R^{7a}$ and $R^{7b}$ together represent oxo, lower alkoxycarbonylmethylidene or optionally substituted hydroxyimino; and $R^8$ is hydrogen, optionally substituted alkyl, optionally esterified carboxy or amidated (thio)carboxy; provided that no more than two of $R^1$–$R^3$ are nitrogen-containing groups; no more than two of $R^1$–$R^3$ are oxygen containing groups and no more than two of $R^1$–$R^3$ are either nitrogen containing or oxygen containing groups;

and pharmaceutically acceptable salts of the compounds of formula I carrying an acidic and/or basic substituent.

The products are antimicrobially active.

2 Claims, No Drawings

PROCESS FOR THE PREPARATION OF DNA GYRASE INHIBITORS

This is a division of application Ser. No. 08/177,483, filed Jan. 6, 1994, now U.S. Pat. No. 5,399,741 which is a division of application Ser. No. 07/952,537, filed Dec. 9, 1992, now U.S. Pat. No. 5,294,609, filed as International Application PCT/EP92/00809, filed on Apr. 9, 1992 and which designated in the U.S.

The invention relates to novel DNA gyrase inhibitors, which are bicyclic derivatives of the general formula

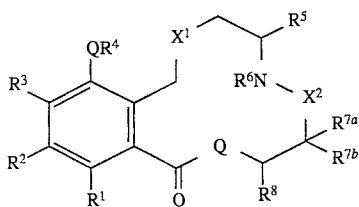

wherein $X^1$ is —S— or —SO—;

$X^2$ is —CO— or —CS—;

$R^1$ is hydrogen, halogen or lower alkyl optionally substituted by halogen or lower alkoxy;

$R^2$ and $R^3$ are each independently hydrogen, lower alkyl, halogen, amino, lower alkylamino, di-lower alkylamino, acylamino, lower alkoxy, lower alkoxymethoxy or a group $OR^4$;

$R^4$ is hydrogen or an easily hydrolyzable group;

$R^5$ is hydrogen, optionally esterified carboxy or amidated (thio)carboxy, optionally substituted alkyl, optionally substituted alkenyl, optionally substituted acyl or heterocyclyl;

$R^6$ and $R^{7a}$ are each independently hydrogen or lower alkyl;

$R^{7b}$ is hydrogen, optionally substituted hydroxy, —NR—A or —N=B, in which R is hydrogen or lower alkyl, A is hydrogen, optionally substituted alkyl, lower cycloalkyl, iminoyl, (thio)acyl, esterified carboxy or amidated (thio)carboxy and B is lower alkylidene;

$R^{7a}$ and $R^{7b}$ together represent oxo, lower alkoxycarbonylmethylidene or optionally substituted hydroxyimino; and $R^8$ is hydrogen, optionally substituted alkyl, optionally esterified carboxy or amidated (thio)carboxy; provided that no more than two of $R^1$–$R^3$ are nitrogen-containing groups; no more than two of $R^1$–$R^3$ are oxygen containing groups and no more than two of $R^1$–$R^3$ are either nitrogen containing or oxygen containing groups;

and pharmaceutically acceptable salts of the compounds of formula I carrying an acidic and/or basic substituent.

Hereinabove and in the following, reference to the word "lower" such as in "lower alkyl", "lower alkoxy", "lower alkanoyl" etc. refers to hydrocarbon groups containing up to and including 6, preferably 1–2, carbon atoms unless otherwise specified. Thus, e.g. "lower alkyl" in the following, alone or in combination with other groups such as in "lower alkylamino", "di-lower alkylamino", "aryl-lower alkyl" etc. is e.g. methyl, ethyl, t-butyl, n-pentyl etc.; "lower alkoxy" has analogous meanings; "lower alkenyl" alone or in combination with other groups such as "lower cycloalkyl-lower alkenyl", "heterocyclyl-lower alkenyl" etc. is e.g. vinyl, 1- or 2-propenyl; "lower cycloalkyl" alone or in combination with other groups such as "lower cycloalkyl-lower alkenyl", "lower cycloalkyl-lower alkyl" etc. is e.g. cyclopropyl, cyclobutyl, cyclohexyl; "lower alkynyl" alone or in combination with other groups such as "lower cycloalkyl-lower alkynyl" is e.g. ethynyl, 1- or 2-propynyl; "lower alkanoyl" alone or in combination with other groups such as "lower alkanoyloxy" etc. is e.g. formyl, acetyl, propionyl, isobutyryl, pivaloyl etc.

Groups not specified by the word "lower", such as "alkyl", "alkoxy", "alkenyl", "acyl" and "alkanoyl", are intended to refer to groups containing up to and including 14 carbon atoms unless otherwise specified.

"(Thio)acyl" refers to an acyl group or a thioacyl group.

"Acyl" alone or in combination with other groups such as in "acylamino", is preferably derived from a carboxylic acid and is thus e.g. lower alkanoyl, e.g. formyl, acetyl, propionyl, isobutyryl, pivaloyl; lower alkenoyl, e.g. crotonoyl, isocrotonoyl; lower cycloalkanoyl, e.g. cyclopropylcarbonyl; aroyl, e.g. benzoyl, o-carboxy-benzoyl, p-toluoyl, p-anisoyl, naphthoyl; heterocyclylcarbonyl, e.g. furoyl, thenoyl. "Thioacyl" has analogous meanings.

"Halogen" alone or in combination with other groups such as in "halogen-lower alkyl" etc. refers to all four halogens, i.e. chlorine, bromine, iodine, fluorine, unless otherwise indicated.

The expressions "lower alkenylalkyl" and "lower alkynylalkyl" are employed to indicate that the double and triple bonds of these groups are not connected with the first carbon atom (such as in vinyl, ethynyl and 1-propynyl), but that these groups are limited to the less reactive groups having their unsaturation in 2-, 3- and further positions. It is understood that "lower alkenylalkyl" and "lower alkynylalkyl" refer to groups containing up to and including 5 carbon atoms, e.g. 2-propenyl, 2-butenyl, 3-butenyl, 2-methyl-2-propenyl, 2-propynyl, 2-butynyl, 3-butynyl, 2-methyl-2-propynyl.

Easily hydrolyzable groups —$OR^4$ are e.g. lower alkanoyloxy groups such as formyloxy, acetoxy, propionyloxy, isobutyryloxy, pivaloyloxy or lower alkoxycarbonyloxy groups such as methoxycarbonyloxy or ethoxycarbonyloxy.

The above definition of $R^1$–$R^3$ signifies that no more than two of these substituents are nitrogen-containing groups, i.e. amino, lower alkylamino, di-lower alkylamino and/or acylamino; moreover, no more than two of the substituents $R^1$–$R^3$ are oxygen containing groups, i.e. lower alkoxy-lower alkyl ($R^1$) and acylamino, lower alkoxy, lower alkoxymethoxy and/or a group $OR^4$ ($R^2$, $R^3$); moreover, $R^1$–$R^3$ can together only contain a maximum of two of said nitrogen and/or oxygen containing groups.

$R^5$ is hydrogen, optionally esterified carboxy or amidated (thio)carboxy, optionally substituted alkyl, optionally substituted alkenyl, optionally substituted acyl or heterocyclyl. Exemplary of esterified carboxy and amidated (thio)carboxy groups $R^5$ are groups of the general formula

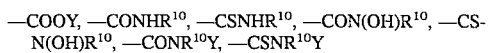

wherein $R^{10}$ is hydrogen or alkyl and Y is alkyl, alkenylalkyl, alkynylalkyl, lower cycloalkyl, lower cycloalkyl-lower alkyl, lower cycloalkyl-lower alkenylalkyl, heterocyclyl, heterocyclyl-lower alkyl, heterocyclyl-lower alkenylalkyl, aryl, aryl-lower alkyl or aryl-lower alkenylalkyl or wherein the residue —$NR^{10}Y$ represents the amino residue of an α-amino acid or peptide or a 5 to 7 membered saturated N-heterocyclus optionally containing a further N or an O or S atom.

Thus, possible meanings for Y are alkyl, e.g. methyl, ethyl, isopropyl, t-butyl, n-pentyl, n-decyl, etc., alkenylalkyl, e.g. 2-propenyl; alkynylalkyl, e.g. 2-propynyl, 3-butynyl; lower cycloalkyl, e.g. cyclopropyl, cyclobutyl, cyclopentyl, cyclohexyl; lower cycloalkyl-lower alkyl, e.g. cyclopropylmethyl, cyclopropylethyl; lower cycloalkyl-lower alkenylalkyl, e.g. cyclopropyl-2-propenyl; heterocyclyl, such as a 5 to 7 membered saturated or unsaturated heterocycle containing 1–4 nitrogen atoms and/or a sulfur or oxygen atom, e.g. 3-pyridyl, 2-pyrrolidyl, 2-pyrrolyl, 1-methyl-4-piperidyl, 1-ethoxycarbonyl-4-piperidinyl, thienyl, 4-thiazolyl; heterocyclyl-lower alkyl (where the heterocyclyl moiety is as defined above), e.g. furfuryl, thenyl, 4-thiazolyl-methyl, 3-methyl-5-isoxazolyl-ethyl, 1-morpholinyl-methyl, 4-methyl-1-piperazinylmethyl, 1-pyridinium-methyl; heterocyclyl-lower alkenylalkyl (where the heterocyclyl moiety is as defined above), e.g. 2-pyrrolyl-2-propenyl, 2-thienyl-2-propenyl; aryl, e.g. phenyl, p-tolyl, o,m-dihydroxyphenyl, m,p-dihydroxyphenyl, p-methoxyphenyl (anisyl), m-methoxyphenyl, o,m-dimethoxyphenyl, 3,4,5-trimethoxyphenyl, p-trifluoromethyl-phenyl, naphthyl; aryl-lower alkyl, e.g. benzyl, phenethyl; or aryl-lower alkenylalkyl, e.g. phenyl-2-propenyl. The said heterocyclyl or aryl groups may be bound to a fused saturated or unsaturated ring which may contain 1–4 nitrogen atoms and/or a sulfur or oxygen atom to form e.g. a quinolinyl, quinoxalinyl, benzoxazolyl, benzthiazolyl, benzimidazolyl, indolyl, s-triazolo[1,5-a]pyrimidyl or pyrazolo[1,5-a]pyrimidinyl group.

The residue —$NR^{10}Y$ can represent the amino residue of an α-amino acid or peptide. Such amino residues are e.g.

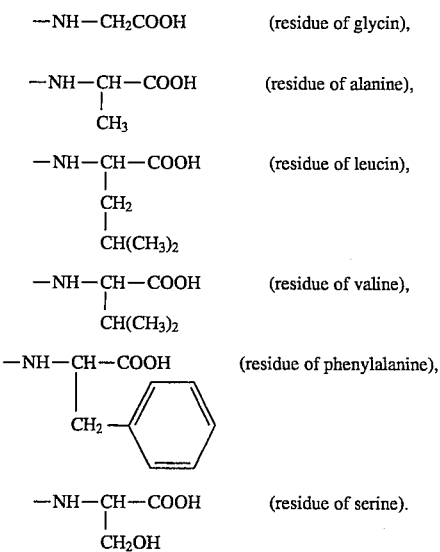

The residue —$NR^{10}Y$ can also represent a 5 to 7 membered saturated N-heterocyclus optionally containing a further N or an O or S atom, e.g. pyrrolidyl, piperidino, morpholino, thiomorpholino.

The above group Y can be further substituted, e.g.

by halogen, i.e. fluorine, chlorine, bromine or iodine;

by amino (such as in 2-amino-4-thiazolyl);

by lower alkylamino, e.g. methylamino;

by di-lower-alkylamino, e.g. dimethylamino;

by a quaternary ammonium group such as tri-lower alkylammonium, e.g. trimethylammonium, 1-pyridinium, 1-lower-alkyl-morpholinium, e.g. 1-methyl-morpholinium, or 1-quinuclidinium (in such case the positive charge of the quaternary ammonium group is neutralized by a pharmaceutically acceptable anion such as those exemplified below under the acid addition salts of the compounds of formula I. The anion can also be the deprotonated moiety of a carboxy group present in the compound of formula I, in which the compound is present in the form of a zwitterion);

by acylamino, e.g. acetamido, benzamido, p-toluoylamido;

by amidino (optionally mono-, di- or tri-substituted by lower alkyl, viz. a group of the formula —C(NRR')=NR" where R, R' and R" are hydrogen or lower alkyl);

by iminoyl (optionally mono or disubstituted by lower alkyl, viz. a group of the formula —CR=NR', where R and R' are hydrogen or lower alkyl);

by hydroxy;

by lower alkoxy, e.g. methoxy, ethoxy;

by lower alkylthio, e.g. methylthio, ethylthio;

by lower cycloalkoxy, e.g. cyclopropoxy;

by lower cycloalkylthio, e.g. cyclopropylthio;

by lower alkenylalkoxy, e.g. 2-propenoxy;

by lower alkenylalkylthio, e.g. 2-propenylthio;

by aryloxy, e.g. phenoxy, p-telyloxy, naphthyloxy;

by arylthio. e.g. phenylthio, p-tolylthio, naphthylthio;

by heterocyclyloxy, e.g. furyloxy or thienyloxy;

by heterocyclylthio, e.g. furylthio, thiienylthio or (2,5-dihydro-6-hydroxy-2-methyl-5-oxo-as-triazin-3-yl)thio;

by acyloxy, the acyl moiety of which is preferably derived from a carboxylic acid and is thus e.g. lower alkanoyl, e.g. formyl, acetyl, propionyl, isobutyryl, pivaloyl; lower alkenoyl, e.g. crotonoyl, isocrotonoyl; lower cycloalkanoyl, e.g. cyclopropylcarbonyl: aroyl, e.g. benzoyl, p-chlorbenzoyl, p-toluoyl, p-anisoyl, naphthoyl; heterocyclylcarbonyl, e.g. furoyl, thenoyl;

by lower alkylsulfinyl or -sulfonyl, e.g. methylsulfinyl or-sulfonyl or ethylsulfinyl or-sulfonyl;

by lower alkenylalkylsulfinyl or -sulfonyl, e.g. 2-propenylsulfinyl or -sulfonyl;

by lower cycloalkylsulfinyl or -sulfonyl, e.g. cyclopropylsulfinyl or -sulfonyl;

by arylsulfinyl or -sulfonyl, e.g. phenylsulfinyl or-sulfonyl or p-tolylsulfinyl or -sulfonyl;

by heterocyclylsulfinyl or-sulfonyl, e.g. furylsulfinyl or-sulfonyl or thienylsulfinyl or -sulfonyl;

by hydroxyimino or lower alkoxyimino, e.g. methoxyimino.

The above groups Y can further be substituted by carboxy which is optionally esterified or amidated, e.g. forming lower alkoxycarbonyl, carbamoyl or N-hydroxycarbamoyl (of which the last two may be N-substituted by lower alkyl or aryl).

Moreover, the above groups Y can be substituted by lower alkyl, e.g. methyl, ethyl, isopropyl; by halo-lower alkyl, e.g. 2-fluoroalkyl, trifluoromethyl, trichloromethyl; by hydroxy-lower alkyl, e.g. hydroxymethyl, 2-hydroxyethyl; by lower alkoxy-lower alkyl, e.g. methoxymethyl; ethoxymethyl; by lower cydoalkyl e.g. cyclopropyl, cyclobutyl, cydohexyl; by lower alkenyl, e.g. vinyl, 2-propenyl; by aryl, e.g. phenyl, p-telyl, p-methoxyphenyl, naphthyl; by heterocydyl, e.g. 2-pyrrolidyl, 2-pyrrolyl, 2-thienyl; by oxo, cyano, nitro, azido or sulfamoyl which may be substituted by lower alkyl or aryl, e.g. methylsulfamoyl, dimethylsulfamoyl, phenylsulfamoyl.

Examples of unsubstituted alkyl, alkenyl or acyl groups $R^5$ are given above for these expressions. These groups can, however, also be substituted, e.g. by hydroxy, halogen, optionally lower alkyl- or aryl-substituted carbamoyloxy, carboxy, N-hydroxycarbamoyloxy or a group of the general formula in which Y has the meaning given above, Q is —O—, —S—, —SO$_2$—, —COO—, —OCO—, —CONR$^{10}$—, —NR$^{10}$—, —NR$^{10}$—CO—, —NR$^{10}$SO$_2$—, —NR$^{10}$COO— or —NR$^{10}$CONR$^{10}$—, $R^{10}$ has the above meaning and m is zero or 1.

Consequently, substituted alkyl, alkenyl and acyl groups include groups such as hydroxymethyl
bromomethyl
fluoroethyl
aminomethyl
2-carboxyethyl
4-fluoro-1-butenyl
(carbamoyloxy)methyl
[(phenylcarbamoyl)oxy]methyl
methoxymethyl
[(4-carbamoylphenyl)thio]methyl
(ethoxycarbonyl)acetyl
2-[(2-thiazolyl)carbamoyl]ethyl
(dimethylamino)methyl
cyclopentanecarboxamidomethyl
(4-aminobenzenesulfonamido)methyl
[1-(benzyloxy)fomamido]methyl
(3-phenyl ureido)methyl.

The above enumerated definition of Y including its further substitution possibilities is to be understood pragmatically such that apparently meaningless combinations such as "alkyl substituted alkyl", "alkenyl substituted alkenyl", "alkyl substituted alkenyl" etc. are intended to means the abbreviated groups, i.e., the just stated expressions mean "alkyl", "alkenyl", and "alkenyl", respectively.

$R^5$ can also refer to a heterocyclyl group, in particular to a 5 membered heterocycle containing 1-4 nitrogen atoms and/or a sulfur or oxygen atom, optionally further substituted by lower alkyl, such as methyl, or amino.

$R^{7b}$ is hydrogen, optionally substituted hydroxy, —NR—A or —N=B, in which R is hydrogen or lower alkyl, A is hydrogen, optionally substituted alkyl, lower cycloalkyl, iminoyl, (thio)acyl, esterified carboxy or amidated (thio)carboxy and B is lower alkylidene. When $R^{7b}$ is substituted hydroxy the substituted is preferable selected among acyl and lower alkyl groups as defined above and aryl, preferably phenyl, which may be substituted by one or two nitro groups. A in its meaning as optionally substituted alkyl or lower cycloalkyl have a significance as explained above for $R^5$. A in its meaning as iminoyl, (thio)acyl, esterified carboxy or amidated (thio)carboxy can be groups of the formula

| —CR=N—Y$^1$ | (a: iminoyl) |
| —(X$^2$)$_n$—Y$^2$, SO$_2$Y$^2$ | (b: (thio)acyl) |
| —(CO)$_n$OY | (c: esterified carboxy) |
| —X$^2$NR$^{10}$Y$^1$, X$^2$NR$^{10}$CO—Y$^2$ | (d: amidated (thio)carboxy) | wherein R is hydrogen or lower alkyl, n is one or two, $Y^1$ is hydrogen or the group Y, $Y^2$ is hydrogen, lower alkenyl, lower alkynyl or the group Y and $X^2$ and Y are as above.

A in its meaning as an acyl group —(X$^2$)$_n$—Y$^2$ can be the acyl residue of an α-amino acid or peptide or an N-protected derivative thereof. Such acyl residues are e.g.

M—NH—CH$_2$—CO— (residue of glycine)

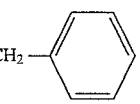
(residue of alanine)

(residue of leucine)

(residue of valine)

(residue of phenylalanine)

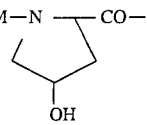
(residue of serine)

(residue of 3-hydroxyproline)

(residue of 4-hydroxyproline)

wherein M is hydrogen, lower alkanoyl, such as acetyl, or lower alkoxycarbonyl, such as methoxycarbonyl, ethoxycarbonyl or t-butoxycarbonyl ("BOC"),
and others. Two such residues can be connected with the formation of a dipeptide group, e.g.

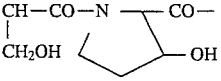

wherein M is as above.

Lower alkylidene groups B are e.g. groups of the general formulas

| =CHY | (e) |
| =C(Y)$_2$ | (f) |
| =CR$^{10}$—NR$^{10}$, Y$^1$ | (g) | wherein $R^{10}$, Y and $Y^1$ are as above.

$R^8$ in its meaning a optionally substituted alkyl, lower cycloalkyl, optionally esterified carboxy or amidated (thio)carboxy have a significance as explained above for $R^5$.

Preferred meanings for various substituents are:

$X^1$: —S—;

$R^1$, $R^3$, $R^6$, $R^{7a}$, $R^8$: Hydrogen or methyl;

$R^2$: Lower alkoxy, particularly methoxy or a group —OR$^4$, particularly hydroxy;

$R^4$: Hydrogen;

R⁵: $C_1$–$C_5$ Alkoxycarbonyl, allylamido, prop-2-ynylamido, 4-methyl-thiazol-2-yl, 3-methyl-1,2,4-oxadiazol-5-yl;

R$^{7b}$: Methoxycarbonylamino, hydroxy, formamido, t-butoxycarbonylamino, hydrogen, (thio)acetamido.

Preferred compounds of the invention are:

Methyl (4R, 7S)-1,3,4,5,6,7,8,10-octahydro-14-hydroxy-12-methoxy-4-methoxycarbonyl-11-methyl-6,10-dioxo-9,2,5-benzoxathiaazacyclododecine-7-carbamate, methyl (4R,7S)-1,3,4,5,6,7,8,10-octahydro-7,14-dihydroxy-12-methoxy-11-methyl-6,10-dioxo-9,2,5-benzoxathiaazacyclododecine-4-carboxylate, ethyl (4R,7S)-7-formamido-1,3,4,5,6,7,8,10-octahydro-14-hydroxy-12-methoxy-11-methyl-6,10-dioxo-9,2,5-benzoxathiaazacyclododecine-4-carboxylate, (4R, 7 S)-7-t-butoxycarbonylamino-1,3,4,5,6,7,8, 10-octahydro-14-hydroxy-12-methoxy-11-methyl-6,10-dioxo-9,2,5-benzoxathiaazacyclododecine-4-carboxylic acid allylamide, (4R,7S)-7-t-butoxycarbonylamino-1,3,4,5,6,7,8,10-octahydro-14-hydroxy-12-methoxy-11-methyl-6,10-dioxo-9,2,5-benzoxathiaazacyclododecine-4-carboxylic acid prop-2-ynylamide, methyl (4R)-1,3,4,5,6,7,8,10-octahydro-14-hydroxy-12-methoxy-10-oxo-6-thioxo-9,2,5-benzoxathiaazacyclododecine-4-carboxylate, ethyl (4R,7S)-1,3,4,5,6,7,8,10-octahydro-14-hydroxy-12-methoxy-11-methyl-6,10-dioxo-7-(thioacetamido)-9,2,5-benzoxathiaazacyclododecine-4-carboxylate, methyl (4R,7S)-7-(acetamido)-1,3,4,5,6,7,8,10-octahydro-14-hydroxy-12-methoxy-11-methyl-6,10-dioxo-9,2,5-benzoxathiaazacyclododecine-4-carboxylate, t-butyl (4R,7S)-4,5,6,7,8-tetrahydro-12,14-dihydroxy-11-methyl-4-(4-methyl-thiazol-2-yl)-6,10-dioxo-9,2,5-benzoxathiaazacyclododecine-7-carbamate, t-butyl (4R,7S)-4,5,6,7,8-tetrahydro-14-hydroxy-12-methoxy-11-methyl-4-(4-methyl-thiazol-2-yl)-6,10-dioxo-9,2,5-benzoxathiaazacyclododecine-7-carbamate, (4R,7S)-4,5,6,7,8-tetrahydro-7,12,14-trihydroxy-11-methyl-4-(3-methyl-1,2,4-oxadiazol-5-yl)-9,2,5-benzoxathiaazacyclododecine-6,10-dione, (4R,7S)-4,5,6,7,8-tetrahydro-7,14-dihydroxy-12-methoxy-11-methyl-4-(3-methyl-1,2,4-oxadiazol-5-yl)-9,2,5-benzoxathiaazacyclododecine-6,10-dione, N-[[(4R, 7S)-1,3,4,5,6,7,8,10-octahydro-12,14-dihydroxy-7-[[(3R)-3-hydroxy-1-L-seryl-L-propyl]amino]-11-methyl-6,10-dioxo-9,2,5-benzoxathiaazacyclododecin-4-yl]carbonyl]-L-alanine and pharmaceutically acceptable salts of any one of these compounds carrying an acidic and/or basic substituent.

Other, exemplary compounds of the invention are:

t-Butyl (4R,7S)-12,14-diacetoxy-1,3,4,5,6,7,8,10-octahydro-4-methoxycarbonyl-11-methyl-6,10-dioxo-9,2,5-benzoxathiaazacyclododecine-7-carbamate, t-butyl (4R,7S)-1,3,4,5,6,7,8,10-octahydro-12,14-hydroxy-4-methoxycarbonyl-11-methyl-6,10-dioxo-9,2,5-benzoxathiaazacyclododecine-7-carbamate, (4R,7S)-7-(1-t-butoxyformamido)-1,3,4,5,6,7,8,10-octahydro-12,14-dihydroxy-11-methyl-6,10-dioxo-9,2,5-benzoxathiaazacyclododecine-4-carboxylic acid, (4R,7S)-7-amino-1,3,4,5,6,7,8,10-octahydro-12,14-dihydro-11-methyl-6,10-dioxo-9,2,5-benzoxathiaazabicyclododecine-4-carboxylic acid, methyl (4R,7S)-12,14-diacetoxy-7-amino-1,3,4,5,6,7,8,10-octahydro-11-methyl-6,10-dioxo-9,2,5-benzoxathiaazacyclododecine-4-carboxylate, methyl (4R,7S)-7-amino-1,3,4,5,6,7,8,10-octahydro-12,14-dihydro-11-methyl-6,10-dioxo-9,2,5-benzoxathiaazacyclododecine-4-carboxylate, t-butyl (S)-12,14-diacetoxy-1,3,4,5.6,7,8,10-octahydro-11-methyl-6,10-dioxo-9,2,5-benzoxathiaazacyclododecine-7carbamate, t-butyl (S)-1,3,4,5,6,7,8,10-octahydro-12,14-dihydroxy-11-methyl-6,10-dioxo-9,2,5-benzoxathiaazacyclododecine-7-carbamate, (S)-7-amino-4,5,7,8-tetrahydro-12,14-dihydroxy-11-methyl-9,2,5-benzoxathiaazacyclododecine-6,10(1H,3H)-dione, methyl (4R,7S)-12,14-diacetoxy-7-[(Z)-2-(2-amino-4-thiazolyl)-2-(methoxyimino)acetamido]- 1,3,4,5,6,7,8,10-octahydro-11-methyl-6,10-dioxo-9,2,5-benzoxathiaazacyclododecine-4-carboxylate, methyl (4R,7S)-7-[(Z)-2-(2-amino-4-thiazolyl)-2-(methoxyimino)acetamido]- 1,3,4,5,6,7,8,10-octahydro-12,14-dihydroxy-11-methyl-6,10-dioxo-9,2,5-benzoxathiaazacyclododecine-4-carboxylate and pharmaceutically acceptable salts of any one of these compounds carrying an acidic and/or basic substituent.

Compounds of formula I carrying an acidic, e.g. carboxylic, substituent form pharmaceutically acceptable salts with bases. Examples of salts of compounds of formula I are the alkali metal salts, for examples the sodium and potassium salts, the ammonium salts, the alkaline earth metal salts, for example calcium salts, the salts with organic bases, for example with amines such as diisopropylamine, benzylamine, dibenzylamine, triethanolamine, triethylamine, N,N-dibenzylethylenediamine, N-methylmorpholine, pyridine, piperazine, N-ethylpiperidine, N-methyl-D-glucamine and procaine or with amino acids such as arginine and lysine. Mono-, di-, tri-salts etc. can result depending on the number of acidic groups in the compounds of formula I.

Compounds of formula I which have a basic, e.g. amino, substituent also form acid addition salts with organic and inorganic acids. Examples of acid addition salts of compounds of formula I are salts with mineral acids, for example hydrohalic acids such as hydrochloric acid, hydrogen bromide and hydrogen iodide, sulphuric acid, nitric acid, phosphoric acid and the like, salts with organic sulphonic acids, for example with alkyl- and arylsulphonic acids such as ethanesulphonic acid, p-toluenesulphonic acid, benzenesulphonic acid and the like, as well as salts with organic carboxylic acids, for example with acetic acid, tartaric acid, maleic acid, citric acid; benzoic acid, salicylic acid, ascorbic acid and the like.

The compounds of formula I and their pharmaceutically acceptable salts can be manufactured in accordance with the invention by a process which comprises a) cyclizing a carboxylic acid of the general formula

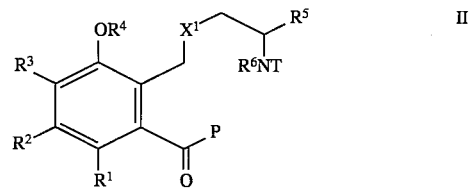

II in which P is hydroxy and T is the group —X²—CR$^{7a}$R$^{7b}$—$CHR^8$—OH or T is hydrogen and P is the group —O—$CHR^8$—CR$^{7a}$R$^{7b}$—X²—OH and X¹, X² and R¹–R⁸ are as above, or a reactive derivative thereof, or b) for the manufacture of a compound of formula I in which at least one of R², R³ and R$^{7b}$ is amino, reducing the nitro group(s) to amino in a compound of the general formula

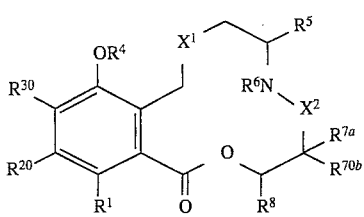

IIIa in which $X^1$, $X^2$, $R^1$, $R^4$, $R^5$, $R^6$, $R^{7a}$ and $R^8$ are as above and $R^{20}$, $R^{30}$ and $R^{70b}$ are as $R^2$, $R^3$ and $R^{7b}$ above except that at least one of these substituents represents nitro, or c) for the manufacture of a compound of formula I in which at least one of $R^2$, $R^3$ and $R^{7b}$ represents acylamino, acylating the amino group(s) in a compound of the general formula

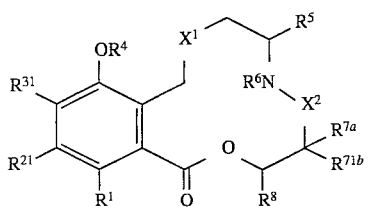

IIIb in which $X^1$, $X^2$, $R^1$, $R^4$, $R^5$, $R^6$, $R^{7a}$ and $R^8$ are as above and $R^{21}$, $R^{31}$ and $R^{71b}$ and as $R^2$, $R^3$ and $R^{7b}$ above except that at least one of these substituents represents amino, or d) for the manufacture of a compound of formula I in which $R^{7b}$ is the group —N=B reacting a compound of the general formula

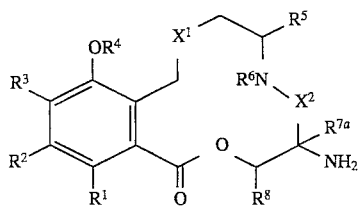

IV in which $X^1$, $X^2$, $R^1$–$R^6$, $R^{7a}$ and $R^8$ are as above, with a compound of the general formula

B=O in which B is lower alkylidene, or e) for the manufacture of a compound of formula I in which $R^5$ is esterified carboxy or amidated carboxy, reacting a compound of the general formula

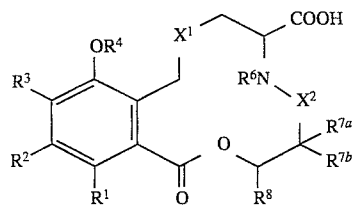

V in which $X^1$, $X^2$, $R^1$–$R^4$ and $R^6$–$R^8$ are as above and $X^3$ is oxygen or sulfur, with an agent yielding the corresponding ester or amide moiety, or f) for the manufacture of a compound of formula I, in which any of $R^2$, $R^3$, $R^5$ and/or $R^{7b}$ is or contains an amino, hydroxy and/or carboxy group cleaving off (a) protection group(s) in a compound of the general formula

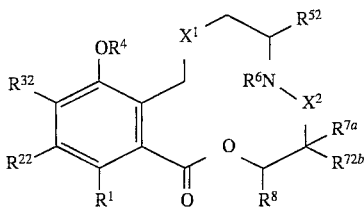

VI in which $X^1$, $X^2$, $R^1$, $R^4$, $R^6$, $R^{7a}$ and $R^8$ are as above and $R^{22}$, $R^{32}$, $R^{52}$ and $R^{72b}$ are as $R^2$, $R^3$, $R^5$ and $R^{7b}$ except that any amino, hydroxy and/or carboxy group is protected, or g) for the manufacture of a compound of formula I in which $X^1$ is —SO-oxidizing a compound of formula I in which $X^1$ is —S—, or h) for the manufacture of a pharmaceutically acceptable salt of a compound of formula I carrying an acidic and/or basic substituent converting such compound of formula I into such salt.

The cyclization in accordance with variant a) of the process in accordance with the invention consists of two types. One is an intramolecular esterification (lactonization) and utilizes starting materials of formula II in which P is hydroxy, viz. compounds of the general formula

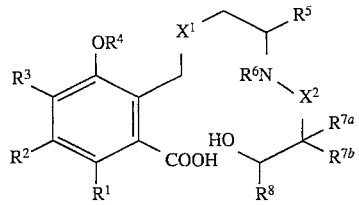

IIa in which $X^1$, $X^2$ and $R^1$–$R^8$ are as above, or reactive derivatives thereof. Preferred starting-materials are the reactive derivatives, viz. compounds corresponding to formula IIa, in which the carboxy function has been converted into a reactive derivative, preferably into a reactive derivative with an N-heteroaromatic thiol, in particular 2-mercaptopyridine or a di-lower alkyl substituted 2-mercaptoimidazole such as 4-t-butyl-N-isopropyl-2-mercaptoimidazole.

These N-heteroaromatic thiol esters can be prepared by reacting the disulfide corresponding to said thiol and triphenyl phosphine with the carboxylic acid of formula IIa. The reaction proceeds in an aprotic organic solvent such as benzene, toluene, xylene or methylene chloride and at a temperature between above −20° C. and +40° C., preferably at about 0° C. and +20° C. The reaction can proceed already under the said conditions. However, in general conversion is achieved to completion by heating the reaction mixture, preferably at reflux for about 0.1–20 hours.

Instead of the above N-heteroaromatic thiol ester an ester with a 1-lower alkyl-2-halopyridinium salt, preferably 1-methyl-2-chloropyridinium iodide, can be employed. For example, the starting compound of formula IIa is reacted with e.g. 1-methyl-2-chloropyridinium iodide in the presence of a tertiary amine such as triethylamine in an aprotic organic solvent such as acetonitrile or methylene chloride at a temperature between room temperature and the boiling point of the reaction mixture, preferably the latter.

According to a further alternative a reactive derivative with a di-lower alkyl azodicarboxylate, e.g. diethyl azodicarboxylate, and with triphenylphosphine is employed. For example, diethyl azodicarboxylate is added, dissolved in an aprotic organic solvent, such as benzene or toluene, to a solution of the starting compound of formula IIa and triphenylphosphine in the same solvent. The reaction can be carried out at a temperature between about −10° C. and +80° C., preferably at about 0° C. to about +30° C.

According to a further alternative the starting compound of formula IIa is cyclized with the aid of a mixture of a carbodiimide (such as dicyclohexylcarbodiimide), 4-(dimethylamino)pyridine and an acid addition salt, e.g. the hydrochloride, of the latter. This reaction preferably proceeds in an inert, aprotic organic solvent such as tetrahydrofuran or, preferably, chloroform at a temperature between about room temperature and reflux temperature, preferably at the latter.

The second type of the cyclization in accordance with variant a) of the process in accordance with the invention is an intramolecular amidation and utilizes starting materials of formula II in which T is hydrogen, viz. compounds of the general formula

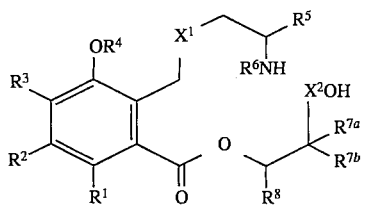

IIb in which $X^1$, $X^2$ and $R^1$–$R^8$ are as above, or reactive derivatives thereof. Reactive derivatives are compounds corresponding to formula IIb in which the carboxy function has been converted into a reactive derivative, preferably into an acid halide, particularly the chloride: into a mixed acid anhydride, particularly with trifluoroacetic acid or p-toluenesulfonic acid, or into a reactive thiol ester, particularly a 2-pyridine thiol ester. These derivatives are obtained in a manner known per se by reacting the starting compound of formula IIb with the corresponding add or with the disulfide corresponding to 2-pyridine thiol and triphenyl phosphine in the above mentioned manner. The cyclization of the reactive derivatives of the carboxylic add of formula IIb proceeds in an aprotic solvent such as toluene or methylene chloride at a temperature between about −20° C. and 130° C., preferably in the range of about 0° C. and 110° C.

The starting compounds of formula IIb themselves can be cyclized in the presence of carboxylic acid activators such as 1-lower alkyl-2-halopyridinium salts, e.g. 1-methyl-2-chloropyridinium iodide, dicyclohexylcarbodiimide or N-ethyl-5-phenyl-isoxazolium-3′-sulfonate, preferably in the presence of an organic base such as triethylamine or N-methylmorpholine. The reaction is carried out in an aprotic organic solvent such as methylene chloride or acetonitrile and at a temperature between about 0° C. and the boiling point of the reaction mixture.

The reduction of nitro groups $R^{20}$, $R^{30}$ and/or $R^{70b}$ to amino in starting compounds of formula IIIa according to variant b) of the process in accordance with the invention can be carried out in a manner known per se, e.g. by reaction with zinc, iron or tin in the presence of a mineral acid such as aqueous hydrochloric acid. The reaction is preferably carried out at a temperature in the range of about 0° C. to 50° C., optionally in the presence of a co-solvent such as tetrahydrofuran.

The acylation of amino groups $R^{21}$, $R^{31}$ and/or $R^{71b}$ in starting compounds of formula IIIb according to variant c) of the process in accordance with the invention can be carded out in a manner known per se, e.g. by reacting an amine of formula IIIb with the corresponding carboxylic acid in the presence of a coupling agent such as a carbodiimlde, e.g. dicydohexylcarbodiimide, or a 1-lower alkyl-2-halopyridinium salt, e.g. 1-methyl-2-chloropyridinium iodide, in an inert solvent such as acetonitrile, dioxane or tetrahydrofuran. It is also possible to use a reactive derivative of the said carboxylic acid such as e.g. an acid chloride, a mixed anhydride with another organic acid, e.g. trifluoroacetic acid or benzene sulfonic acid or a reactive thiolester such as e.g. an S-(2-benzothiazolyl)thioester.

For the acylation of an amine of formula IIIb with a residue of a sulfonic acid a reactive derivative of the sulfonic acid, e.g. a sulfonyl chloride, is reacted with an amine IIIb.

The acylation of the amine of the general formula IIIb is optionally performed in the presence of a base such as sodium bicarbonate, potassium carbonate, triethylamine, pyridine or N-methyl morpholine in an inert solvent such as methylene chloride, chloroform, tetrahydrofuran, dioxane, acetonitrile or N,N-dimethylformamide. The reaction temperature can vary in a wide range between about −50° C. and +100° C., preferably between about −20° C. and +50° C.

In accordance with variant d) of the process in accordance with the invention a cyclic amine of formula IV is reacted with an oxo compound of the formula B=O so as to obtain end products of formula I where $R^{7b}$ is the group —N=B. Compounds of formula B=O are e.g.

aldehydes, e.g. compounds of the general formula Y—CHO;

ketones, e.g. compounds of the general formula Y2CO: or

N-substituted oreides, e.g. compounds of the general formula

Y—NR$^{10}$—CR$^{10}$O where Y and $R^{10}$ are as above.

The said variant d) can be carried out in a manner known per se e.g. by reacting an aldehyde or a ketone corresponding to formula B=O with the amine of formula IV in an inert aprotic solvent, such as methylene chloride or toluene, and in the presence of an acidic catalyst such as p-toluenesulfonic acid and a water-binding agent such as molecular sieves or magnesium sulfate.

This reaction is preferably carried out at a temperature in a range of about 0°–60° C.

When the compound of the formula B=O is the above mentioned N-substituted amide, the latter is reacted via the corresponding iminoyl halide, preferably the iminoyl chloride, e.g. by treatment of said N-substituted amide with a chlorinating agent such as phosphorus pentachloride or phosphorus oxychloride and subsequently with the amine of formula IV. This reaction is carried out in an inert solvent such as methylene chloride or tetrahydrofuran and in the presence of a base such as triethylamine or pyridine. The reaction temperature preferably lies in the range of about −20° C. to +50° C.

In accordance with variant e) of the process in accordance with the invention a carboxylic acid of the formula V is esterified or a carboxylic acid of the formula I is amidated with an agent yielding the corresponding ester or amide moiety. For example, esterification may be accomplished by treatment of the carboxylic acid of formula V or a reactive derivative thereof, such as the corresponding acid chloride, acid anhydride, N-hydroxy-succinimide ester or methyl ester —with an alcohol of the general formula Y—OH; whereas amidation can be effected by treatment of a carboxylic acid of formula V —with an amine of the general formula NH$_2$R$^{10}$, NH(OH)R$^{10}$ or YNHR$^{10}$, where Y and R$^{10}$ are as above.

If the carboxylic acid of the formula V is reacted directly, i.e. without previous transformation into a reactive derivative, with an alcohol Y—OH (carboxylic acid V only) or with an amine $NH_2R^{10}$, $NH(OH)R^{20}$ or Y—$NHR^{10}$, a coupling agent such as a carbodiimide, e.g. clicyclohexylcarbodiimide, or a 1-lower alkyl-2-halopyridinium salt, e.g. 1-methyl-2-chloropyridinium iodide, should be used.

These esterification and amidation reactions are preferably carried out in an inert solvent such as methylene chloride, tetrahydrefuran or acetonitrile and at a temperature in the range of about −20° C. to +80° C.

According to variant f) of the process in accordance with the invention a starting compound of formula VI which is protected at any of amino, hydroxy and/or carboxy groups present) is deprotected to yield a compound of formula I with free amino, hydroxy and/or carboxy groups.

Possible amino-protecting groups are those employed in peptide chemistry, such as an alkoxycarbonyl group, e.g., t-butoxycarbonyl, etc., a substituted alkoxycarbonyl group, e.g., trichloroethoxycarbonyl, etc., a substituted aralkyloxycarbonyl group, e.g., p-nitrobenzyloxycarbonyl, an aralkyl group such as trityl or benzhydryl or a halogen-alkanoyl group such as chloroacetyl, bromoacetyl or trifiuoroacetyl.

Preferred amino-protecting groups are t-butoxycarbonyl, trityl and 2,2,2-trichloroethoxycarbonyl.

The amino protecting groups may be cleaved off by acid hydrolysis (e.g. the t-butoxycarbonyl or trityl group) or by basic hydrolysis (e.g. the trifiuoroacetyl group). The chloroacetyl, bromoacetyl and iodoacetyl groups are cleaved off by treatment with thiourea. The 2,2,2-trichloroethoxycarbonyl group is cleaved off by reduction with zinc and an acid.

Amino-protecting groups which are cleavable by acid hydrolysis are preferably removed with the aid of a lower alkanecarboxylic add which may be halogenated. In particular, formic acid or trifluoroacetic add is used. The acid hydrolysis is generally carried out at room temperature, although it can be carried out at a slightly higher or slightly lower temperature (e.g. at a temperature in the range of about 0° C. to +40° C.). Protecting groups which are cleavable under basic conditions are generally hydrolyzed with dilute aqueous alkali at 0° C. to +30° C. The chloroacetyl and bromoacetyl protecting groups can be cleaved off using thiourea in acidic, neutral or alkaline medium at about 0°–30° C. The 2,2,2-trichloroalkoxycarbonyl group is cleaved by treatment with zinc and an add, preferably aqueous acetic acid.

Possible hydroxy-protecting groups are the easily cleavable groups $R^4$ defined above, e.g. lower alkanoyl and lower alkoxycarbonyl. They may be cleaved by basic hydrolysis, e.g. treatment with an inoganic base such as an alkali metal hydroxide or carbonate in a lower alkanol, e.g. methanol, or tetrahydrofuran and at a temperature in the range of about 0° C. and room temperature. The aforesaid silyl groups can be cleaved by treatment with fluoride ions, e.g. by using ammonium fluoride or tetrabutylammonium fluoride in a solvent such as methanol or tetrahydrofuran, preferably at about 0° to room temperature. Hydroxy groups may further be protected or masked as acetals or ketals, e.g. as tetrahydropyranyl ethers or methoxymethyl ethers. From these protection groups the hydroxy function can be liberated by acidic hydrolysis. e.g. with aqueous hydrochloric acid.

As carboxy-protecting groups one may utilize an ester form which can be easily converted into a free carboxyl group under mild conditions, the carboxy-protecting group being exemplified by, for example, t-butyl, p-nitrobenzyl, benzhydryl, allyl, 2,2,2-trichloroethyl etc. For example, the following reagents and their corresponding compatible esters are utilized: p-nitrobenzyl can be removed by hydrolysis in the presence of sodium sulfide at about or below 0° C. to room temperature in a solvent, such as, dimethylformamide (aqueous); t-butyl can be removed by reaction with trifiuoroacetic acid, optionally in the presence of anisole at about 0° C. to room temperature with or without a co-solvent, such as methylene chloride: allyl can be removed by a palladium (O) catalyzed transallylation reaction in the presence of sodium or potassium salt of 2-ethyl hexanoic acid, see for example J. Org. Chem. 1982, 47,587; 2,2,2-trichloroethyl can be removed by reaction with zinc in a solvent such as aqueous acetic acid or a mixture of tetrahydrofuran and aqueous sodium dihydrogen phosphate.

The residues of in vivo easily cleavable esters may also be employed as carboxy-protecting groups. Examples of such esters, which can be of the conventional type, are the lower alkanoyloxalkyl esters (e.g., the acetoxymethyl, pivaloyloxymethyl, 1-acetoxyethyl and 1-pivaloyloxyethyl ester), the lower alkoxycarbonyloxyalkyl esters (e.g., the methoxycarbonyloxymethyl, 1-ethoxycarbonyloxyethyl and 1-isopropoxycarbonyloxyethyl ester). These easily cleavable esters groups may be split off by treatment with an esterase such as pig liver esterase in aqueous solution in the presence of a co-solvent such as tetrahydrofuran or dimethylsulfoxide and at a temperature in the range of about 30° C. and 40° C.

Also conventional lower alkyl groups, e.g. methyl and ethyl, are useful as carboxy-protecting groups: they can be split off in the same manner as the lower alkanoyl and lower alkoxycarbonyl groups $R^4$ described above. Thus, treatment with an inorganic base such as an alkali metal hydroxide or carbonate in a lower alkanol or tetrahydrofuran at about 0° C. to room temperature will remove these hydroxy and carboxy-protecting groups.

In the process variants a) to e) aforesaid $R^5$, $R^{7b}$, $R^{70b}$, $R^{71b}$ and $R^8$ preferably do not contain a thiocarbonyl group —CS— and/or $X^2$ is preferably not a thiocarbonyl group —CS—, this due to the relative instability of such intermediates. For the manufacture of end products of formula I containing such thiocarbonyl groups —CS— one preferably uses the corresponding carbonyl (—CO—) compound having any amino, hydroxy and/or carboxy group in the molecule protected as described above under f). The conversion —CO— to —CS— as a final step can then be accomplished by reaction with a thiation reagent such as phosphorus pentasulfide or, alternatively, with 2,4-bis-(4-methoxyphenyl)-2,4-dithioxo-1,3,2,4-dithiadiphosphetane (see Tetrahedron 37, 3635 (1981), followed by the cleavage of any amino, hydroxy and/or carboxy protection groups as described above under f).

The oxidation of the starting compounds of formula I in which $X^1$ is —S— according to embodiment g) yields the oxidized analogues of formula I wherein $X^1$ is —SO— (sulfoxides). This oxidation is carried out by using an organic or inorganic oxidizing agent. Various compounds which readily deliver oxygen can be used as the oxidizing agent; for example, organic peroxides such as monosubstituted organic peroxides (e.g. $C_{1-4}$ alkyl- or alkanoylhydroperoxides such as t-butylhydroperoxide), performic acid and peracetic acid, as well as phenyl-substituted derivatives of these hydroperoxides such as cumenetiydroperoxide and perbenzoic acid. The phenyl substituent can, if desired, carry a further lower group (e.g. a lower alkyl or lower alkoxy group), a halogen atom or a carboxy group (e.g. 4-methylperbenzoic acid, 4-methoxy-perbenzoic acid, 3-chloroperbenzoic acid and mono-perphthalic acid). Various inorganic oxidizing agents can also be used as the oxidizing agent: for example, hydrogen peroxide, ozone, permanganates such as potassium or sodium permanganate, hypochlorites such as sodium, potassium or ammonium hypochlorite, peroxymonosulphuric and peroxydisulphuric acid. The use of 3-chloroperbenzoic acid is preferred. The oxidation is advantageously carried out in an inert solvent, for example, in an aprotic inert solvent such as tetrahydrofuran, dioxane, methylene chloride, chloroform, ethyl acetate or acetone or in a protic solvent such as water, a lower alkanol (e.g. methanol or ethanol) or a lower alkanecarboxylic acid which may be halogenated (e.g. formic acid, acetic acid or trifluoroacetic acid). The oxidation is generally carried out at a temperature in the range of $-20°$ C. to $+50°$ C. In order to obtain the corresponding sulfoxide, i.e. a compound of formula I in which $X^1$ stands for —SO—, with substantial exclusion of the corresponding sulfone (i.e. where $X^1$ is —$SO_2$—) it is preferable to use the oxidizing agent in equimolar amounts or in slight excess in relation to the starting material.

The manufacture of the pharmaceutically acceptable salts of the compounds of formula I can be carried out in a manner known per se; for example, by reacting a carboxylic acid of formula I with an equivalent amount of the desired base or, conversely, a free base of formula I with an organic or inorganic acid. The reaction is conveniently carded out in a solvent such as water or an organic solvent (e.g. ethanol, methanol, acetone and the like). The temperature at which the salt formation is carded out is not critical. The salt formation is generally carded out at room temperature, but it can be carded out at a temperature slightly above or below room temperature, for example in the range of $0°$ C. to $+50°$ C.

The acid addition salts can be converted into a free form by treatment with a base, such as a metal hydroxide, ammonia and the like, the base salts are converted into the free form by treatment with an acid such as hydrochloric acid and the like.

The starting compounds of formulas II–VI can be prepared in accordance with the following flow sheets 1 and 2:

Compounds IIa can be manufactured according to flow sheet 1 as follows:

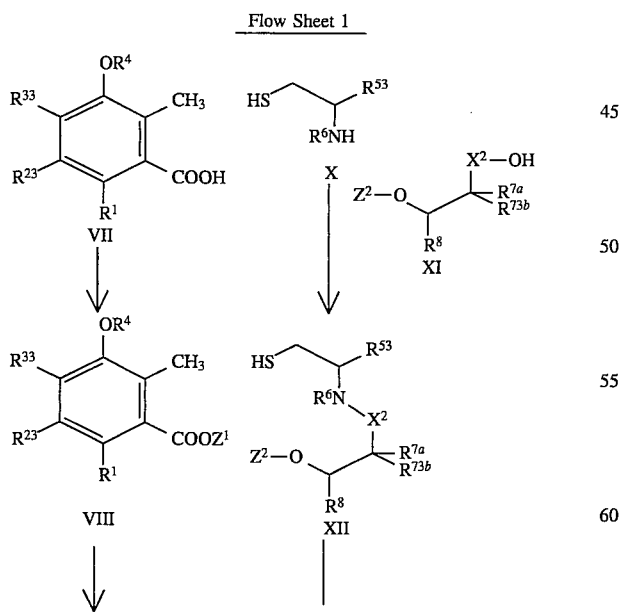

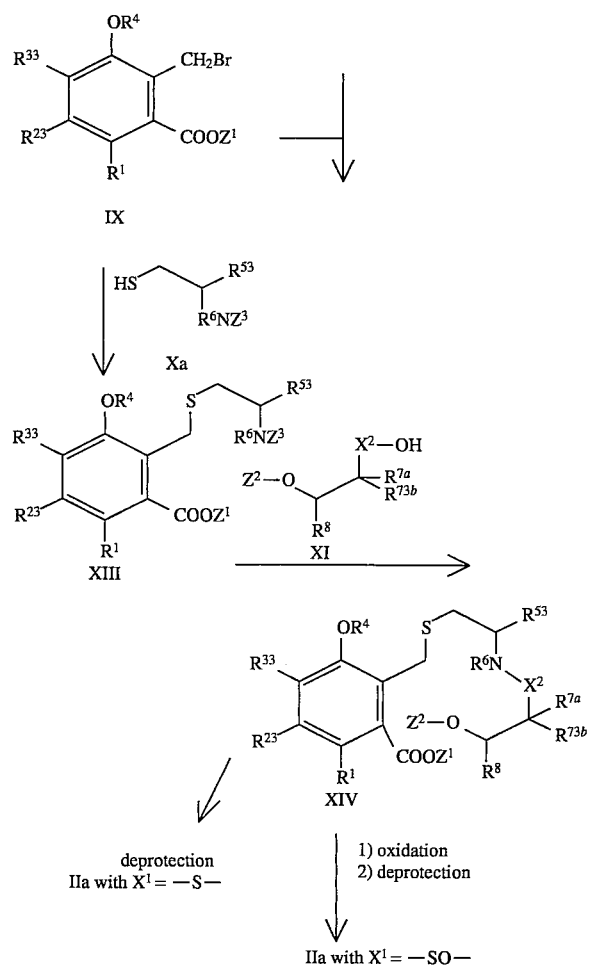

Compounds IIb can be manufactured according to Flow Sheet 2 as follows:

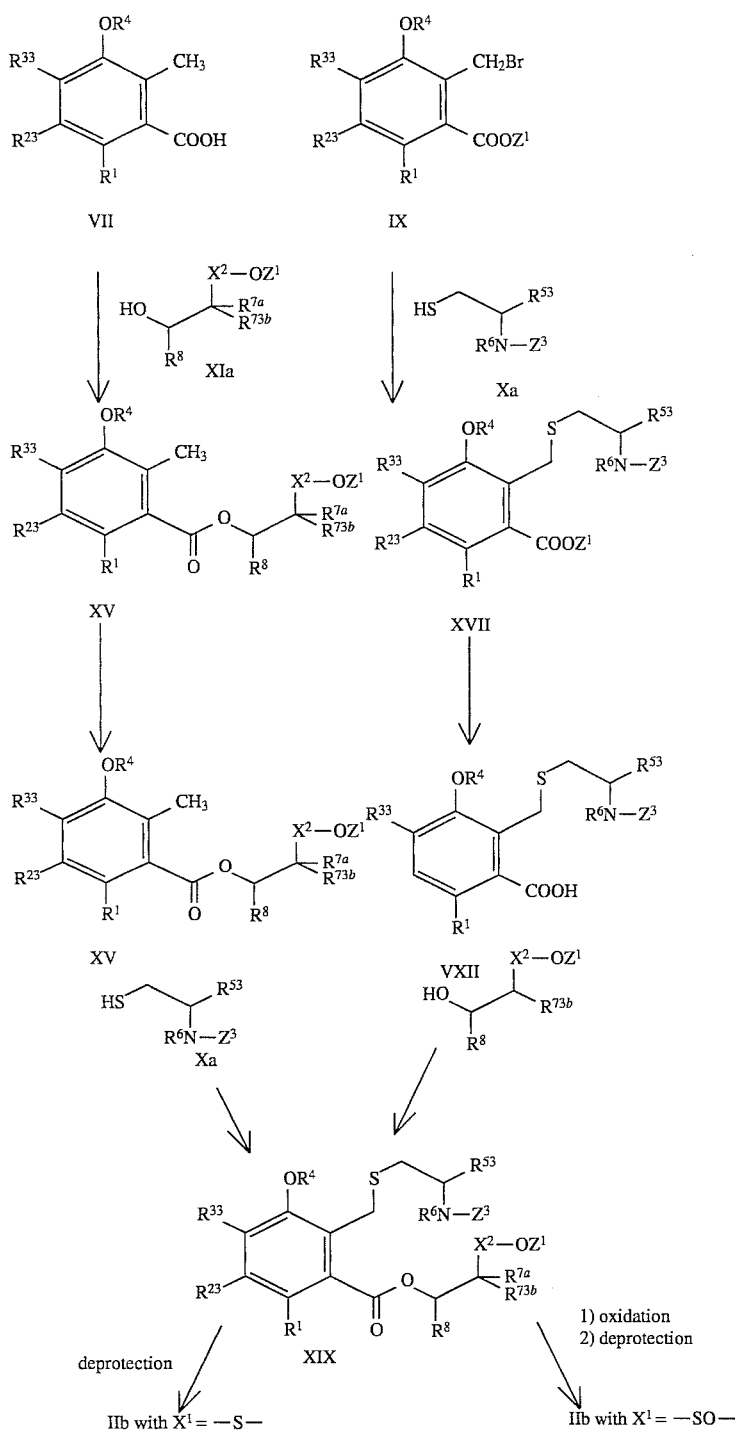

Flow Sheet II

In Flow Sheets 1 and 2 $R^1$, $R^4$, $R^6$, $R^{7a}$ and $R^8$ are as above and $R^{23}$, $R^{33}$, $R^{53}$ and $R^{73b}$ are as $R^2$, $R^3$, $R^5$ and $R^{7b}$, respectively, except that $R^{23}$, $R^{33}$ and $R^{73b}$ can also be nitro and $R^{23}$, $R^{33}$, $R^{53}$ and $R^{73b}$ can also contain a protected amino, hydroxy and/or carboxy group; $Z^1$ represents a carboxy protecting group, $Z^2$ is hydrogen or a hydroxy-protecting group and $Z^3$ is hydrogen or an amino protecting group. $X^2$ is preferably —CO—; end products with $X^2$=—CS— are preferably obtained as a final step as described above under f).

Protecting groups $Z^1$, $Z^2$ and $Z^3$ are such as are usually employed in the art for protecting carboxy, hydroxy or amino groups, respectively. Carboxy protecting groups $Z^1$ are e.g. allyl, p-nitrobenzyl or 2,2,2-trichloroethyl. As protecting groups $Z^2$ and $Z^3$ there come into consideration groups such as trityl, 2,2,2-trichloroethoxycarbonyl or t-butoxycarbonyl.

Besides the above mentioned easily cleavable hydroxy protecting groups, phenolic hydroxy groups of the intermediates VII and VIII can also be protected as methyl ethers, i.e. the substituents $R^{23}$, $R^{33}$ and/or $OR^4$ can also represent a methoxy group. In a later phase of the synthesis, e.g. after formation of the ester VIII, these methoxy groups can optionally be cleaved, e.g. using boron tribromide in methylene chloride at a temperature between −80° C. and +20° C., and the free phenolic functions can be reprotected by protecting groups more suitable for cleavage in the final product (e.g. lower alkanoyl, lower alkoxycarbonyl, tri-lower alkylsilyl or di-phenyl(lower alkyl)silyl).

Reactions of Flow Sheet 1

The manufacture of the starting materials of formula IIa can proceed according to Flow Sheet I as follows:

A substituted o-toluic acid of formula VII is converted into a reactive derivative thereof, e.g. to the acid chloride by reaction with thionyl chloride, oxalyl chloride or phosphoryl chloride, preferably in an inert solvent such as methylene chloride, chloroform or toluene. The acid chloride so obtained is thereafter reacted with an alcohol of the general formula $Z^1OH$, in which $Z^1$ is as above, e.g. with 2,2,2-trichloroethanol, preferably in an inert solvent such as methylene chloride or tetrahydrofuran in the presence of an organic base such as triethylamine or pyridine, to yield the desired ester of formula VIII.

The ester of formula VIII is converted into a substituted benzyl bromide of formula IX by bromination e.g. by reaction with N-bromosuccinimide in refluxing carbontetrachloride in the presence of a radical starter such as α,α'-azo-isobutyronitrile or under irradiation with light, or alternatively by treatment with bromine in an inert solvent such as carbontetrachloride under irradiation with light.

The so obtained substituted benzyl bromide of formula IX can be condensed with a thiol of formula XII to yield a thioether of formula XIV. The reaction is preferably effected in an inert organic solvent such as methylene chloride, ethyl acetate, N,N-dimethylformamide, dimethylsulfoxide, acetonitrile or ethanol in the presence of a weak non-nucleophilic organic base such as triethylamine, or in the presence of an inorganic base such as sodium or potassium carbonate. The reaction temperature preferably lies between −60° C. and +60° C., preferably between 0° C. and +30° C.

The thiol of formula XII can be obtained by amidating a carboxylic acid of formula XI with an aminothiol of formula X in a manner commonly known in peptide chemistry. According to a particularly preferred method compounds X and XI are reacted with each other in the presence of a condensation agent such as N,N'-dicyclohexylcarbodiimide, preferably in an aprotic organic solvent, such as acetonitrile, dioxane or methylene chloride, and at a temperature between −20° C. and +20° C., preferably at −10° C. to +10° C. The aminothiol of formula X can be utilized as base or as salt with an inorganic or organic acid, e.g. as hydrochloride; in the latter case an organic base such as N-methylmorpholine need be added in the reaction, preferably in equimolar amount.

An alternative method for obtaining the thioether of formula XIV consists in reacting the substituted benzyl bromide of formula IX with the aminothiol of formula Xa (substantially as described for the condensation of compounds IX and XII). The so obtained amine of formula XIII is thereafter reacted with the carboxylic acid of formula XI (substantially as described above for the amidation reaction involving compounds X and XI).

The starting compound of formula IIa, where $X^1$ is —S—, is obtained by cleavage of the protecting groups $Z^1$ and $Z^2$ in the thioether of formula XIV so obtained. This is carried out as already described above for the deprotection of starting compounds V according to variant f).

By oxidizing a thioether of formula XIV obtained in the manner described above for process alternative g), e.g. by oxidizing with 3-chloroperbenzoic acid in methylene chloride and subsequently splitting off the protecting groups $Z^1$ and $Z^2$ the corresponding sulfoxide, i.e. starting compounds of formula II, wherein $X^1$ is —SO—, are obtained.

Reactions of Flow Sheet 2

The manufacture of the starting compounds IIb employed as starting materials can proceed according to flow sheet 2 as follows:

A substituted o-toluic acid of formula VII is converted to the compound of formula XV in analogy to the above conversion of compounds VII to esters of formula VIII. In so doing, the intermediate carboxylic acid chloride is reacted with an alcohol of formula XIa.

The conversion of the compound of formula XV obtained into the substituted benzyl bromide of formula XVI is effected by bromination in analogy to the conversion of the ester VIII into the substituted benzyl bromide of formula IX.

The substituted benzyl bromide of formula XVI can be condensed with a thiol of formula Xa to yield a thioether of formula XIX in accordance with the method described above for the manufacture of compounds XIV from compounds XII.

The thioether of formula XIX can alternatively be obtained by esterification or amidation of a carboxylic acid of formula XVIII with an alcohol of formula XIa suitably employing a condensation agent such as N,N'-dicyclohexylcarbodiimide, and in an inert organic solvent such as acetonitrile or dioxane.

The thioether of formula XVIII employed in the above reaction can be obtained by reacting a substituted benzyl bromide of formula IX with a thiol of formula Xa (substantially in accordance with the above described manufacture of compounds XIV from compounds XII). The thioether of formula XVII so obtained is subsequently submitted to ester cleavage (the ester protection group $Z^1$ being split off). The ester cleavage is carried out in a manner known per se; when $Z^1$ is 2,2,2-trichloroethyl the cleavage can be carried out by treatment with zinc powder in aqueous acetic acid.

For the manufacture of starting compounds IIb, where $X^1$ is —S—, the protecting groups $Z^1$ and $Z^2$ in the intermediate of formula XIX obtained are cleaved off in a manner known per se, e.g. as described above. By oxidizing intermediates of formula XIX in a manner described according process alternative g) above and subsequently cleaving off the protecting groups $Z^1$ and $Z^2$ starting compounds of formula IIb, wherein $X^1$ is —SO—, are obtained.

It has also been found that one derivative falling within the general formula I, viz. the compound of formula

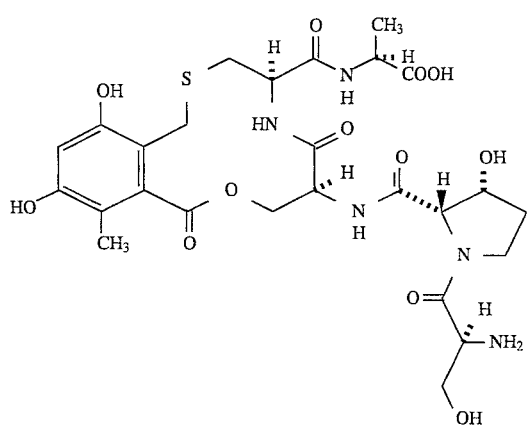

i.e. N-[[(4R,7S)-1,3,4,5,6,7,8,10-octahydro-12,14-dihydroxy7-[[(3R)-3-hydroxy-1-L-seryl-L-prolyl)]amino]-11-methyl-6,10-dioxo-9,2,5-benzooxathiaazacyclododecin-4-yl]carbonyl]-L-alanine, is obtainable by fementation, more particularly by cultivating a subculture of the microorganism Streptomyces sp. NR0484 FERM-BP-1982 under submerged, aerobic conditions in an aqueous carbohydrate solution containing nitrogenous nutrients and sodium chloride, thereafter isolating the desired compound from the fermentation broth and, if desired, converting the product obtained into a pharmaceutically acceptable salt thereof, e.g. the sodium salt.

The organism producing compound Ia is a new strain designated Streptomyces sp. NR0484. The organism given the laboratory designation NR0484 was deposited on Jul. 27, 1988, at Fementation Research Institute (FRI), 1-3, Higashi I-chome, Yatabe-machi. Tsukuba-gun, ibaraki-ken 305, Japan, under the Budapest Treaty and added to its collection of microorganisms as FERM-BP-1982. The culture has been identified as a strain of Streptomyces filipinensis.

Strain NR0484 was isolated from a sandy soil sample collected at Ohsemachi Hamamatsu City, Shizuoka, Japan by directly spreading onto than potato carrot agar medium (Higgins, M. L., M. P. Lechevalier and H. A. Lechevalier: Flagellated actinomycetes, J. Bacteriol. 93:1446–1451, 1967) supplemented with 10% grated radish. Strain NR[0484] was directly compared with the type strain (IF012860)of Streptomyces filipinensis.

The taxonomic studies were done according to the procedure adopted by the International Streptomyces Project (ISP) using the media recommended by Shirling, E. B. and D. Gottlieb (Method for characterization of Streptomyces species; Intern. J. Syst. Bact. 16:313–340, 1966) and by Waksman, S. A. (Classification, identification and description of genera and species; in The Actinomycetes Vol. II; The Williams and Wilkins Co., Baltimore, 1961). All cultures were incubated at 27° C. for 15 days. The colour scheme in the Colour Harmony Manual (4th ed., 1958; Container Corporation of America, Chicago) was used to describe the pigmentation of the colonies. Sodium chloride tolerance of the strains and their growth at various temperatures were tested on ISP medium No. 3 (Difco) containing 0.15% yeast extract; and streptomycin sensitivity of the strains were tested on ISP medium No. Z (Difco).

Cells for chemotaxonomic analyses were obtained from cultures in yeast-glucose broth (containing 1% yeast extract and 1% glucose, pH 7.2). The analysis of whole cell hydrolyzates was done according to the thin-layer chromatographic procedure of Staneck, J. I. and G. D. Roberts (simplified approach to identification of aerobic actinomycetes by thin-layer chromatography; Appl. Microbiol. 28:226–231, 1974). The cell wall preparation was obtained from washed mycelia by the method of Yamaguchi, T. (comparison of the cell wall composition of morphologically distinct actinomycetes, J. Bacteriol. 89:444–453, 1965). The procedure of Becker, B., M. P. Lechevalier and H. A. Lechevalier (Chemical composition of cell-wall preparations from strains of various form-genera of aerobic actinomycetes; Appl. Microbiol. 13:236–243, 1965) was used to identify amino acids in the cell wall.

Description of Strain NR0484

Morphological and chemical characteristics

Strain NR0484 grew well on agar media of various compositions showing characteristic growth for Streptomycetes and formed aerial mycelia. The spore chain morphology consisted of spirals which could be categorized as spirales. More than 50 oval to cylindrical mature sporechains were formed. The surface of the spores were spiny and their dimensions were 0.6–0–0.9×0.9–1.2 µm.

Whole cell hydrolysates of the strain contained LL-diaminopimelic acid, but not meso-diaminopimelic acid, and glycine was detected in the cell wall. Thus, the cell wall type of this strain is chemotype I of Lechevalier, M. P. and H. A. Lechevalier (Chemical composition as a criterion in the classification of aerobic actinomycetes; Intern. J. Syst. Bact. 20:435–443, 1970).

Based on the morphology and chemical characteristics of strain NR0484, this organism was assigned to the genus Streptomyces.

Cultural Characteristics

The growth characteristics of strain NR0484, cultivated for 15 days at 27° C., on various agar media are summarized in Table 1. Media ISP 2, 3, 4, 5 and 7 supported the best growth and abundant sporulation. The colour of aerial mycelia matched that of the Gray colour series, whereas the colour of diffusible pigment could not be distinguished.

TABLE 1

| Cultural characteristics of strain NR0484 | |
|---|---|
| Medium | Cultural characteristics |
| Sucrose nitrate agar (Waksman medium No. 1) | G: moderate, colourless<br>AM: thin, beige (3ge)<br>R: beige (3ge)<br>DP: none |
| Yeast ext.-malt ext. agar (ISP medium No. 2) | G: good, colourless<br>AM: good, ashes (5fe)<br>R: clove braun (3ni)<br>DP: none |
| Oatmeal agar (ISP medium No. 3) | G: good, yellow maple (3ng)<br>AM: good, ashes (5fe)<br>R: beaver (3li)<br>DP: none |
| Inorganic salts-starch agar (ISP medium No. 4) | G: good, yellow maple (3ng)<br>AM: good, ashes (5fe)<br>R: adobe brown (3lg)<br>DP: none |
| Glycerol asparagine agar (ISP medium No. 5) | G: good, beaver (3li)<br>AM: good, ashes (5fe)<br>R: beaver (3li)<br>DP: none |
| Glucose asparagine agar (Waksman medium No. 2) | G: moderate, amber (3lc)<br>AM: thin, pussywillow gray (5dc)<br>R: amber (3lc)<br>DP: none |
| Tyrosine agar (ISP medium No. 7) | G: good, glove brown (3ni)<br>AM: good, ashes (5fe) |

TABLE 1-continued

Cultural characteristics of strain NR0484

| Medium | Cultural characteristics |
|---|---|
| Nutrient agar (Waksman medium No. 14) | R: clove brown (3ni)<br>DP: none<br>G: moderate, colourless<br>AM: thin, alabaster tint (13ba)<br>R: clove brown (3ni)<br>DP: none |

G: Growth
AM: Aerial mycelium
R: Reverse
DP: Diffusible pigment

Physiological Characteristics

The carbon utilization and other physiological characteristics of strain NR0484 as well as Streptomyces filipinensis IFO 12860 are shown in Tables 2 and 3. Both strains utilized carbohydrates similarly and had similar physiological properties.

Species Determination

When strain NR0484 was compared with Streptomyces species described in the literature, S. filipinensis (Atomann, A., D. Gottlieb, T. D. Brock, H. E. Carter and G. B. Whitfield: Filipin, an antibiotic effective against fungi; Phytopathology, 45:559–563, 1955) most closely resembled strain NR0484. Therefore, the microbiological characteristics of strain NR0484 were directly compared with those of S. filipinensis IFO 12860, and it was found that strain IFO 12860 grown in the same production medium differed from strain NR0484 in that it could not produce DNA-gyrase inhibitor compound Ia. In spite of this minor difference, strain NR0484 and strain IFO12860 showed numerous similarities in other properties including morphology and cultural characteristics. Thus, it was concluded that strain NR0484 could be assigned to the species Streptomyces filipinensis. For the purpose of the present invention Streptomyces sp. NR0484 includes all strains of Streptomyces which form compound Ia and which cannot be definitely differentiated from the culture numer NR0484 and its subcultures, including mutants and variants. Compound Ia is identified herein and after this identification is known, it is easy to differentiate the strains producing compound Ia from others.

TABLE 2

Carbohydrate utilization by strain NR0484 and Streptomyces filipinensis IFO12860

| | strain NR0484 | S. filipinensis IFO12860 |
|---|---|---|
| L-Arabinose | + | + |
| D-Xylose | + | + |
| G-Glucose | + | + |
| D-Fructose | + | + |
| Sucrose | ± | + |
| Inositol | ± | + |
| L-Rhamnose | ± | ± |
| Raffinose | ± | + |
| D-Mannitol | + | + |

+: Utilization
±: Probable utilization

TABLE 3

Physiological characteristics of strain NR0484 and Streptomyces filipinensis IFO12860

| | strain NR0484 | S. filipinensis IFO12860 |
|---|---|---|
| Gelatin liquefaction (Waksman medium No. 19) | − | − |
| Starch hydrolysis (ISP medium No. 4) | + | + |
| Milk coagulation (Difco 10% skimmed milk) | − | − |
| Milk peptonization (Difco 10% skimmed milk) | + | + |
| Nitrate reduction (ISP medium No. 8) | − | − |
| Melanoid pigment formation | | |
| ISP medium No. 1 | + | + |
| ISP medium No. 6 | + | + |
| ISP medium No. 7 | − | − |
| NaCl tolerance | >4%, but <10% | >4%, but <10% |
| Streptomycin sensitivity (M.I.C., mg/ml) | 6.3 | 6.3 |
| Temperature range for growth | 20–45° C. | 20–45° C. |
| Optimum temperature for growth | 30–37° C. | 30–37° C. |
| Production of DNA-gyrase inhibitor in A24 medium | + | − |

+: Positive
−: Negative

Effect of Carbon and Nitrogen Sources

Five carbon sources and 21 nitrogen sources were tested for the production of compound Ia. Glucose was the best carbon source and yeast extract supplemented with-soybean meal (Toast soya, Nishin Seiyu) was the best nitrogen source.

Effect of Metal Ions

Following the studies on carbon and nitrogen sources, the influence of $CaCO_3$ and NaCl was investigated. NaCl was necessary for the production of compound Ia, whereas $CaCO_3$ caused less coproduct(s) to be made.

Based on the data described above, a fermentation medium, named A24 medium consisting of 2% glucose. 2% Toast soya, 0.5% yeast extract, 0.25% NaCl, 0.005% $ZnSO_4 \cdot 7H_2O$, 0.0005% $CuSO_4 \cdot 5H_2O$ and 0.0005% $MnCl_2 \cdot 4H_2O$ was selected as preferred fermentation medium.

Streptomyces sp. NR0484, when grown under suitable conditions, produces a compound of the formula Ia. A fermentation broth containing Streptomyces sp. NR0484 is prepared by inoculating spores or mycelia of the organism producing compound Ia into a suitable medium and then cultivating under aerobic conditions. For the production of compound Ia cultivation on a solid medium is possible, but for production in large quantities cultivation in a liquid medium is preferable. The temperature of the cultivation may be varied over a wide range, 20°–35° C., within which the organism may grow, but a temperature of 26°–30° C. and a substantially neutral pH are preferred. In the submerged aerobic fermentation of the organism for the production of compound Ia the medium may contain as the source for carbon a commercially available glyceride oil or a carbohydrate such as glycerol, glucose, maltose, lactose, dextrin, starch etc. in pure or crude states, and as the source of nitrogen an organic material such as soybean meal, distillers' solubles, peanut meal, cotton seed meal, meat extract, peptone, fish meal, yeast extract, corn steep liquor etc. and when desired inorganic sources of nitrogen such as nitrates and ammonium salts. Mineral salt present is sodium chloride, optionally also e.g. ammonium sulfate, magnesnium sulfate, potassium chloride, potassium phosphate, calcium carbonate and trace mounts of heavy metal salts. The medium may also contain buffering agent such as sodium citrate or phosphates. In aerated submerged culturing procedures, an anti-foam agent, such as liquid paraffin, fatty oils or silicone compounds, is preferably used. More than one kind of carbon source, nitrogen source or anti-foam source may be used for production of compound Ia.

After termination of fermentation compound Ia or its salts can be recovered from the fermentation medium. This can be accomplished by a combination of a variety of methods, for example, 1) adsorption on a adsorbent such as activated charcol and Diaion HP-21 (Mitsubishi Chemical Ind., Tokyo), 2) column chromatography on ion exchange resin such as Amberlite CG-50, IRC-50, DEAE-Toyopearl, QAE-Toyopeafi (TOSOH, Tokyo), DEAE-Sephadex and QAE-Sephadex, 3) reverse phase column chromatography, 4) gel filtration using e.g. Toyopeafi HW-40, Sephadex LH-20, Sephadex G-10, Sephadex G-15 and Sephadex G-25.

The compounds of formula I as well as their corresponding pharmaceutically acceptable salts inhibit DNA gyrase activity in bacteria and possess antibiotic, especially bactericidal activity against microorganisms.

A. Inhibition of DNA Gyrase Activity

The inhibition of DNA gyrase activity was measured using a DNA gyrase supercoiling assay according to R. Otter & N. Cozzarelli:Methods in Enzymology, Vol. 100, pp 171–180 (1983). DNA gyrase was isolated from E. coli H560, and relaxed pUC18 plasmid was used as substrate. The activities as regards inhibition of DNA gyrase activity, expressed as maximum non-effective concentration of the test compound (MNC in μg/ml) are compiled in the following Table 4:

TABLE 4

| End product from Example No. | MNC (μg/ml) |
|---|---|
| 2 | 0.1 |
| 3 | 5 |
| 4 | 1 |
| 5 | 10 |
| 6 | 2 |
| 9 | 1 |
| 10 | 10 |
| 12 | 5 |
| 13 | 0.05 |
| 41 | 0.1 |
| 69 | 0.05 |
| 84 | 0.1 |
| 101 | 0.1 |
| 102 | 0.25 |
| 137 | 0.2 |

B. Antibacterial Activity in Vitro

In the following table there are compiled the minimum inhibitory concentrations (MIC; μg/ml) of some representative compounds of formula I against a series of pathogenic microorganisms.

| | MIC (μg/ml) Compound of Example | | | | | |
|---|---|---|---|---|---|---|
| Organism | 41 | 69 | 84 | 101 | 102 | 137 |
| E. coli DC2 | 64 | 16 | >128 | 64 | 64 | 64 |
| E. coli B | 128 | 32 | >128 | 64 | 64 | 64 |
| N. meningitidis 69480 | 8 | 2 | 4 | 8 | 2 | 8 |
| B. catarrhalis RA 117 | 4 | 4 | 4 | 4 | 2 | 4 |
| S. aureus 887 | 32 | 32 | 16 | 16 | 8 | 32 |
| S. aureus 25923 | 32 | 128 | 32 | 16 | 16 | 128 |
| S. pyogenes 15 | 16 | 4 | 16 | 16 | 8 | 8 |
| S. faecalis 6 | 32 | 16 | 32 | 32 | 16 | 64 |

Agar dilution (BB2+1% Isovitalex+7.5% sheep blood+metadione), Inoculum: $10^4$ CFU/spot.

The products in accordance with the invention can be used as medicaments, e.g. in the form of pharmaceutical preparations for enteral or parenteral application. They can be administered, for example, perorally, e.g. in the form of tablets, coated tablets, dragees, hard and soft gelatine capsules, solutions, emulsions or suspensions, rectally, e.g. in the form of suppositories, or parenterally e.g. in the form of injection solutions.

The manufacture of the pharmaceutical preparations can be effected in a manner which is familiar to any person skilled in the art by bringing the substances in accordance with the invention, optionally in combination with other therapeutically valuable substances, into a galenical administration form together with suitable, non-toxic, inert, therapeutically compatible solid or liquid carrier materials and, if desired, the usual pharmaceutical adjuvants.

As such carrier materials not only inorganic carrier materials are suitable, but also organic carrier materials. Thus, there can be used as carrier materials for tablets, coated tablets, dragees and hard gelatine capsules, for example, lactose, maize starch or derivatives thereof, talc, stearic acid or its salts. Suitable carriers for soft gelatine capsules are, for example, vegetable oils, waxes, fats and semi-solid and liquid polyols (depending on the nature of the active substance no carriers are, however, required in the case of soft gelatine capsules). Suitable carder materials for the manufacture of solutions and syrups are, for example, water, polyols, saccharose, invert sugar and glucose. Suitable carder materials for injection solutions are, for example, water, alcohols, polyols, glycerine and vegetable oils. Suitable carder materials for suppositories are, for example, natural or hardened oils, waxes, fats and semi-liquid or liquid polyols. The pharmaceutical preparations can also contain other therpeutically valuable substances.

As pharmaceutical adjuvants there come into consideration the usual preservatives, solubilizers, stabilizers, wetting agents, emulsifiers, sweeteners, colorants, flavorants, salts for varying the osmotic pressure, buffers, coating agents and antioxidants.

The pharmaceutical preparations can contain the substances in accordance with the invention in amounts of about 25–2000 mg, preferably 100–1000 mg, per unit dosage form. For the prophylaxis and therapy of infectious diseases there comes into consideration for adults a daily dosage of about 0.05 g to about 4 g, especially about 0.1 g to about 2 g.

The following Examples are intended to illustrate the present invention in more detail, but are not intended to limit its scope in any manner.

EXAMPLE 1

To 1.1 g of 3,5-diacetoxy-6-[[(R)-2-((S)-2-(1-t-butoxyformamido)-3-hydroxypropionamido]-2-(methoxycarbonyl- )ethyl)thio]methyl]-2-methylbenzoic acid in 19 ml of toluene were added at 0° C. 1.14 g 2,2'-dithiobis(4-t-butyl-1-isopropylimidazole) and 0.74 g of triphenylphosphine. After stirring for 40 minutes at 0° C., the heterogenous mixture was diluted with 80 ml of toluene. The whole mixture, while remaining cooled at 0° C. in a dropping funnel, was added over a period of 2 hours to 40 ml of toluene which were kept at reflux temperature. After complete addition, the reaction mixture was heated at reflux for another 3 hours. The mixture was cooled and the solvent evaporated in vacuo. The residue was stirred in 30 ml of ethyl acetate at 0° C. for 1 hour and the crystalline 4-t-butyl-N-isopropyl-2-mercaptoimidazole formed was removed by filtration. The filtrate was evaporated in vacuo, and the residue was chromatographed using ethyl acetate/n-hexane (1:1, v/v) as eluent. Crystallization of the purified product from ethyl acetate/n-hexane afforded t-butyl (4R,7S)-12,14-diacetoxy-1,3,4,5,6,7,8,10-octahydro-4-methoxycarbonyl-11-methyl-6,10-dioxo-9,2,5-benzoxathiaazacyclododecine-7-carbamate as white crystals with mp 139° C. (decomposition).

$^1$H-NMR (DMSO-d$_6$): δ1.41 (s,9H); 2.02 (s,3H); 2.31 (s,6H); 2.95 (dd,J=14 Hz and 9 Hz,1H); 3.14 (dd,J=14 Hz and 4 Hz,1H); 3.43 (d,J=11 Hz,1H); 3.63 (s,3H); 3.86 (d,J=11 Hz, 1H); 4.28 (dd,J=12 Hz and 4 Hz,1H); 4.34–4.45 (m,1H); 4.51–4.14 (m,1H); 4.88–4.99 (m,1H); 7.12 (s,1H); 7.36 (d,J=8 Hz,1H); 8.26 (d,J=8 Hz,1H) ppm The starting material used above was prepared as follows:

(a) A solution of 10.75 g of 3,5-diimethoxy-2,6-dimethylbenzoic acid in 10.7 ml of thionyl chloride was heated at reflux for 45 minutes, when gas evolution had ceased completely. The mixture was cooled to room temperature, whereupon a precipitate formed. Excess reagent was evaporated in vacuo, 20 ml of toluene were added, and the mixture was evaporated to dryness. The solid residue was dissolved in 50 ml of methylene chloride, and 9.2 g of 2,2,2-trichloroethanol were added to the solution. The mixture was cooled to 0° C., and a solution of 6.2 g of triethylamine in 13 ml of methylene chloride was added within 10 minutes. After stirring for ten minutes at 0° C. and for 3 hours at room temperature the reaction mixture was washed consecutively with 30 ml portions of 3N hydrochloric acid, water, saturated aqueous sodium carbonate solution and brine. The aqueous phases were backextracted with 30 ml of methylene chloride. The organic layer was dried over sodium sulphate and concentrated completely. The solid residue was chromatographed on 300 g of silica gel using acetone/n-hexane (1:6, v/v) for the elution. Crystallization of the purified product from n-hexane afforded 2,2,2-trichloroethyl 3,5-dimethoxy-2,6-dimethylbenzoate as white crystals with mp 129° C.

(b) A solution of 2.73 g of 2,2,2-trichloroethyl 3,5-dimethoxy-2,6-dimethylbenzoate in 8 ml of methylene chloride was cooled to –78° C., whereupon the dissolved material partly precipitated. To the stirred mixture a solution of 6.01 g of boron tribromide in 8 ml of methylene chloride was added dropwise within 20 minutes. During the addition a clear solution formed, but later on a precipitate formed again. After stirring for 10 minutes at –78° C. and for 2.5 hours at 0° C., the reaction mixture was poured on ice water with stirring, and the aqueous layer was extracted with methylene chloride. The organic layer was washed with water, dried over sodium sulphate and evaporated to dryness in vacuo. The residue was chromatographed on silica gel using acetone/n-hexane (1:3, v/v) for the elution. Crystallization of the purified product from ethyl acetate/n-hexane afforded 2,2,2-trichloroethyl 3,5-dihydroxy-2,6-dimethylbenzoate as white crystals with mp 132°–133° C.

(c) A solution of 6.27 g of 2,2,2-trichloroethyl 3,5-dihydroxy-2,6-dimethylbenzoate in 15 ml of acetic anhydride and 0.3 ml of pyridine was heated under reflux for 3 hours. The solution was cooled and the solvent removed under reduced pressure. The residue was dissolved in 20 ml of ethyl acetate and crystallized by the addition of 120 ml of n-hexane to yield 2,2,2-trichloroethyl 3,5-diacetoxy-2,6-dimethylbenzoate as white crystals with mp 127°–128° C.

(d) A mixture of 4.76 g 2,2,2-trichloroethyl 3,5-diacetoxy-dimethylbenzoate and 2.24 g N-bromosuccinimide in 36 ml of carbontetrachloride was heated at reflux temperature and with light irradiation for 30 minutes. The mixture was cooled in an ice bath and insoluble material was removed by filtration. The filtrate was diluted with methylene chloride, washed with water, dried over sodium sulphate and evaporated in vacuo to provide crude 2,2,2-trichloroethyl 3,5-diacetoxy-2-bromomethyl-6-methylbenzoate, which was used directly without further purification.

(e) A suspension of 17.2 g of L-cysteine methyl ester hydrochloride and 20.5 g of N-(t-butoxycarbonyl)-L-serine in 300 ml of acetonitrile was treated at 0° C. with 10.1 g of 4-methylmorpholine. To the stirred solution was added dropwise at 10° C. within 30 minutes a solution of 20.6 g N,N-dicyclohexylcarbodiimide in 300 ml of acetonitrile. After stirring the reaction mixture for 3 hours at 0° C. the precipitate formed was filtered off, and the filtrate was evaporated in vacuo. The oily residue was dissolved in 200 ml of ethyl acetate and the solution washed consecutively with 0.5N hydrochloric acid, water, 5% aqueous sodium bicarbonate solution and brine. The organic layer was dried over sodium sulfate and evaporated in vacuo. The crude product was chromatographed on silica gel using ethyl acetate/n-hexane as eluent, and the so purified product was crystallized from diethyl ether/n-hexane to give N-[N-(t-butoxycarbonyl)-L-seryl]-L-cysteine methyl ester as white crystals with mp 72°–74° C.

(f) To a solution of 3.8 g 2,2,2-trichloroethyl 3,5-diacetoxy-2-bromomethyl-6-methylbenzoate and 2.9 g of N-[N-(t-butoxycarbonyl)-L-seryl]-L-cysteine methyl ester in 30 ml of methylene chloride was added dropwise at 0° C. within 15 minutes a solution of 0.91 g of triethylamine in 5 ml of methylene chloride. After stirring for 1 hour at 0° C. and for 1 hour of 20° C., the reaction mixture was diluted with methylene chloride and washed with 1N hydrochloric acid and with brine. The organic layer was dried over sodium sulfate and evaporated in vacuo. The remaining oil was chromatographed on silica gel using ethyl acetate/methylene chloride/n-hexane (1:1:1, v/v/v) as eluent. 2,2,2-Trichloroethyl 3,5-diacetoxy-6-[[[(CR)-2-[(S)-2-(1-t-butoxyformamido)-3-hydroxypropionamido]-2-(methoxycarbonyl)ethyl]thio]methyl]-2-methylbenzoate was obtained as an oil.

$^1$H-NMR (CDCl$_3$): δ1.46 (s,9H); 2.22 (s,3H); 2.33 (s,3H); 2.37 (s,3H); 2.78 (dd,J=14 Hz and 6 Hz,1H); 2.87–2.95 (m,1H); 2.94 (dd,J=14 Hz and 4 Hz,1H); 3.63–3.71 (m,1H); 3.73 (s,3H); 3.80 (s,2H); 4.05–4.17 (m,1H); 4.19–4.27 (m,1H); 4.74–4.81 (m,1H); 4.97 (d,J=11 Hz,1H); 5.04 (d,J=11 Hz,1H); 5.59 (d,J=7 Hz,1H); 7.01 (s,1H); 7.10 (d,J=7 Hz,1H) ppm.

(g) A mixture of 1.90 g of 2,2,2-trichloroethyl 3,5-diacetoxy-6-[[[(R)-2-[(S)-2-(1-t-butoxyformamido)-3-hydroxypropionamido]-2-(methoxycarbonyl)ethyl]thio]methyl]-2-methylbenzoate, 50 ml of tetrahydrofuran, 12.5 ml of 1M phosphoric acid, 12.5 ml of 1M aqueous sodium dihydrogen phosphate solution and 3.2 g of zinc powder was stirred at 20° C. for 1.2 hours. The mixture was filtered, and the unsoluble material was washed with water and ethyl acetate. The filtrate was partitioned between ethyl acetate and water. The organic layer was dried over sodium sulfate and evaporated in vacuo to afford 3,5-diacetoxy-6-[[[(R)-2-((S)-2-(1-t-butoxyformamido)-3-hydroxypropionamido]-2-(methoxycarbonyl)ethyl]thio]methyl]-2-methylbenzoic acid as a solidifying oil.

$^1$H-NMR (DMSO-$d_6$): δ1.38 (s,9H); 2.05 (s,3H); 2.30 (s,3H); 2.31 (s,3H); 2.74–2.96 (m,2H); 3.44–3.68 (m,2H); 3.62 (s,3H); 3.68 (s,2H); 3.98–4.12 (m,1H); 4.54 (dd,J=14 Hz and 8 Hz,1H); 6.71 (d,J=8 Hz,1H); 7.06 (s,1H); 8.27 (d,J=8 Hz,1H); 13.74 (broad s,1H) ppm

EXAMPLE 2

To a solution of 32 mg of t-butyl (4R,7S)-12,14-diacetoxy-1,3,4,5,6,7,8,10-octahydro-4-methoxycarbonyl-11-methyl-6,10-dioxo-9,2,5-benzoxathiaazacyclododecine-7-carbamate in 3 ml of methanol were added 15 mg of potassium carbonate. After stirring for 30 minutes at room temperature the reaction mixture was diluted with ethyl acetate and washed consecutively with 0.1M pH 7 aqueous sodium phosphate buffer and with brine. The organic layer was dried over sodium sulfate and evaporated in vacuo. The residue was purified by chromatography on silica gel using acetone/n-hexane 1:2 (v/v) as eluent. The purified product was dissolved in methylene chloride and precipitated by slow addition of n-hexane to yield t-butyl (4R,7S)-1,3,4,5,6,7,8,10-octahydro-12,14-dihydroxy-4-methoxycarbonyl-11-methyl-6,10-dioxo -9,2,5-benzoxathiaazacyclododecine-7-carbamate as a white, amorphous material.

$^1$H-NMR (CDCl$_3$): 1.50 (s,9H); 2.06 (s,3H); 2.93–3.25 (m,2H); 3.42 (d,J=12 Hz,1H); 3.76 (s,3H); 3.96 (d,J=12 Hz,1H); 4.32–4.44 (m,1H); 4.60–4.71 (m,1H); 4.84–4.95 (m1H); 5.17–5.30 (m,1H); 5.87 (d,J=8 Hz,1H); 6.02 (broad s,1H); 6.43 (s,1H); 6.65 (broad s,1H); 7.37 (d,J=8 Hz,1H) ppm

EXAMPLE 3

To a solution of 284 mg of t-butyl (4R,7S)-12,14-diacetoxy-1,3,4,5,6,7,8,10-octahydro-4-methoxycarbonyl-11-methyl-6,10-dioxo -9,2,5-benzoxathiaazacyclododecine-7-carbamate in 4.3 ml of tetrahydrofuran were added 1.4 ml of water. To the stirred mixture were added at room temperature within 1.5 hours 9 ml of 0.25N aqueous sodium hydroxide solution in such a manner that the pH of the mixture was kept between 11.8 and 12.1. Stirring was continued for 2 hours at pH 11.8. The reaction mixture was extracted with ethyl ether and the organic layer was back-extracted with 5% aqueous sodium bicarbonate solution. The combined aqueous solutions were acidified to pH 2 by the addition of 3N aqueous hydrochloric add and extracted with ethyl acetate. The ethyl acetate layer was washed with brine, dried over sodium sulfate and evaporated to dryness. The residue was crystallized from ethyl acetate/n-hexane to yield (4R,7S)-7-(L-t-butoxyformamido)-1,3,4,5,6,7,8,10-octahydro-12,14-dihydroxy-11-methyl-6,10-dioxo -9,2,5-benzoxathiaazacyclododecine-4-carboxylic acid as a white powder, mp 176° C. (decomposition).

$^1$H-NMR (DMSO-$d_6$): 1.41 (s,9H); 1.90 (s,3H); 2,90 (dd, J=15 Hz and 7.5 Hz,1H); 3.04 (dd,J=15 Hz and 5 Hz,1H); 3.28 (d,J=10 Hz.1H); 3.91 d,J=10 Hz,1H); 4.16 (dd.J=11 Hz and 3.5 Hz,1H); 4.24–4.37 (m,1H); 4.40–4.52 m,1H); 4.92 (dd,J=11 Hz and 3.5 Hz); 6.44 s,1H); 7.39 (d,J=7HZ, 1H); 7.90 d,J=8 Hz,1H); 9.48 (s,1H); 9.50 (s,1H); 3.04 (broad s,1H) ppm

EXAMPLE 4

A solution of 117 mg of (4R,7S)-7-(1-t-butoxyformamido)-1,3,4,5,6,7,8,10-octahydro-12,14-dihydroxy-11-methyl-6,10-dioxo-9,2,5-benzoxathiaazacyclododecine-4-carboxylic acid in 2.5 ml methylene chloride/trifluoroacetic acid (1:1, v/v) was stirred at 0° C. for 1.5 hours. Ice was added and the pH of the mixture was raised to 3 by the addition of 2N aqueous sodium hydroxide. The mixture was extracted with ethyl acetate and the organic layer back-extracted with water. The aqueous layer was concentrated in vacuo and the concentrated solution was chromatographed on MCI-Gel CHP20P (Mitsubishi Chemical Industries, Ltd.) using 1% aqueous acetic add as eluent. The product-containing fractions were combined and lyophilized to give (4R,7S)-7-amino-1,3,4,5,6,7,8,10-octahydro-12,14-dihydro-11methyl-6,10-dioxo-9,2,5-benzoxathiaazacyclododecine -4-carboxylic add as a white powder.

$^1$H-NMR (DMSO-$d_6$): δ1.88 (s,3H); 2.91 (dd,J=14 Hz and 8 Hz,1H); 3.07 (dd,J=14HZ and 6 Hz,1H); 3.26 (d,J=11 Hz,1H); 3.58–3.67 (m,1H); 3.87 (d,J-11 Hz,1H); 4.06 (dd.J=9 Hz and 2 Hz,1H); 4.36–4.45 (m,1H); 5.12 (dd,J=9 Hz and 1 Hz,1H); 6.43 (s,1H) ppm

EXAMPLE 5

A solution of 114 mg of t-butyl (4R,7S)-12,14-diacetoxy-1,3,4,5,6,7,8,10-octahydro-4-methoxycarbonyl-11-methyl-6,10-dioxo -9,2,5-benzoxathiaazacyclododecine-7-carbamate in 2.4 ml of trifluoroacetic acid was stirred at 0° C. for 30 minutes. The solution was poured onto a mixture of 20 ml of 0.5M aqueous sodium dihydrogenphosphate solution, 4.7 ml of 28% aqueous sodium hydroxide solution and crushed ice. The pH was adjusted to 9 by the addition of sodium hydroxide and the mixture was then extracted with methylene chloride. The organic layer was washed with brine, dried over sodium sulfate and evaporated in vacuo. The residue was dissolved in methylene chloride and crystallized by the addition of n-hexane to give methyl (4R,7S)-12,14-diacetoxy-7-amino-1,3,4,5,6,7,8,10-octahydro-11-methyl-6,10-dioxo-9,2,5-benzoxathiaazacyclododecine-4-carboxylate as a white powder.

$^1$H-NMR (DMSO-$d_6$): δ2.00 (s,3H); 2.30 (s,3H); 2.31 (s,3H); 2.96 (dd,J=15 Hz and 10 Hz,1H); 3.22 (dd,J=15 Hz and 5 Hz,1H); 3.39 (d,J=11 Hz,1H); 3.62–3.76 (m, 1H): 3.66 (s,3H); 3.88 (d,J=11 Hz,1H): 4.22 (dd,J=11 Hz and 3 Hz,1H); 4.62–4.76 (m,1H); 5.16 (dd,J=1 Hz and 2 Hz,1H); 7.11 (s,1H); 8.52 (d,J=8 Hz,1H) ppm

EXAMPLE 6

A solution of 14 mg of t-butyl (4R,7S)-1,3,4,5,6,7,8,10-octahydro-12,14-dihydroxy-4-methoxycarbonyl-11-methyl-6,10-dioxo-9,2,5-benzoxathiaazacyclododecine-7-carbamate in 0.3 ml of trifluoroacetic acid was stirred at 0° C. for 30 minutes. The solution was poured on ice, and the pH of the mixture was raised to 3.5 by the addition of 1N aqueous sodium hydroxide solution. The clear solution was chromatographed on MCI-Gel CHP20P using at first 0.1% aqueous acetic acid and then a mixture of 0.1% aqueous acetic acid/acetonitrile (9:1, v/v) as eluent. The fractions containing the product were lyophilized to give methyl (4R,7S)-7,amino-1,3,4,5,6,7,8,10-octahydro-12,14-dihydro-11-methyl-6,10-dioxo-9,2,5-benzoxathiaazacyclododecine-4-carboxylate as a white powder.

$^1$H-NMR (DMSO-d$_6$): δ1.87 (s,3H) superposed by 1.90 (broad s,2H); 2.85 (dd,J=15 Hz and 10 Hz,1H); 3.06 (dd,J=15 Hz and 4 Hz,1H); 3.39 (d,J=11 Hz,1H); 3.66 (s,3H); 3.82 (d,J11 Hz,1H); 4.09 (dd,J=11 Hz and 3 Hz,1H); 4.62 (m,1H); 5.11 (dd,J=11 Hz and 2 Hz,1H); 6.46 (s,1H); 8.45 (d,J=8HZ,1H); 9.55 (broad s,2H) ppm

EXAMPLE 7

3,5-Diacetoxy-6-[[[2-[(5)-2-(1-t-butoxyformamido)-3-hydroxypropionamido]-2-ethyl]thio]methyl]-2-methylbenzoic acid was lactonized in analogous manner to the procedure described in Example 1 to afford, upon chromatographic purification and crystallization from ethyl acetate/n-hexane, t-butyl (S)-12,14-diacetoxy-1,3,4,5,6,7,8,10-octahydro-11-methyl -6,10-dioxo-9,2,5-benzoxathiaazacyclododecine-7-carbamate as a white powder with mp 233° C. (dec.).

$^1$H-NMR (DMSO-d$_6$): δ1.39 (s,9H); 2.01 (s,3H); 2.30 (s,3H); 2.31 (s,3H): 2.54–2.86 (m,2H); 3.02–3.16 (m,1H); 3.50–3.74 (m,3H); 4.30–4.49 (m,2H); 4.56 4.68 (m,1H); 7.12 (s,1H); 7.17 (d,J=7 Hz,1H); 8.26–8.37 (m,1H) ppm The starting material used above was prepared as follows:

(a) 2,2,2-Trichloroethyl 3,5-diacetoxy-2-bromomethyl-6-methylbenzoate was reacted with t-butyl [(S)-2-hydroxy-1-[(2-mercaptoethyl)carbamoyl]ethyl]carbamate in a manner analogous to the procedure given in Example 1(f), and the resulting 2,2,2-trichloroethyl 3,5-diacetoxy-6-[[((R)-2-[(S)-2-(t-butoxyformamido)-3-hydroxypropionamido]-2-ethyl]thio]methyl]-2-methylbenzoate product was subjected in analogous manner to the procedure described in Example 1(g) to give 3,5-diacetoxy-6-[[[2-[(S)-2-(1-t-butoxyformamido)-3-hydroxypropionamido]-2-ethyl]thio]methyl]-2-methylbenzoic acid as an oil.

(b) t-Butyl [(S)-2-hydroxy-1-[(2-mercaptoethyl)carbamoyl]ethyl]carbamate was obtained from cysteamine hydrochloride and N-(t-butoxycarbonyl)-L-serine in a manner analogous to the procedure described in Example 1(e) as white crystals with mp 95°–96° C.

EXAMPLE 8

204 mg t-butyl (S)-12,14-diacetoxy-1,3,4,5,6,7,8,10-octahydro-11-methyl-6,10-dioxo-9,2,5-benzoxathiaazacyclododecine-7-carbamate was subjected to a procedure analogous to that described in Example 2. There was obtained, after crystallization from ethyl acetate/n-hexane, t-butyl (S)-1,3,4,5,6,7,8,10-octahydro-12,14-dihydroxy-11-methyl -6,10-dioxo-9,2,5-benzoxathiaazacyclododecine-7-carbamate as a white powder with mp 215° C. (decomposition).

$^1$H-NMR (DMSO-d$_6$): δ1.39 (s,9H); 1.89 (s,3H); 2.42–2.59 (m,1H); 2.65–2.80 (m,1H); 2.98–3.15 (m,1H); 3.48–3.74 (m,3H); 4.26–4.55 (m,3H); 6.44 (s,1H); 7.03 (d,J=6 Hz,1H); 8.20 (m,1H); 9.45 (s,1H); 9.49 (s,1H) ppm

EXAMPLE 9

64 mg t-butyl (S)-1,3,4,5,6,7,8,10-octahydro-12,14-dihydroxy-11-methyl-6,10-dioxo-9,2,5-benzoxathiaazacyclododecine-7-carbamate was subjected to a procedure analogous to that described in Example 6. There was obtained, after chromatographic purification and lyophilization, (S)-7-amino-4,5,7,8-tetrahydro-12,14-dihydroxy-11-methyl -9,2,5-benzoxathiaazacyclododecine-6,10(1H,3H)-dione as a white powder.

$^1$H-NMR (DMSO-d$_6$): δ1.87 (s,3H) superimposed with 1.80–2.00 (broad s,ca.4H); 2.42–2.80 (m,2H); 3.12–3.73 (overlapping m, ca. 8H); 4.09–4.26 (m,1H); 4.46–4.76 (m,1H); 6.42 (s,1H); 8.08 (broad s,1H) ppm

EXAMPLE 10

To a suspension of 47 mg of methyl (4R,7S)-12,14-diacetoxy-7-amino-1,3,4,5,6,7,8,10-octahydro-11-methyl-6,10-dioxo-9,2,5-benzoxathiaazacydododecine-4-carboxylate in 1 ml of acetonitrile were added 39 mg of S-(2-benzothiazolyl)-2-amino-4-thiazoleglyoxylate (Z)-O-methyloxime, and the mixture was stirred at 20° C. for 4 hours. The solvent was evaporated in vacuo, and the residue was chromatographed on silica gel using ethyl acetate/n-hexane (1:1, v/v) and ethyl acetate as eluent. The fractions containing the product were evaporated and the residue crystallized from methylene chloride/n-hexane,to give methyl (4R,7S)-12,14-diacetoxy-7-[(Z)-2-( 2-amino-4-thiazolyl)-2-(methoxyimino)acetamido]-1,3,4,5,6,7,8,10-octahydro-11-methyl-6,10-dioxo-9,2,5-benzoxathiaazacyclododecine -4carboxylate as a white powder.

$^1$H-NMR (DMSO-d$_6$): δ2.02 (s,3H); 2.31 (s,6H); 2.90 (dd, J=14 Hz and 9 Hz.1H); 3.24 (dd,J=14 Hz and 5 Hz,1H); 3.46 (d,J=12 Hz,1H); 3.65 (s,3H); 3.83 (d,J=12 Hz,1H); 3.84 (s,3H); 4.28 (dd,J=11 Hz and 4 Hz,1H); 4.52–4.61 (m,1H); 4.78–4.87 (m,1H); 5.12 (dd,J=11 Hz and 3 Hz,1H); 6.85 (s,1H); 7.13 (s,1H); 7.20 (broad s,2H); 8.10 (d,J=8 Hz,1H); 9.44 (d,J=8 Hz,1H) ppm

EXAMPLE 11

Methyl (4R,7S)-12,14-diacetoxy-7-[(Z)-2-(2-amino-4-thiazolyl)-2-(methoxyimino)acetamido]-1,3,4,5,6,7,8,10-octahydro-11-methyl-6,10-dioxo-9,2,5-benzoxathiaazacyclododecine -4-carboxylate, was subjected to a procedure analogous to that described in Example 2. There was obtained, after crystallization from ethyl acetate/n-hexane, methyl (4R,7S)-[(Z)-2-(2-amino-4-thiazolyl)-2-(methoxyimino)acetamido]-1,3,4, 5,6,7,8,10-octahydro-12,14-dihydroxy-11-methyl-6,10-dioxo-9,2,5-benzoxathiaazacyclododecine-4-carboxylate as a white powder.

$^1$H-NMR (DMSO-d$_6$): δ1.89 (s,3H); 2.78 (dd,J=14 Hz and 9 Hz,1H); 3.10 (dd,J=14 Hz and 4.Hz,1H); 3.92 (d,J=11 Hz,1H); 3.64 (s,3H); 3.82 (d,J=11 Hz,1H); 3.85 (s,3H); 4.15 (dd,J=11 Hz and 4 Hz,1H); 4.50–4.62 (m,1H); 4.68–4.76 (m,1H); 5.60 (dd,J=11 Hz and 3 Hz,1H); 6.44 (s,1H); 6.83 (s,1H); 7.16 (broad s,2H); 7.96 (d,J=8 Hz,1H); 9.38 (d,J=7 Hz,1H); 9.50 (s,1H); 9.51 (s,1H) ppm

EXAMPLE 12

Tank Fermentation

The culture producing compound Ia was grown and maintained on an agar slant having the following composition (grams/liter distilled water):

| | |
|---|---|
| Yeast extract | 4 |
| Malt extract | 10 |
| Glucose | 4 |
| Agar | 20.0 |
| (pH 7.3) | |

The slant was inoculated with the culture and incubated at 27° C. for 14 days. A chunk of the agar containing spores and mycelia from the sporulated culture slant was then used to inoculate a 500 ml Erlenmeyer flask containing 100 ml of sterilized inoculum medium (A24 medium) having the following composition (grams/liter distilled water):

| | |
|---|---|
| Glucose | 20.0 |
| Toast soya | 20.0 |
| Yeast extract | 5.0 |
| NaCl | 2.5 |
| $ZnSO_4 \cdot 7H_2O$ | 0.05 |
| $CuSO_4 \cdot 5H_2O$ | 0.005 |
| $MnCl_2 \cdot 4H_2O$ | 0.005 |
| (pH 7.0) | |

The inoculated inoculum medium was incubated at 27° C. for 3 days on a rotary shaker. A new 500 ml Eriemeyer flask containing 100 ml of the same medium was inoculated with 2% of the first-stage inoculum and incubated on a rotary shaker for 3 days at 27° C.

The production-stage was done in a 200 1-fermentor coning 140 liters of the same medium which was inoculated with 2% of the second-stage inoculum, and operated at 27° C., agitated at 250 rpm, and aerated at 140 liters/min with an inner pressure of 0.5 kg/cm². An antifoaming agent (Nissan disfoam) was added when there was a need. The broth was harvested afar 2 days.

Isolation

In the following isolation procedure, each fraction was monitored by DNA gyrase inhibition assay.

Harvested broth (140 liters) was separated to roycelia and filtrate.

Activated charcoal (1,100 g) was added to 110 liters of the filtrate. The mixture was stirred at room temperature for 30 minutes and then filtered. The carbon cake was then washed with water an suspended in 100 liters (50 liters×2) of 50% aqueous acetone. After stirring at 60° C. for 30 min, the mixture was filtered, and the filtrate was concentrated under reduced pressure.

The resulting brown syrup was dissolved in 500 ml of water and put on a column (10 liters)of Diaion HP-21 (Mitsubshi Chemical Industries, Tokyo) which was then eluted successively with water (20 liters) and 10% aqueous ethanol (50 liters). The active fractions eluted with 10% aqueous ethanol were pooled, the pooled sample was concentrated under reduced pressure and lyophilized to give 78,6 g of the residue as a yellow powder.

This lyophilized powder was then dissolved in 180 ml of water and put on an Amberlite CG-SO column (3.6 liters of a mixed bed consisting of one part of ammonium form and five parts of H⁺ form, type 1).

The active fractions (1.8 liters) eluted with water were combined and put on a column of 2.5 liters of DEAE-Toyopearl, coarse type (Toyosoda), which was first eluted with water (12 liters) and then with 0.02M NaCl (80 liters). The fractions eluted with 0.02M NaCl were monitored by High Pressure Liquid Chromatography. The active fractions were combined (30 liters) and put on a column of 2.5 liters of Diaion HP-21, and then eluted with water (5 liters) and after that with 50% aqueous acetone (15 liters). The active fractions eluted with 50% aqueous acetone were combined (10 liters) and concentrated to 100 ml under reduced pressure and partitioned between water and n-butyl alcohol. The aqueous layer was concentrated under reduced pressure and lyophilized to give crude compound Ia as a pale yellow powder.

This material (303 mg) was dissolved in water (3 ml) and applied onto a column of 1.5 liters of Toyopearl HW-40, super fine type (Toyosoda), and eluted with water. Lyophilisation of the active fractions gave compound Ia as a pale yellow amorphous powder, i.e. N-[[(4R,7S)-1,3,4,5,6,7 8,10-octahydro-12,14-dihydroxy-7-[[(3 R)-3-hydroxy-1-L-seryl-L-prolyl]amino]-11-methyl-6,10-dioxo-9,2,5-benzoxathiaazacyclododecin-4-yl]carbonyl]-L-alanine, probably in the form of its sodium salt.

The above is the correct chemical name.

The same compound was originally given the name of N-[[4R,7S-1,3,4,5,6,7 8,10-octahydro-12,14-dihydroxy-7-[(cis-3-hydroxy-1-S-seryl-prolyl)amino]- 11-methyl-6,10-dioxo-9,2,5-benzoxathiaazacyclododecin-4-yl ]carbonyl]-S-alanine.

Physicochemical Properties of Compound Ia

Compound Ia is an amphoteric, water soluble compound. The physicochemical properties of compound Ia are listed in Table 5.

The molecular formula of compound Ia was determined to be $C_{26}H_{35}N_5O_{12}S$. Mass spectral data showed a protonated molecular ion (MH⁺) m/z 642.2177 (calcd 642.2081); ¹H and ¹³C-NMR spectral data gave further evidence for this formula (Table 6).

TABLE 5

Physicochemical properties of compound Ia

| Appearance | pale yellow amorphous powder |
|---|---|
| $[\alpha]_D^{20}$ | −13.2 (c 1.0, $H_2O$) |
| $UV(H_2O)$ $\lambda max\ (\log \epsilon)_{nm}$ | 293 (3.20) |
| $UV(H_2O+NaOH)$ $\lambda max\ (\log \epsilon)_{nm}$ | 309 (3.30) |
| IR (KBr) $vmax\ cm^{-1}$ | 3350 (NH, OH), 1720 (ester C=O), 1640 (amide C=O) |
| HR-FAB-MS | Calcd: $C_{26}H_{36}N_5O_{12}S$ (MH+) 642.2081 Found: 642.2177 |
| Rf value | 0.17 on TLC (silica gel) Solvent system: n-BuOH-AcOH-$H_2O$ (4:1:2) |
| Colour reaction | ninhydrin (+), $FeCl_3$ (+) |

TABLE 6

¹H and ¹³C NMR chemical shifts and coupling constants for compound Ia in $D_2O$

| | Position No. | δC | δH | J(H,H) |
|---|---|---|---|---|
| Alanine moiety | 2 | 54.1 | 4.10(1H, q) | 7.3 Hz |
| | 2-CH₃ | 20.2 | 1.35(3H, d) | 7.3 Hz |
| | | 182.5 | — | |
| Cysteine moiety | 3 | 35.3 | 3.32(1H, d.d.) | 15, 4.6 Hz |
| | | | 2.66(1H, d.d.) | 15, 11.5 Hz |
| | 2 | 55.5 | 4.72(1H, m) | |
| | 1 | 173.4 a) | — | |
| Serine(I) moiety | 3 | 65.8 | 3.70(1H, d.d.) | 11.5, 5.5 Hz |
| | | | 3.58(1H, d.d.) | 11.5, 6.5 Hz |
| | 2 | 56.3 | 3.88(1H, d.d.) | 6.5, 5.5 Hz |
| | 1 | 173.4 a) | — | |
| Serine(II) moiety | 3 | 66.6 | 5.66(1H, d.d.) | 12, 2.4 Hz |
| | | | 4.36(1H, d.d.) | 12, 2.2 Hz |
| | 2 | 58.0 | 4.72(1H, m) | |
| | 1 | 174.1a) | — | |

TABLE 6-continued $^1$H and $^{13}$C NMR chemical shifts and coupling constants for compound Ia in $D_2O$

| | Position No. | δC | δH | J(H,H) |
|---|---|---|---|---|
| cis-3-Hydroxy- | 5 | 48.2 | 3.80(2H, m) | |
| proline | 4 | 35.3 | 2.22(1H, m) | |
| moiety | | | 2.05(1H, m) | |
| | 3 | 73.4 | 4.72(1H, m) | |
| | 2 | 66.6 | 4.72(1H, m) | |
| | 1 | 176.1 | | |
| Chromophore 1 | 1 | 137.5 | — | |
| moiety[b] | 2 | 117.0 | — | |
| | 3 | 159.2 | — | |
| | 4 | 108.8 | 6.43(1H, s) | |
| | 5 | 157.6 | — | |
| | 6 | 113.0 | — | |
| | 2-$CH_3$ | 14.7 | 1.98(3H, s) | |
| | 6-$CH_2$ | 30.4 | 3.86(3H, s) | 10.7 Hz |
| | | | 3.46(1H, d) | 10.7 Hz |
| | 1-C=O | 173.1 | — | |

[a] interchangeable
[b] Numbering of the chromophore:

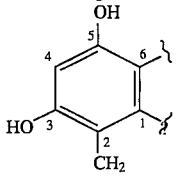

EXAMPLE 13

3,5-Bis (tert-butyldimethylsilyloxy)-6-[[[(R)-2-[(S)-1-tertbutoxyformamido)-3-hydroxypropionylamino]-2-methoxycarbonylethyl]thio]methyl]-2-methylbenzoic acid was lactonized in analogous manner to the procedure described in Example 1 to afford, upon chromatographic purification on silica gel using ethyl acetate/hexane (1: 3, v/v) as eluent, tert-butyl (4R, 7S)-12,14-bis (tert-butyldimethylsilyloxy)-1,3,4,5,6,7,8,10-octahydro-4-methoxycarbonyl-11-methyl-6,10-dioxo-9, 2,5-benzooxathiaazacyclododecine-7-carbamate as a pale yellow foam. To a solution of 21.4 g of this material in 300 ml of methanol were added 3.3 g of ammonium fluoride, and the mixture was stirred for 30 minutes at room temperature. The solvent was evaporated in vacuo. The residue chromatographed on silica gel using ethyl acetate/hexane (1:1, v/v) as eluent, and the purified product was crystallized from ethyl acetate/hexane to afford 11.0 g of tert-butyl (4R,7S)-1,3,4,5,6,7,8,10-octahydro-12,14-dihydroxy-4-methoxycarbonyl-11-methyl-6,10-dioxo-9, 2,5-benzoxathiaazacyclododecine-7-carbamate.

The starting material used above was prepared as follows:

(a) To a stirred mixture of 110 g of 37% aqueous formaldehyde, 250 ml of ethanol, and 250 ml of glacial acetic acid were added dropwise with cooling 126 g of 40% aqueous dimethylamine, keeping the temperature at −25°C. Stirring was continued for 30 minutes, whereupon the mixture was cooled to 10° C., and 200 g of 3,5-dihydroxy-2-methylbenzoic acid were added. The cooling bath was removed, and stirring was continued for 14 hours. The white precipitate formed was isolated by filtration, washed with water and dried to yield 150 g of α-(dimethylamino)-3,5-dihydroxy-2,6-dimethylbenzoic acid acetate as a white solid.

(b) A suspension of 150 g of α-(dimethylamino)-3,5-dihydroxy-2,6-dimethylbenzoic acid acetate in 1.5 l of methanol was treated with a suspension of 9 g of 5% palladium on charcoal in 220 ml of 3N aqueous sodium hydroxide, and the mixture was hydrogenated for 14 hours at a hydrogen pressure of 0.1 bar. The pH of the mixture was set to 1 by the addition of 37% hydrochloric acid, the catalyst was filtered off, and the filtrate was concentrated in vacuo. The residue was diluted with 0.5 l of water and then extracted with 1.2 l of ethyl acetate. The organic layer was washed successively with 2N hydrochloric acid and 15% sodium chloride solution, dried over sodium sulfate and evaporated in vacuo to give, after crystallization from dioxane, 87 g of 3, 5-dihydroxy-2,6-dimethylbenzoic acid as white crystals of m.p. 178°–179° C.

(c) To a solution of 91.1 g of 3,5-dihydroxy-2,6-dimethylbenzoic acid and 108.0 g of p-nitrobenzyl bromide were added 165.9 g of potassium carbonate. The mixture was heated at reflux under stirring for 4 hours. After cooling to room temperature, the mixture was filtered, and the unsoluble material was washed with 0.5 l of ethyl acetate. The filtrate was diluted with 0.5 l of ethyl acetate and washed with ice-cold 3N hydrochloric acid and with brine. The organic layer was dried over sodium sulfate and evaporated in vacuo. To the remaining, crystallizing oil were added 0.6 l of tert-butylmethylether, and the suspension was stirred for 1 hour. Unsoluble material was filtered off and the filtrate was evaporated in vacuo. The remaining oil was dissolved in 300 ml of methylene chloride. Upon crystallization, 200 ml of hexane were added and the crystals isolated by filtration. This material was suspended once more in 400 ml of tert-butylmethylether and the unsoluble material was removed by filtration. Evaporation of the filtrate in vacuo and crystallization of the residue from methylene chloride/hexane afforded 98.8 g of p-nitrobenzyl 3,5-dihydroxy-2,6-dimethylbenzoate as yellow crystals of m.p. 164°–166° C.

(d) To a mixture of 95.1 g of p-nitrobenzyl 3,5-dihydroxy-2,6-dimethylbenzoate and 99.6 g of tert-butyldimethylchlorosilane in 240 ml of dimethylformamide, cooled to 0° C., were added within 2 minutes 72.0 g of triethylamine, a precipitate resulting immediately. The mixture was stirred at 0° C. for 2 hours, then at room temperature for another 2 hours, and then diluted with 800 ml of ethyl acetate and washed 5 times with 400 ml of 15% sodium chloride solution. The aqueous phases were back-extracted with 800 ml of ethyl acetate. The organic phases were dried over sodium sulfate and evaporated in vacuo. Crystallization of the residual material from 1.2 l of hexane provided 141.8 g of p-nitrobenzyl 3,5-bis(tert-butyldimethylsilyloxy)-2,6-dimethylbenzoate as colourless crystals of m.p. 121°–122° C.

(e) p-Nitrobenzyl 3,5-bis(tert-butyldimethylsilyloxy)-2,6-dimethylbenzoate was subjected in an analogous manner to the procedures described in Example 1 (d) to afford p-nitrobenzyl 3,5-bis (tert-butyldimethylsilyloxy)-(α-bromo-2,6-xylate) which was subsequently reacted with N-[N-(tert-butoxy-carbonyl)-L-seryl]-L-cysteine methyl ester in an analogous manner to the procedure described in Example 1(f) to yield p-nitrobenzyl 3,5-bis (tert-butyldimethylsilyloxy)-6-[[[(R)-2-[(S)-(1-tertbutoxyformamido)-3-hydroxypropionylamino]-2-(methoxycarbonyl) ethyl]thio]methyl]-2-methylbenzoate.

¹H-NMR (250 MHz, CDCl₃): δ0.27(s,6H); 0.30(s,3H); 0.31(s,3H); 0.99(s,9H); 1.01(s,9H); 1.44(s,9H); 2.02(s, 3H); 2.87(dd, J=14 Hz and 6 Hz, 1H); 2.95 (dd, J=14 Hz and 5 Hz, 1H); 3.04 (m, 1H); 3.64–3.76 (m, 1H) superimposed by 3.70(s,3H), and by 3.74(d,J=12 Hz,1H); 3.79(d,J=12 Hz, 1H); 4.10(m, 1H); 4.27(broad s,1H); 4.71(m, 1H); 5.50(s,2H); 5.63 (broad d, J=8 Hz, 1H); 6.36 (s, 1H); 7.12 (broad d, J=8 Hz, 1H); 7.66 (d,J=8 Hz,2H); 8.24(d,J=8 Hz,2H) ppm (f) A mixture of 4.78 g of p-nitrobenzyl 3,5-bis(tert-butyldimethylsilyloxy)-6-[[[(R)-2-[(S)-(1-tert-butoxyformamido)-3-hydroxypropionylamino]-2-(methoxycarbonyl)ethyl]thio]methyl]-2-methylbenzoate and 1.43 g of 5% palladium on charcoal in 100 ml of ethyl acetate was hydrogenated for 1 hour at atmospheric pressure. The mixture was filtered, and the filtrate was washed successively with 50 ml of 1N hydrochloric acid and with 100 ml of brine. The organic layer was dried over sodium sulfate and evaporated in vacuo to afford 3.98 g of crude 3,5-bis (tert-butyldimethylsilyloxy)-6-[[[(R)-2-[(S)-1-tert-butoxyformamido )-3-hydroxypropionylamino]-2-(methoxycarbonyl)ethyl]thio]methyl]-2-methylbenzoic acid.

¹H-NMR (250 MHz, CDCl₃): δ0.20(s,6H); 0.25(s,6H); 1.00(s,9H); 1.02 (s, 9H); 1.50 (s, 9H); 2.17 (s, 3H); 2.90–3.15 (m, 2H); 3.6–4.9 (m, ~6H) superimposed by 3.77(s,3H); 6.43 (s, 3H); 7.58 (d, J=8 Hz, 1H) ppm

EXAMPLE 14

To a solution of 61 mg of methyl (4R, 7S)-7-amino-12,14-bis(tert-butyldimethylsilyloxy)-1,3,4,5,6,7,8,10-octahydro-11-methyl-6,10-dioxo-9,2,5-benzoxathiaazacyclododecine-4-carboxylate and 21 mg N-(tert-butoxycarbonyl)-L-serine in 2 ml of acetonitrile, cooled to 0° C., were added 20 mg of N-(dimethylaminopropyl)-N'-ethylcarbodiimide hydrochloride. The mixture was stirred at 0° C. for 4 hours, then diluted with 30 ml of ethyl acetate, and washed successively with 0.5N hydrochloric acid, water, 5% sodium bicarbonate solution, and with brine. The organic layer was dried over sodium sulfate and evaporated in vacuo. The residue was dissolved in 2 ml of methanol, 20 mg of ammonium fluoride were added, and the mixture was stirred for 30 minutes at room temperature. The mixture was diluted with 40 ml of ethyl acetate and washed with 30 ml of water. The organic layer was dried over sodium sulfate, and the solvent was evaporated in vacuo. The solid residue was triturated with 2 ml of ether, then hexane was added, and the white solid was isolated by filtration to give 22 mg of methyl (4R, 7S)-7-[(S)-2-(1-tert-butoxyformamido)-3-hydroxypropionylamino]-1,3,4,5,6,7,8,10-octahydro-12,14-dihydroxy-11-methyl-6,10-dioxo-9,2,5-benzoxathiaazacyclododecine-4-carboxylate.

¹H-NMR (250 MHz, DMSO-d₆): δ1.36(s,9H); 1.90(s,3H); 2.72(dd, J=14 Hz and 10 Hz, 1H); 3.08 (dd, J=14 Hz and 4 Hz, 1H); 3.44–3.72 (m, 2H) superimposed by 3.49 (d,J=10 Hz, 1H), and by 3.61(s,3H); 3.80(d,J=10 Hz, 1H); 4.06–4.28 (m, 2H); 4.52(m, 1H); 4.64(m, 1H); 5.25(t,J=5 Hz, 1H); 6.46(s, 1H); 6.83(d,J=8 Hz, 1H); 8.31(d,J=7 Hz,1H); 8.37 (d,J=9 Hz, 1H); 9.51 (s, 1H); 9.53 (s, 1H) ppm The starting material used above was prepared as follows:

(a) To 15 ml of trifluoroacetic acid, cooled to 0° C., were added 1.07 g of tert-butyl (4R, 7S)-12,14-bis (tert-butyldimethylsilyloxy)-1,3,4,5,6,7,8,10-octahydro-4-methoxycarbonyl11-methyl-6,10-dioxo-9,2,5-benzoxathiaazacyclododecine-7carbamate. The solution was stirred at 0° C. for 30 minutes, and then the solvent was evaporated in vacuo. The residue was dissolved in 50 ml of ethyl acetate, and the solution was washed successively with saturated sodium carbonate solution and with brine. The organic layer was dried over sodium sulfate and evaporated in vacuo. Crystallization of the residual material from hexane at –20° C. yielded 0.71 g of methyl (4R, 7S)-7-amino-12,14-bis-(tert-butyldimethylsilyloxy)-1,3,4,5,6,7,8,10-octahydro-11-methyl-6,10-dioxo-9,2,5-benzooxathiaazacyclododecine-4-carboxylate as white crystals of m.p. 135°–141° C. (dec.).

EXAMPLE 15 tert-Butyl (S)-12,14-bis (tert-butyldimethylsilyloxy)-1,3,4,5,6,7,8,10-octahydro-11-methyl-6,10-dioxo-9,2,5-benzooxathiaazacyclododecine-7-carbamate was subjected in an analogous manner to the procedures described in Example 14 to give tert-butyl [(S)-2-hydroxy-1-[[(S)-1,3,4,5,6,7,8,10-octahydro-12,14-dihydroxy- 11-methyl-6,10-dioxo-9,2,5-benzooxathiaazacyclododecin-7-yl]carbamoyl]ethyl]carbamate.

¹H-NMR (250 MHz, DMSO-d₆): δ1.37(s,9H); 1.89(s,3H); 2.54(m, 1H); 2.74(m, 1H); 3.13(m, 1H); 3.33(s,3H); 3.48–3.73(m, 4H); 4.09(m, 1H); 4.28(m, 1H); 4.94 (t, J=5 Hz, 1H); 6.44 (s, 1H); 6.84 (d, J=8 Hz, 1H); 8.06 (d, J=7 Hz, 1H); 8.25(m, 1H); 9.45(s,1H); 9.48(s,1H) ppm The starting material used above was prepared as follows:

(a) tert-Butyl (S)-1,3,4,5,6,7,8,10-octahydro-12,14-dihydroxy-11-methyl-6,10-dioxo-9,2,5-benzoxathiaazacyclododecine-7-carbamate was subjected in an analogous manner to the procedure described in Example 13 (d) to yield, after chromatographic purification, tert-butyl (S)-12,14-bis(tertbutyldimethylsilyloxy)-1,3,4,5,6,7,8,10-octahydro-11-methyl6,10-dioxo-9,2,5-benzoxathiaazacyclododecine-7-carbamate as a white-off solid.

EXAMPLE 16

(R)-3,5-bis (tert-butyldimethylsilyloxy)-2-[[[2-(3-hydroxypropionylamido)-2-(methoxycarbonyl)ethyl]thio]methyl]-6-methyl-benzoate was cyclized and the protection groups subsequently cleaved off in an analogous manner to the procedure described in Example 13 to yield, after chromatographic purification and cristallization from ethyl acetate/hexane, methyl (R)-1,3,4,5,6,7,8,10-octahydro-12,14-dihydroxy11-methyl-6,10-dioxo-9,2,5-benzoxathiaazacyclododecine-4-carboxylate as white solid.

¹H-NMR (400 MHz,DMSO-d₆): δ1.86(s,3H); 2.44(m, 1H); 2.59(dd, J=14 Hz and 11 Hz, 1H); 2.91 (m, 1H); 3.05(dd, J=14 Hz and 4 Hz, 1H); 3.65(s,3H); 3.67 (d, J=10 Hz, 1H); 3.71 (d, J=10 Hz, 1H); 4.51 (m, 1H); 4.59–4.70 (m, 2H); 6.42(s,1H); 8.55(d,J=8 Hz, 1H); 9.45(s, 1H); 9.49(s, 1H) ppm The starting material used above was prepared as follows:

(a) 2,2,2-Trichloroethyl 3,5-dihydroxy-2,6-dimethylbenzoate was subjected in an analogous manner to the procedure described in Example 13(d) to yield 2,2,2-trichloroethyl 3,5-bis (tert-butyldimethylsilyloxy)-2,6-dimethylbenzoate, m.p. 90°–92° C.

(b) 2,2,2-Trichloroethyl 3,5-bis (tert-butyldimethylsilyloxy)-2,6-dimethylbenzoate was subjected in an analogous manner to the procedure described in Example 1(d) to provide crude 2,2,2-trichloroethyl 2-bromomethyl-3,5-bis (tert-butyldimethylsilyloxy)-6-methylbenzoate which was used without further purification.

(c) To a solution of 76 g of 1,3-propanediol in 0.5 l of pyridine, cooled to 0° C., were added 278 g of trityl chloride. The mixture was stirred at room temperature for 18 hours, and then the solvent was evaporated in vacuo. The residue was taken up in 600 ml of ethyl acetate. Unsoluble material was filtered off, and the filtrate was washed with 100 ml portions of 3N hydrochloric acid, water, 5% sodium bicarbonate solution and brine. The organic layer was dried over sodium sulfate and evaporated in vacuo. Crystallization of the residual material from 0.5 l of ethyl acetate afforded 167.3 g of 3-trityloxy-1-propanol as white crystals of m.p. 117°–118° C.

(d) To a solution of 91.4 g of oxalyl chloride in 1.12 l of methylene chloride, pre-cooled to −70° C., a solution of 123.4 g of dimethylsulfoxide in 0.18 l of methylene chloride was added within 25 minutes. The solution was stirred for 10 minutes at −70° C. Then, a solution of 143.3 g of 3-trityloxy-1-propanol in 0.6 l of methylene chloride was added within 25 minutes, the temperature being maintained at −65° to −70° C. Stirring was continued for another 10 minutes, and then, 182 g of triethylamine were added within 5 minutes at −65° to −70° C. The mixture was stirred for 20 minutes at −70° C. and then allowed to warm up to 10° C. within 1 hour. After the addition of 1.2 l of water, stirring was continued for 5 minutes. The layers were separated, and the aqueous phase was extracted with 1.2 l of methylene chloride. The organic phases were washed with 1.2 l of water, dried over sodium sulfate, and the solvent was evaporated in vacuo. The residue was crystallized from ethyl acetate/hexane to yield 116.0 g of 3-trityloxypropionaldehyde as white crystals of m.p. 97°–98° C.

(e) To a stirred solution of 41.1 g of 3-trityloxy-propionaldehyde in 330 ml of acetone and 120 ml of water were added portionwise, within 90 minutes, 20.65 g of potassium permanganate, the temperature of the mixture being maintained at 20° to 25° C. Stirring was continued for 90 minutes, and then the pH of the mixture was set to 5 by addition of 13 ml of 3N hydrochloric acid. Within 40 minutes, there were added dropwise 200 ml of 38% sodium bisulfite solution at a temperature of 20° to 25° C. The pH was lowered to 2 by the addition of 60 ml of 3N hydrochloric acid, and subsequently the mixture was extracted with 1 l of ethyl acetate. The organic layer was washed with water, dried over sodium sulfate, and the solvent was evaporated in vacuo. The residue was crystallized from ethyl acetate/hexane to yield 35.5 g of 3-trityloxy-propionic acid as white solid of m.p. 159°–161° C.

(f) L-Cysteine methyl ester was acylated with 3-trityloxypropionic acid using in an analogous manner the procedure described in Example 1(e) to yield, after chromatographic purification and cristallization from methylene chloride/hexane, methyl (R)-2-(3-trityloxy-propionylamino)-3-mercaptopropionate as white crystals of m.p. 80°–85° C.

(g) Crude 2,2,2-trichloroethyl 2-bromomethyl-3,5-bis (tert-butyldimethylsilyloxy)-6-methylbenzoate, as obtained from step 16 (b) above, was reacted with methyl (R)-2-(3-trityloxypropionylamino)-3-mercapto-propionate in an analogous manner to the procedure described in Example 1(f) to yield 2,2,2-trichloroethyl (R)-3,5-bis (tert-butyldimethylsilyloxy)-6-methyl-2-[[[2-(3-trityloxypropionylamino)-2-methoxycarbonylethyl ]thio]methyl]-benzoate.

(h) A mixture of 6.85 g of 2,2,2-trichloroethyl (R)-3,5-bis (tert-butyldimethylsilyloxy)-6-methyl-2-[[[2-(3-trityloxypropionylamino)-2-(methoxycarbonyl)ethyl] thio] methyl]benzoate and 0.11 g of p-toluenesulfonic acid in 115 ml of methanol was stirred at 60° C. for 30 minutes. The mixture was cooled and the solvent was evaporated in vacuo. Chromatography of the residue on silica gel using ethyl acetate/methylene chloride/hexane (1:1:1, v/v/v) as eluent afforded 3.97 g of 2,2,2-trichloroethyl (R)-3,5-bis(tert-butyldimethylsilyloxy)2-[[[2-(3-hydroxypropionylamino)-2-(methoxycarbonyl)ethyl] thio]methyl]-6-methyl-benzoate as white-off solid.

(i) 2,2,2-Trichloroethyl (R)-3,5-bis(tert-butyldimethylsilyloxy)-2-[[[2-(3-hydroxypropionylamino)-2-(methoxycarbonyl) ethyl]thio]methyl]-6-methylbenzoate was subjected in an analogous manner to the procedure described in Example 1 (g) to yield crude (R)-3, 5-bis (tert-butyldimethylsilyloxy)-2-[[[2-(3-hydroxypropionylamino)-2-(methoxycarbonyl)ethyl]thio]methyl ]-6-methylbenzoic acid.

EXAMPLE 17

To a solution of 1.30 g of 3,5-bis(tert-butyldimethylsilyloxy)-6-[[[(R)-2-[(R)-(1-tert-butoxyformamido)-3-hydroxypropionylamino]-2-(methoxycarbonyl)ethyl]thio]methyl]-2-methylbenzoic acid and 0.69 g of triphenylphosphine in 42 ml of toluene, cooled to 0° C., was added within 1 hour a solution of 0.44 g of diethyl azodicarboxylate in 17 ml of toluene. The mixture was stirred for another 4 hours at 0° C., and then the solvent was evaporated in vacuo. The residue was taken up in ethyl acetate. Upon cooling in an ice-bath and addition of hexane, crystallization of triphenylphosphine-oxide and diethyl N,N'-hydrazinedicarboxylate occured. The mixture was filtered and the filtrate was evaporated in vacuo. The residue was chromatographed on silica gel using ethyl acetate/hexane (1: 1, v/v) as eluent to yield 0.36 g of tert-butyl (4R, 7R)-12, 14-bis (tert-butyldimethylsilyloxy)-1,3,4,5,6,7,8,10-octahydro-4-methoxycarbonyl-11-methyl-6,10-dioxo-9,2,5-benzoxathiaazacyclododecine-7-carbamate. To a solution of 71 mg of this material in 2 ml of methanol were added 20 mg of ammonium fluoride. The mixture was stirred for 1 hour at room temperature, then diluted with 30 ml of ethyl acetate and subsequently washed with 2 times 30 ml of water. The organic layer was dried over sodium sulfate, and the solvent was evaporated in vacuo. The residue was chromatographed on silica gel using ethyl acetate/hexane (2:1, v/v) as eluent, and the purified product was crystallized from ethyl acetate/hexane to afford 22 mg of tert-butyl (4R,7R)-1,3,4,5,6,7,8,10-octahydro-12, 14-dihydroxy-4-methoxycarbonyl-11-methyl-6,10-dioxo-9, 2,5-benzoxathiaazacyclododecine-7-carbamate as a white solid.

$[\alpha]_D = -62.4°$ (c=0.7, EtOAc)

The starting material used above was prepared as follows:

(a) L-Cysteine methyl ester hydrochloride was acylated with N-(tert-butoxycarbonyl)-D-serine by using in an analogous manner the procedure described in Example 1(e) to yield N-[N-(tert-butoxycarbonyl)-D-seryl]-L-cysteine methyl ester as white crystals of m.p. 105°–106° C.

(b) p-Nitrobenzyl 3,5-bis (tert-butyldimethylsilyloxy)-alphabromo-2,6-xylate was reacted with N-[N-(tert-butoxycarbonyl)-D-seryl]-L-cysteine methyl ester using in an analogous manner the procedure described in Example 1(f), and the resulting product was subjected in an analogous manner to the procedure described in Example 13 (f) to yield 3,5-bis(tert-butyldimethylsilyloxy)-6-[[[(R)-2-[(R)-(1-tert-butoxyformamido)-3-hydroxypropionylamino ]-2-(methoxycarbonyl)ethyl]thio]methyl]-2-methylbenzoate.

EXAMPLE 18

2,2,2-Trichloroethyl 3,5-bis (tert-butyldimethylsilyloxy)-2-methylbenzoate was subjected in an analogous manner to the reaction sequence described in Example 1(d,f,g), and the resulting product was cyclized in an analogous manner to the procedure described in Example 21 to yield tert-butyl (4R, 7S)-12,14-bis (tert-butyldimethylsilyloxy)-1,3,4,5,6,7,8,10-octahydro-4-methoxycarbonyl-6,10-dioxo-9,2,5-benzoxathiaazacyclododecine-7-carbamate as a white solid. This material was treated with ammonium fluoride in methanol in an analogous manner to the procedure described in Example 21 to yield, after crystallization from ethyl acetate/hexane, tert-butyl (4R, 7S)-1,3,4,5,6,7,8,10-octahydro-12,14-dihydroxy-4-methoxycarbonyl-6,10-dioxo-9,2,5-benzoxathiaazacyclo-dodecine-carbamate as a white solid.

$^1$H-NMR (250 MHz, DMSO-d$_6$): δ1.42 (s, 9H); 2.87 (dd, J=14 Hz and 11 Hz, 1H); 3.05 (dd, J=14 Hz and 4 Hz, 1H); 3.64 (s, 3H); 3.85 (d, J=10 Hz, 1H); 4.17–4.45 (m, 3H); 4.59–4.83(m,2H); 6.50(d,J=2.5 Hz, 1H); 6.71(d,J=2.5 Hz, 1H); 7.44 (d,J=8 Hz,1H); 8.29(d,J=8 Hz, 1H); 9.61(s,1H); 9.80(s, 1H) ppm The starting material used above was prepared as follows:

(a) To a solution of 57.0 g of 3,5-dihydroxy-2-methylbenzoic acid in 0.5 l of dimethylformamide were added 125 g of imidazole and 169 g of tert-butyldimethylchlorosilane, and the mixture was stirred for 24 hours at 60° C. After cooling, the mixture was poured into 2 l of ice-water and subsequently extracted twice with 2.5 l portions of hexane. The organic layer was washed with 2 l of 5% sodium bicarbonate solution and twice with 2 l of ice-cold water. The organic layer was dried over sodium sulfate, and the solvent was evaporated in vacuo. The residual oil was crystallized from methanol to give 130 g of tert-butyldimethylsilyl 3,5-bis(tert-butyldimethyl-silyloxy)-2-methylbenzoate as white crystals of m.p. 64° C.

(b) To a solution of 110 g of tert-butyldimethylsilyl 3,5-bis(tert-butyldimethylsilylyloxy)-2-methylbenzoate in 1 l of tetrahydrofuran were added 1.5 l of 65% aqueous acetic acid, and the mixture was stirred at room temperature for 2 hours. The solvent was evaporated in vacuo, the residue was taken up in 0.5 l of toluene, and the solvent was evaporated again in vacuo to give 85 g of crude 3,5-bis(tert-butyldimethylsilyloxy)-2-methylbenzoic acid. To a solution of this material in 0.5 l of methylene choride were added 36.0 g of 2,2,2-trichloroethanol and 0.3 g of 4-dimethylaminopyridine. The solution was cooled to 5° C., and then, a solution of 60 g of dicyclohexylcarbodiimide in 250 ml of methylene chloride was added dropwise within 45 minutes. The mixture was stirred for 1 hour, the temperature being allowed to raise to room temperature. The precipitated dicyclohexylurea was removed by filtration, the filtrate was evaporated in vacuo, and the residue was chromatographed on silicagel using hexane/ethyl acetate (50:1, v/v) as eluent to yield 96 g of 2,2,2-trichloroethyl 3,5-bis (tert-butyldimethylsilyloxy)-2-methyl-benzoate as an oil.

$^1$H-NMR (250 MHz, CDCl$_3$): δ0.20(s,3H); 0.22(s,3H); 0.98(s,9H); 1.02(s,9H); 2.39(s,3H); 4.92(s,2H); 6.53(d,J=2.5 Hz, 1H); 7.15(d,J=2.5 Hz, 1H) ppm

EXAMPLE 19 tert-Butyl (4R, 7S)-12,14-bis (tert-butyldimethylsilyloxy)-1,3,4,5,6,7,8,10-octahydro-4-methoxycarbonyl-11-propyl-6,10-dioxo-9,2,5-benzoxathiaazacyclododecine-7-carbamate was subjected in an analogous manner to the procedures described in Example 14 to yield methyl (4R, 7S)-7-[(S)-2-(1-tert-butoxyformamido)-3-hydroxypropionylamino]-1,3,4,5,6,7,8,10-octahydro-12,14-dihydroxy-11-propyl-6,10-dioxo-9,2,5-benzooxathiaazacyclododecine-4-carboxylate.

$^1$H-NMR (250 MHz, DMSO-d$_6$): δ0.84 (t,J=5 Hz ,3H); 1.32–1.50 (m, 2H) superimposed by 1.36 (s, 9H); 2.16–2.44 (m, 2H); 2.68 (dd, J=14 Hz and 11 Hz, 1H); 3.04 (dd, J=14 Hz and 4 Hz, 1H); 3.44–3.68(m,4H); 3.61(s,3H); 3.75 (d, J=10 Hz, 1H); 4.07(dd, J=12 Hz and 2 Hz, 1H); 4.19(m, 1H); 4.48 (m, 1H); 4.62(m, 1H); 5.24(dd, J=12 Hz and 2 Hz, 1H); 5.26 (t,J=5 Hz, 1H); 6.45(s, 1H); 6.82(d,J-8 Hz, 1H); 8.26(d,J=8 Hz, 1H); 8.37(d,J=9 Hz, 1H); 9.46(s,1H); 9,52(s, 1H) ppm The starting material used above was prepared as follows:

(a) To 168.2 g of 3,5-dihydroxy-2-methylbenzoic acid in 0.6 l of methanol were added 10 ml of 98% sulfuric acid, and the mixture was heated at reflux for 18 hours. The solution was cooled to room temperature and neutralized by the addition of about 30 ml of 28% sodium hydroxide solution. The solvent was evaporated in vacuo, and the residue was taken up in 0.7 l of ethyl acetate. The solution was washed successively with saturated sodium carbonate solution and brine, dried over sodium sulfate, and the solvent was evaporated in vacuo. The residue was crystallized from ethyl acetate/hexane to yield 162.9 g of methyl 3,5-dihydroxy-2-methylbenzoate, m.p. 136°–138° C.

(b) To a solution of 27.3 g of methyl 3,5-dihydroxy-2-methylbenzoate and 21.8 g of allyl bromide in 300 ml of dimethylformamide were added portionwise, within 30 minutes, 8.64 g of a 55% dispersion of sodium hydride in mineral oil, the temperature being held between 10° and 20° C. The mixture was stirred at room temperature for 3 hours, and then poured into ice-water. The pH was adjusted to about 3 by the addition of 3N hydrochloric acid, and the mixture was extracted with 600 ml of ethyl acetate. The organic layer was washed 5 times with 100 ml of water, dried over sodium sulfate, and the solvent was evaporated in vacuo. The residue was chromatographed on silica gel using ethyl acetate/methylene chloride/hexane (1:1:3, v/v/v) as eluent, and the purified products were crystallized from ethyl acetate/hexane to afford 4.1 g of methyl 3-allyloxy-5-hydroxy-2-methylbenzoate, m.p. 86°–88° C., and 5.61 g of methyl 5-allyloxy-3-hydroxy-2-methylbenzoate, m.p. 84°–87° C.

(c) Under an argon atmosphere, 3.74 g of methyl 3-allyloxy-5-hydroxy-2-methylbenzoate were heated to 180° C. for 1.5 hours The crude product was chromatographed on silica gel using acetone/hexane (1:4, v/v) as eluent, and the major product was crystallized from ethyl acetate/hexane to afford 2.76 g of methyl 2-allyl-3,5-dihydroxy-6-methylbenzoate as white crystals of m.p. 72°–95° C.

(d) A mixture of 4.67 g of methyl 2-allyl-3,5-dihydroxy-6-methylbenzoate and 0.23 g of 5% palladium on charcoal in 40 ml of ethyl acetate was hydrogenated for 2 hours at atmospheric pressure. The mixture was filtered and the filtrate evaporated in vacuo. Crystallization of the residue from ethyl acetate/hexane afforded 4.30 g of methyl 3,5-dihydroxy-2-methyl-6-propylbenzoate, m.p. 88°–91° C.

(e) To a solution of 4.61 g of methyl 3,5-dihydroxy-2-methyl-6-propylbenzoate in 20 ml of methylene chloride were added at 0° C. within 30 minutes 50 ml of a 1M solution of boron tribromide in methylene chloride. The mixture was stirred for 5 hours at room temperature and then diluted with 100 ml of ethyl acetate. The mixture was washed with water and with brine, and the organic layer was dried over sodium sulfate and evaporated in vacuo to yield crude 3,5-dihydroxy-2-methyl-6-propylbenzoic acid.

$^1$H-NMR (250 MHz, DMSO-$d_6$): δ0.85 (t,J=7 Hz,3H); 1.36–1.50(m,2H); 1.91(s,3H); 2.30–2.40 (m, 2H); 6.34(s, 1H); 9.05(s, 1H); 9.13(s, 1H); 12.70(broad s, 1H) ppm (f) A mixture of 5.0 g of 3,5-dihydroxy-2-methyl-6-propyl benzoic acid, 4.48 g of 2,2,2-trichloroethanol, and 0, 1 ml of 98% sulfuric acid in 40 ml of toluene was heated at reflux for 3 hours, water being constantly removed by a Dean-Stark trap. The mixture was cooled, diluted with 80 ml of ethyl acetate and washed with brine. The organic layer was dried over sodium sulfate, and the solvent was evaporated in vacuo. Chromatography of the residue on silica gel using acetone/hexane (1:6, v/v) as eluent afforded 7.1 g of 2,2,2-trichloroethyl 3,5-dihydroxy-2-methyl-6-propylbenzoate as an oil.

$^1$H-NMR (90 MHz, CDCl$_3$): δ0.90 (t, 7 Hz, 3H); 1.3–1.7 (m, 2H); 2.13 (s, 3H); 2.3–2.6 (m, 2H); 5.00 (s,2H); 5.70(s, 1H); 5.80(s, 1H); 6.33(s, 1H) ppm (g) 2,2, 2-Trichloroethyl 3,5-dihydroxy-2-methyl-6-propylbenzoate was subjected in an analogous manner to a reaction sequence described in Example 13 (d) and in Example 1 (d, f, g), and the resulting product was cyclized in an analogous manner to the procedure described in Example 1 to yield tert-butyl (4R, 7S)-12, 14-bis (tert-butyldimethylsilyloxy)-1,3,4,5,6,7,8,10-octahydro-4-methoxycarbonyl- 6,10-dioxo-11-propyl-9,2,5-benzoxathiaazacyclododecine-7-carbamate

EXAMPLE 20 tert-Butyl (4R,7S)-12,14-bis(tert-butyldimethylsilyloxy)-1,3,4,5,6,7,8,10-octahydro-4-methoxycarbonyl-11-methyl-6,10-dioxo-13-propyl-9,2,5-benzoxathiaazacyclododecine-7-carbamate was treated with ammonium fluoride in methanol in an analogous manner to the procedure described in Example 13 to yield tert-butyl (4R,7S)-1,3,4,5,6,7,8,10-octahydro-12,14-dihydroxy-4-methoxycarbonyl-11-methyl-6,10-dioxo-13-propyl-9,2,5-benzoxathiaazacyclododecine-7-carbamate as a white solid.

$^1$H-NMR (250 MHz, DMSO-$d_6$): δ0.89(t,J=6 Hz, 1H); 1.32–1.52(m, 2H) superimposed by 1.41 (s, 9H); 1.97 (s, 3H), 2.58 (m, 2H); 2.88 (dd, J-14 Hz and 10 Hz, 1H); 3.06 (dd, J=14 Hz and 4 Hz, 1H); 3.48 (d, J=11 Hz, 1H); 3.63 (s, 3H); 3.89 (d,J=11 Hz, 1H); 4.21(dd, J=12 Hz and 2 Hz, 1H); 4.36(m, 1H); 4.56 (m, 1H); 4.89 (dd, J=12 Hz and 2 Hz, 1H); 7.23 (d, J=8 Hz, 1H); 8.19 (d,J=8 Hz, 1H); 8.27 (s, 1H); 8.29(s, 1H) ppm The starting material used above was prepared as follows:

(a) To a solution of 18.22 g of 3,5-dihydroxy-2,6-dimethylbenzoic acid and 24.2 g of allyl bromide in 200 ml of dimethylformamide were added portionwise within 30 minutes 8.70 g of a 55% dispersion of sodium hydride in mineral oil, the temperature being held between 20° and 30° C. The mixture was stirred at 20° C. for 3 hours, then poured into 400 ml of ice-water, and the mixture was extracted with 400 ml of ethyl acetate. The organic layer was washed 4 times with 200 ml of water, dried over sodium sulfate, and the solvent was evaporated in vacuo. The residue was chromatographed on silica gel using acetone/hexane (1:6, v/v) as eluent to give 5.34 g of allyl 3-allyloxy-5-hydroxy-2,6-dimethylbenzoate as a coulourless oil.

$^1$H-NMR (250 MHz,CDCl$_3$): δ2.10(s,6H); 4.43–4.47(m, 2H); 4.70–4.90(m, 3H); 5.24–5.46 (m, 4H); 5.95–6.10 (m, 2H); 6.38 (s, 1H) ppm (b) Under an argon atmosphere, 5.06 g of allyl 3-allyloxy-5-hydroxy-2,6-dimethylbenzoate were heated to 185° C. for 2.5 hours to give 5.02 g of allyl 4-allyl-3,5-dihydroxy-2,6-dimethylbenzoate as an oil.

$^1$H-NMR (250 MHz, CDCl$_3$): δ2.11(s,6H); 3.46–3.50(m, 2H); 4.80–4.85(m, 2H); 4.94 (broad s,2H); 5.13–5.46(m, 4H); 5.88–6.11(m,2H) ppm (c) A solution of 5.00 g of allyl 4-allyl-3,5-dihydroxy-2, 6-dimethylbenzoate in 80 ml of ethyl acetate was cooled to 0° C., and then treated with 90 mg of palladium acetate and 332 mg of triethyl phosphite. After stirring for 5 minutes, 2.04 g of N-methylpyrrolidine were added, a precipitate being formed immediately. Stirring was continued at 0° C., and then, the mixture was partitioned between ethyl acetate and 1N hydrochloric acid. The organic layer was washed with brine, dried over sodium sulfate, and the solvent was evaporated in vacuo. The residual oil was dissolved in 50 ml of ethyl acetate, and the solution was hydrogenated at atmospheric pressure for 1 hour in the presence of 100 mg of 5% palladium on charcoal. The catalyst was filtered off, and the solvent was evaporated in vacuo to yield 3.36 g of 3,5-dihydroxy-2,6-dimethyl-4-propylbenzoic acid as a coulourless oil.

$^1$H-NMR (250 MHz, DMSO-$d_6$): δ0.90(t,J=7 Hz,3H); 1.35–1.50(m,2H); 2.00(s,6H); 2.52–2.59 (m, 2H); 7.96 (s, 2H); 12.85 (broad s, 1H) ppm (d) 3,5-Dihydroxy-2,6-dimethyl-4-propylbenzoic acid was subjected in an analogous manner to the procedure described in Example 19 (f) to yield 2,2,2-trichloroethyl 3,5-dihydroxy-2,6-dimethyl-4-propylbenzoate as an oil.

(e) 2,2,2-Trichloroethyl 3,5-dihydroxy-2,6-dimethyl-4-propylbenzoate was subjected in an analogous manner to a reaction sequence described in Example 13 (d) and in Example 1 (d, f,g), and the resulting product was cyclized in an analogous manner to the procedure described in Example 1 to yield tert-butyl (4R, 7S)-12, 14-bis (tert-butyldimethylsilyloxy)-1,3,4,5,6,7,8,10-octahydro-4-methoxycarbonyl-11-methyl-6,10-dioxo-13-propyl-9,2,5-benzoxathiaazacyclododecine-7-carbamate.

EXAMPLE 21

To a solution of 36.4 g of 6-[[[(R)-2-[(S)-2-(1-tert-butoxyformamido )-3-hydroxypropionylamino]-2-(methoxycarbonyl)ethyl]thio]methyl]-3-(tert-butyldimethylsilyloxy)-5-methoxy-2-methylbenzoic acid and 22.3 g of triphenylphosphine in 1.4 l of toluene was added at 0° C. within 10 minutes a solution of 15.1 g of diethyl azodicarboxylate in 300 ml of toluene. The mixture was stirred for 5 hours at 0° C., and then the solvent was evaporated in vacuo. To the residue were added 300 ml of methylene chloride, and the mixture was stirred at 0° C. for 15 minutes. The precipitate was filtered off, and the filtrate was evaporated in vacuo. Chromatography of the residue on silica gel using ethyl acetate/hexane (2:3, v/v) as eluent and crystallization of the purified product from ethyl acetate/hexane provided 19.4 g of tert-butyl (4R,7S)-14-(tertbutyldimethylsilyloxy)-1,3,4,5,6,7,8,10-octahydro-12-methoxy-4-methoxycarbonyl-11-methyl-6,10,-dioxo-9,2,5-benzoxathiaazacyclododecine-7-carbamate as white crystals of m.p. 157°–158° C. This material was treated with ammonium fluoride in methanol in an analogous manner to the procedure described in Example 13 to yield, after crystallization from ethyl acetate/hexane tert-butyl (4R, 7S)-1,3,4,5,6,7,8, 10-octahydro-14-hydroxy-12-methoxy-4-methoxycarbonyl-11-methyl-6,10-dioxo-9,2,5-benzoxathiaazacyclododecine-7-carbamate as a white solid.

$^1$H-NMR (400 MHz,DMSO-$d_6$): δ1.41 (s, 9H); 1.94 (s, 3H); 2.90 (dd, J=14 Hz and 10 Hz, 1H); 3.04 (dd, J=14 Hz and 4 Hz, 1H); 3.40 (d, J=11 Hz, 1H); 3.63 (s, 3H); 3.71(s,3H); 3.81(d,J=11 Hz, 1H); 4.22(m, 1H); 4.35(m, 1H); 4.86 (m, 1H); 6.53 (s, 1H); 7.27 (d, J=8 Hz, 1H); 8.15 (d, J=8 Hz, 1H); 9.73 (s, 1H) ppm The starting material used above was prepared as follows:

(a) To a solution of 31.7 g of p-nitrobenzyl 3,5-dihydroxy-2,6-dimethylbenzoate in 200 ml of acetone were added 16.6 g of potassium carbonate and 17.1 g of methyl iodide, and the mixture was heated at reflux for 15 hours. The reaction mixture was filtered, and the filter cake was washed with 200 ml of ethyl acetate. The filtrate was washed successively with 0.5N hydrochloric acid and with brine, dried over sodium sulfate, and the solvent was evaporated i n vacuo. The remaining oil was dissolved in 150 ml of dimethylformamide, and the solution was cooled to 0° C. After the addition of 18.1 g of tert-butyldimethylchlorosilane and 13.1 g of triethylamine, the mixture was stirred at 0° C. for 3 hours. The mixture was diluted with 300 ml of ethyl acetate and subsequently washed 5 times with 10 0 ml of water. The organic layer was dried over sodium sulfate, and the solvent was evaporated in vacuo. The remaining oil was chromatographed on silica gel using acetone/hexane (1:5, v/v) as eluent to yield, after crystallization from ethyl acetate/hexane, 14,5 g of p-nitrobenzyl 3,5-bis(tert-butyldimethylsilyloxy)-2,6-dimethylbenzoate and 13.8 g of p-nitrobenzyl 3-(tert-butyldimethylsilyloxy)-5-methoxy-2,6-dimethylbenzoate, m.p. 80°–81° C., as the major products.

(b) p-Nitrobenzyl 3-(tert-butyldimethylsilyloxy)-5-methoxy-2,6-dimethylbenzoate was subjected in an analogous manner to the procedures described in Example 1 (d, f) and 13 (f) to yield 6-[[[(R)-2-[(S)-2-(1-tert-butoxyformamido)-3-hydroxypropionylamino]-2-(methoxycarbonyl)ethyl]thio]methyl]-3-(tert-butyldimethylsilyloxy)-5-methoxy-2-methylbenzoic acid $^1$H-NMR (250Mz, CDCl$_3$): (inter alia) δ1.47 (broad s, ~10H); 2.17 (s, 3H); 2.90 (dd, 1H); 3.09(dd, 1H); 3.74(s, 3H); 3.76(s,3H); 4.17(dd, 1H); 4.64(m, 1H); 4.76(m, 1H); 5.73(d, 1H); 6.37(s, 1H); 7.26(s,1H); 7.41(d, 1H) ppm

EXAMPLE 22

(R)-5-(tert-Butyldimethylsilyloxy)-2-[[[2-(3-hydroxypropionylamino)-2-(methoxycarbonyl)ethyl]thio]methyl]-5-methoxy-6-methylbenzoic acid was cyclized and the protection groups were subsequently cleaved off in an analogous manner to the procedure described in Example 13 to yield, after chromatographic purification and cristallization from methanol/diethylether/hexane, methyl (R)-1,3,4, 5,6,7,8,10-octahydro-14-hydroxy-12-methoxy-11-methyl-6, 10-dioxo-9,2,5-benzoxathiaazacyclododecine-4-carboxylate as a white solid.

$^1$H-NMR (250 MHz, DMSO-$d_6$): δ1.90(s,3H); 2.44(m, 1H); 2.59(dd, 1H); 2.90(m, 1H); 3.07 (dd, 1H); 3.65(s,3H); 3.73(s,5H); 4.47–4.73(m,3H); 6.50 (s, 1H); 8.55(d, 1H); 9.67(s, 1H) ppm The starting material used above was prepared as follows:

(a) p-Nitrobenzyl 3-(tert-butyldimethylsilyloxy)-5-methoxy-2,6-dimethylbenzoate was subjected in an analogous manner to the procedures described in Example 1 (d), Example 16 (g, h), and in Example 13 (f) to yield (R)-5-(tert-butyldimethylsilyloxy)-[[[2-(3-hydroxypropionylamino)-2-(methoxycarbonyl)ethyl]thio]methyl]-5-methoxy-6-methylbenzoic acid.

EXAMPLE 23 p-Nitrobenzyl 3-(tert-butyldimethylsilyloxy)-5-methoxy-2-methyl-6-[[[(R)-2-[(S)-(4-nitrobenzyloxycarbonyloxy)-butyrylamino ]-2-(methoxycarbonyl)ethyl]thio]methyl]-benzoic acid was subjected in analogous manner to the hydrogenation procedure described in Example 13 (f), the raw product was cyclized, and subsequently the silyl groups were cleaved off in an analogous manner to the procedures described in Examples 21 and 13, to yield methyl (4R, 8R)-1,3,4,5,6,7,8,10-octahydro-14-hydroxy-12-methoxy-8, 11-dimethyl-6,10-dioxo-9,2,5-benzoxathiaazacyclododecine-4-carboxylate as a white solid.

$^1$H-NMR (400 MHz, DMSO-$d_6$): δ1.32(d,J=7 Hz,3H); 1.91(s,3H); 2.48(m, 1H); 2.62(dd, J=14 Hz and 11 Hz, 1H); 2.69 (dd, J=14 Hz and 12 Hz, 1H); 3.10 (d, J=14 Hz and 4.5 Hz, 1H); 3.50(d,J=11 Hz, 1H); 3.65(s,3H); 3.72(s, 3H); 3.99 (d, J=11 Hz, 1H); 4.70 (m, 1H); 5.70 (m, 1H); 6.50 (s, 1H); 8.45 (d,J=9 Hz, 1H); 9.69(s, 1H) ppm The starting material used above was prepared as follows:

(a) To a solution of 3.84 g of tert-butyl (S)-3-hydroxybutyrate and 5.86 g of 4-dimethylaminopyridine in 20 ml of methylene chloride was added at 0° C. within 20 minutes a solution of 6.47 g of p-nitrobenzyl chloroformate in 20 ml of methylene chloride. The mixture was stirred for 3 hours at 0° C., then diluted with 50 ml of methylene chloride and washed successively with 1N hydrochloric acid, saturated sodium bicarbonate solution, and with brine. The organic layer was dried over sodium sulfate, and the solvent was evaporated in vacuo. The residual oil was chromatographed on silica gel using ethyl acetate/hexane (1:1, v/v) as eluent to yield 5.10 g of tert-butyl (S)-3-(4-nitrobenzyloxycarbonyloxy)-butyrate as a colourless oil.

(b) A solution of 5.10 g of tert-butyl (S)-3-(4-nitrobenzyloxycarbonyloxy)-butyrate in 20 ml of trifluoroacetic acid was stirred at 0° C. for 90 minutes. The solvent was evaporated in vacuo, and the residue was crystallized from methylene chloride/hexane to yield 3.28 g of (S)-3-(4-nitrobenzyloxycarbonyloxy)-butyric acid as white crystals of m.p. 78°–81° C.

(c) To 2.83 g of (S)-3-(4-nitrobenzyloxycarbonyloxy)-butyric acid and 1.72 g of N-hydroxy-succinimide in 50 ml of acetonitrile were added 2.88 g of N-(dimethylaminopropyl)-N'-ethylcarbodiimide hydrochloride. The mixture was stirred at 0° C. for 3 hours. Then, 2.58 g of L-cysteine methyl ester hydrochloride and 1.52 g of 4-methylmorpholine were added, and stirring was continued for another 3 hours at 0° C. The solvent was evaporated in vacuo, the residue was taken up in 150 ml of ethyl acetate, and the solution was washed successively with 1N hydrochloric acid, saturated sodium bicarbonate solution, and with saturated sodium chloride solution. The organic layer was dried over sodium sulfate, and the solvent was evaporated in vacuo. The remaining oil was chromatographed on silica gel using ethyl acetate/hexane (1:1, v/v) as eluent. Crystallization of the purified product from methylene chloride/hexane provided methyl (R)-2-[(S)-(4-nitrobenzyloxycarbonyloxy)butylamino]-3-mercapto-propionate as a white solid.

$^1$H-NMR (250 MHz, CDCl$_3$): δ1.36 (m, 1H); 1.41 (d, J=6 Hz, 3H); 2.60 (ddd, J=14 Hz, 8 Hz and 5 Hz, 2H); 3.01(dd, J=9 Hz and 4 Hz,2H); 3.79(s,3H); 4.87(m, 1H); 5.14–5.32(m, 3H); 6.51(d,J=7 Hz, 1H); 7.55(d,J=8 Hz,2H); 8.23 (d,J=8 Hz, 2H) ppm (d) p-Nitrobenzyl 3-(tert-butyldimethylsilyloxy)-5-methoxy-2,6-dimethylbenzoate was subjected in an analogous manner to the procedures described in Example 1 (d) to give a product mixture containing p-nitrobenzyl 2-bromomethyl-3-(tert-butyldimethyl-silyloxy)-5-methoxy-6-methylbenzoate.

(e) Crude p-nitrobenzyl 2-bromomethyl-3-(tert-butyldimethylsilyloxy)-5-methoxy-6-methylbenzoate, as obtained in step (d), was reacted with methyl (R)-2-[(S)-(4-nitrobenzyloxycarbonyloxy)-butyrylamino]-3-mercapto-propionate in an analogous manner to the procedure described in Example 1 (f) to yield p-nitrobenzyl-3-(tert-butyldimethylsilyloxy)-5-methoxy-2-methyl-6-[[[(R)-2-[(S)-(4-nitrobenzyloxycarbonyloxy)-butyrylamino]-2-(methoxy-carbonyl)ethyl]thio] methyl]-benzoic acid

EXAMPLE 24

Crude p-nitrobenzyl 2-bromomethyl-3-(tert-butyldimethylsilyloxy)-5-methoxy-6-methylbenzoate, as obtained in Example 23 (d), was reacted with N-[N-(tert-butoxycarbonyl)-D-seryl]-L-cysteine methyl ester in an analogous manner to the procedure described in Example 1 (f), and the product was subjected in an analogous manner to the sequence of procedures used in Example 23 to yield tert-butyl (4R, 7R)-1,3,4,5,6,7,8,10-octa-hydro-14-hydroxy-12-methoxy-4-methoxycarbonyl-11-methyl-6,10-dioxo-9,2,5-benzoxathiaazacyclododecine-7-carbamate as a white solid.

$^1$H-NMR (250 MHz, DMSO-d$_6$): δ1.40 (s, 9H); 1.91 (s, 3H); 2.59(dd, J=14 Hz and 11 Hz, 1H); 3.05 (dd, J=14 Hz and 4 Hz, 1H); 3.64 (d, J=10 Hz, 1H); 3.65 (s, 3H); 3.72 (s,3H); 3.80(d,J=10 Hz, 1H); 4.32–4.50(m, 1H); 4.54–4.72(m, 1H); 6.49(s,1H); 7.07(d,J=8 Hz, 1H); 8.79(d,J=8 Hz, 1H); 9.70(s, 1H) ppm

EXAMPLE 25

Crude p-nitrobenzyl 2-bromomethyl-3-(tert-butyldimethylsilyloxy)-5-methoxy-6-methylbenzoate, as obtained in Example 23(d), was reacted with N-[N-(tert-butoxycarbonyl)-D-threonyl]-L-cysteine methyl ester in an analogous manner to the procedure described in Example 1 (f), and the product was subjected in an analogous manner to a sequence of procedures described in Example 23 to yield t-butyl (4R,7R, 8R)-1,3,4,5,6,7,8,10-octahydro-14-hydroxy-12-methoxy-4-methoxycarbonyl-8,11-dimethyl-6,10-dioxo-9, 2,5-benzoxathiaazacyclododecine-7-carbamate as a white solid.

$^1$H-NMR (250 MHz, DMSO-d$_6$): δ1.26 (d, 3H); 1.39 (s, 9H); 1.92 (s, 3H); 2.51 (dd, 1H); 3.05 (dd, 1H); 3.28 (d, 1H); 3.64 (s, 3H); 3.72 (s, 3H); 4.03 (d, 1H); 4.30 (dd, 1H); 4.65 (m, 1H); 5.33 (m, 1H); 6.50 (s, 1H); 7.23 (d, 1H); 8.68 (d, 1H); 9.69 (s, 1H) ppm The starting material used above was prepared as follows:

(a) L-Cysteine methyl ester was acylated with N-(tert-butoxycarbonyl)-D-threonine by using in an analogous manner the procedure described in Example 1(e) to yield after chromatographic purification and crystallization from diethylether/hexane N-[N-(tert-butoxycarbonyl)-D-threonyl]-L-cysteine methyl ester as white crystals of m.p. 98°–100° C.

EXAMPLE 26

Crude p-nitrobenzyl 2-bromomethyl-3-(tert-butyldimethylsilyloxy)-5-methoxy-6-methylbenzoate, as obtained in Example 23(d), was reacted with methyl (R)-2-(2,2-dimethyl-3-trityloxypropionyiamino)-3-mercapto-propionate in an analogous manner to the procedure described in Example 1 (f), and the product was subjected in an analogous manner to a sequence of procedures described in Example 16(h), 13(f) and 21 to yield tert-butyl (R)-1,3,4,5,6,7,8,10-octahydro-14-hydroxy-12-methoxy-4-methoxycarbonyl-7,7,11-trimethyl-6,10-dioxo-9,2,5-benzooxathiaazacyclododecine-7-carbamate as a white solid.

$^1$H-NMR (250 MHz, DMSO-d$_6$): δ1.15(s,3H); 1.24(s,3H); 1.92 (s,3H); 2.72(dd, J=14 Hz and 12 Hz, 1H); 4.14 (dd, J=14 Hz and 4.5 Hz, 1H); 3.5–3.7 (m, 2H) superimposed by 3.64 (s, 3H); 3.72 (s, 3H); 4.36 (d, J=11 Hz, 1H); 4.44(d,J=11 Hz, 1H); 4.56(m, 1H); 6.49(s,1H); 8.12(d, 8 Hz, 1H); 9.70 (s, 1H) ppm The starting material used above was prepared as follows:

(a) To a solution of 25.0 g of methyl 3-hydroxy-2,2-dimethylpropanoate in 100 ml of pyridine, cooled to 0° C., were added 55.7 g of trityl chloride. The mixture was stirred at room temperature for 20 hours, and then the solvent was evaporated in vacuo. The residue was taken up in 200 ml of ethyl acetate, and the solution was washed successively with water, 1N hydrochloric acid, water, saturated sodium bicarbonate solution and brine. The organic layer was dried over sodium sulfate, and the solvent was evaporated in vacuo. The residual oil was taken up in 50 ml of methylene chloride, and to the solution were added slowly, at 0° C., 300 ml of hexane. Trityl alcohol crystallized and was filtered off. The filtrate was evaporated in vacuo to yield 53.5 g of raw methyl 2,2-dimethyl-3-trityloxy-propionate.

(b) A solution of 53.5 g of raw methyl 2,2-dimethyl-3-trityloxy-propionate and 16.8 g of potassium hydroxide in 100 ml of ethylene glycol was heated to 160° C. for 4 hours. The mixture was cooled, diluted with 400 ml of ethyl acetate, and then washed successively with ice-cold 1N hydrochloric acid and with brine. The organic layer was dried over sodium sulfate, and the solvent was evaporated in vacuo. The residue was triturated with diethylether, unsoluble material was filtered off, and the filtrate was evaporated. Crystallization of the residue from diethylether/hexane provided 7.5 g of 2,2-dimethyl-3-trityloxy-propanoic acid, m.p. 153°–158° C.

$^1$H-NMR(90 MHz,CDCl$_3$): δ1.23 (s, 6H); 3.17(s,2H); 7.2–7.7(m, 15H) ppm (c) L-Cysteine methyl ester was acylated with 2,2-dimethyl-3-trityloxy-propanoic acid in an analogous manner to the procedure described in Example 1 (e) to yield after chromatographic purification methyl (R)-2-(2,2-dimethyl-3-trityloxypropionylamino)-3-mercapto-propionate as an oil.

$^1$H-NMR(250 MHz,CDCl$_3$): δ1.20(s,3H); 1.24(s,3H); 2.93(m,2H); 3.16(s,2H); 3.68(s,3H); 4.86 (m, 1H); 7.2–7.6 (m, 15H) ppm

EXAMPLE 27

3-(tert-Butyldimethylsilyloxy)-6-[[[(R)-2-(1-tert-butoxyformamido)-5-ethoxy-3-hydroxypropionylamino]-2-(methoxycarbonyl)ethyl]thio]methyl]-2-methylbenzoic acid was subjected in an analogous manner to the cyclization procedure described in Example 21 to yield, after crystallization from hexane, tert-butyl (4R, 7S)-14-(tert-butyldimethylsilyloxy)-1,3,4,5,6,7,8,10-octahydro-12-ethoxy-4-methoxycarbonyl-11-methyl-6,10-dioxo-9,2,5-benzoxathiaazacyclododecine-7-carbamate as white crystals. This material was treated with ammonium fluoride in methanol in an analogous manner to the procedure described in Example 13 to yield, after crystallization from ethyl acetate/hexane, tert-butyl (4R, 7S)-1,3,4,5,6,7,8,10-octahydro-14-hydroxy-12-ethoxy-4-methoxycarbonyl-11-methyl-6,10-dioxo-9,2,5-benzoxathiaazacyclododecine-7-carbamate as a white solid.

$^1$H-NMR(250 MHz, DMSO-d$_6$): 1.32(t,J=7 Hz,3H); 1.41(s, 9H); 1.93(s,3H); 2.84(dd, J=14 Hz and 10 Hz, 1H); 3.05 (dd, J=14 Hz and 4 Hz, 1H); 3.45 (d, J=10 Hz, 1H); 3.63 (s,3H); 3.84 (d,J=10 Hz, 1H); 3.94 (q,J=7 Hz,2H); 4.21(dd, J=11 Hz and 3 Hz,1H); 4.35(m, 1H); 4.53(m, 1H); 4.89(dd, J=11 Hz and 2 Hz, 1H); 6.49(s, 1H); 7.20 (d, J=8 Hz, 1H); 8.16 (d, J=8 Hz, 1H); 9.68 (s, 1H) ppm The starting material used above was prepared as follows:

(a) p-Nitrobenzyl 3,5-dihydroxy-2,6-dimethylbenzoate was subjected in an analogous manner to the procedure described in Example 21(a), using ethyl bromide instead of methyl iodide, to yield after crystallization from hexane, p-nitrobenzyl 3-(tert-butyldimethylsilyloxy)-5-ethoxy-2,6-dimethylbenzoate as white crystals, m.p.75°–76° C.

(b) p-Nitrobenzyl 3-(tert-butyldimethylsilyloxy)-5-ethoxy-2,6-dimethylbenzoate was subjected in an analogous manner to the procedures described in Example 1(d,f) and 13(f) to yield 3-(tert-butyldimethylsilyloxy)-6-[[[(R)-2-(1-tert-butoxyformamido)-5-ethoxy-3-hydroxypropionylamino]-2-(methoxycarbonyl)ethyl]thio]methyl]-2-methylbenzoic acid.

EXAMPLE 28 p-Nitrobenzyl 2-bromomethyl-3-(tert-butyldimethylsilyloxy)-5-methoxybenzoate was subjected in an analogous manner to a sequence of procedures described in Example 1(f) and 13(f), and the product was cyclized in in analogous manner to the procedure described in Example 21 to yield tert-butyl (4R, 7S)-14-(tert-butyldimethylsilyloxy)-1,3,4,5,6,7,8,10-octahydro-12-methoxy-4-methoxycarbony 1-6,10-dioxo-9,2,5-benzoxathiaazacyclododecine-7-carbamate as white crystals. This material was treated with ammonium fluoride in methanol in an analogous manner to the procedure described in Example 13 to yield, after crystallization from methanol/ethyl acetate/hexane, tert-butyl (4R, 7S)-1,3,4,5,6,7,8,10-octahydro-14-hydroxy-12-methoxy-4-methoxycarbonyl-6,10-dioxo-9,2,5-benzoxathiaazacyclododecine-7-carbamate as a white solid.

$^1$H-NMR(250 MHz, DMSO-d$_6$): δ1.42 (s, 9H); 2.88 (dd, 1H); 3.05 (dd, 1H).;3.64 (s,3H); 3.71 (s,3H); 3.86 (d, 1H); 4.20–4.45 (m, 3H); 4.55–4.83 (m, 2H); 6.60 (d, 1H); 6.79 (d, 1H); 7.42 (d, 1H); 8.28 (d, 1H) ppm The starting material used above was prepared as follows:

(a) 3,5-Dihydroxy-2-methylbenzoic acid was subjected in an analogous manner to the procedure described in Example 13(b) to yield p-nitrobenzyl 3,5-dihydroxy-2-methylbenzoate as pale yellow crystals of m.p. 160°–163° C.

(b) p-Nitrobenzyl 3,5-dihydroxy-2-methylbenzoate was subjected in an analogous manner to the procedure described in Example 21 (a) to yield, after chromatographic purification and crystallization from hexane, p-nitrobenzyl 3-(tert-butyldimethylsilyloxy)-5-methoxy-2-methylbenzoate as white crystals of m.p. 83°–85° C.

(c) p-Nitrobenzyl 3-(tert-butyldimethylsilyloxy)-5-methoxy-2-methylbenzoate was subjected in an analogous manner to the procedure described in Example 1(d) to yield, after crystallization from ethyl acetate/hexane, p-nitrobenzyl 2-bromomethyl-3-(tert-butyldimethylsilyloxy)-5-methoxybenzoate as white crystals of m.p. 82°–84° C.

EXAMPLE 29 p-Nitrobenzyl 2-bromomethyl-3-(tert-butyldimethylsilyloxy)-5-methoxybenzoate was reacted with N-[N-(tert-butoxycarbonyl)-D-threonyl]-L-cysteine methyl ester in an analogous manner to the procedure described in Example 1 (f), and the product was subjected in-an analogous manner to a sequence of procedures described in Example 13 (f) and in Example 21 to yield tert-butyl (4R, 7R, 8R)-14-(tert-butyldimethylsilyloxy)-1,3,4,5,6, 7,8,10-octahydro-12-methoxy-4-methoxycarbonyl-8-methyl-6,10-dioxo-9,2,5-benzoxathiaazacyclododecine-7-carbamate as white crystals. This material was treated with ammonium fluoride in methanol in an analogous manner to the procedure described in Example 13 to yield, after crystallization from methanol/diethylether/hexane, tert-butyl (4R, 7R, 8R)-1,3, 4,5,6,7,8,10-octahydro- 14-hydroxy-12-methoxy-4-methoxycarbonyl-8-methyl-6,10-dioxo-9,2,5-benzoxathiaazacyclododecine-7-carbamate as a white solid.

$^1$H-NMR (250 MHz, DMSO-d$_6$): δ1.21(d,3H); 1.40(s, 9H); 2.61(dd, 1H); 2.90(dd, 1H); 3.66(s,3H); 3.71 (s, 3H); 3.82 (d, 1H); 4.41 (dd, 1H); 4.60 (d 1H); 4.79 (m, 1H); 5.32 (m, 1H); 6.58 (d, 1H); 6.71 (d, 1H); 7,28 (d, 1H); 9.08 (d, 1H); 10.04 (s, 1H) ppm

EXAMPLE 30 p-Nitrobenzyl 2-bromomethyl-3-(tert-butyldimethylsilyloxy)-5-methoxybenzoate was reacted with N-[N-(tert-butoxycarbonyl)-D-seryl]-L-cysteine methyl ester in an analogous manner to the procedure described in Example 1 (f), and the product was subjected in an analogous manner to a sequence of procedures described in Example 13 (f) and,in Example 21 to yield tert-butyl (4R, 7R)-14-(tert-butyldimethylsilyloxy)-1,3,4,5,6,7 8,10-octahydro-12-methoxy-4-methoxycarbonyl-6,10-dioxo-9,2,5-benzoxathiaazacyclododecine-7-carbamate as white crystals. This material was treated with ammonium fluoride in methanol in an analogous manner to the procedure described in Example 13 to yield, after crystallization from diethylether/hexane, tert-butyl (4R, 7R)-1,3,4,5,6,7,8,10-octahydro-14-hydroxy-12-methoxy-4-methoxycarbonyl-6,10-dioxo-9,2,5-benzoxathiaazacyclo-dodecine-7-carbamate as a white solid.

$^1$H-NMR(250 MHz, DMSO-d$_6$): δ1.39(s,9H); 2.64(dd, J=14 Hz and 11 Hz, 1H); 3.06(dd, J=14 Hz and 4 Hz, 1H); 3.67(s,3H); 3.71(s,3H); 3.81(d,J=12 Hz, 1H); 4.22 (m, 1H); 4.33 (d, J=12 Hz, 1H); 4.48 (m, 1H); 4.56 (m, 1H); 4.73(m, 1H); 6.61(d,J=2 Hz,1H); 6.74(d,J=2 Hz, 1H); 7.14(d,J=8 Hz,1H); 9.02 (d, J=9 Hz, 1H); 10.11 (s, 1H) ppm

EXAMPLE 31 p-Nitrobenzyl 2-bromomethyl-3-(tert-butyldimethylsilyloxy)-5-methoxybenzoate was subjected in an analogous manner to a sequence of procedures described in Example 16(g,h), Example 13(f), and in Example 21 to yield methyl (4R)-14-(tert-butyldimethylsilyloxy)-1,3,4,5,6,7,8,10-octahydro-12-methoxy-6,10-dioxo-9,2,5-benzoxathiaazacyclododecine-4-carboxylate. This material was treated with ammonium fluoride in methanol in an analogous manner to the procedure described in Example 13 to yield, after crystallization from acetone/hexane, methyl (R)-1,3,4,5,6,7,8,10-octahydro-14-hydroxy-12-methoxy-6,10-dioxo-9,2,5-benzoxathiaazacyclododecine-4-carboxylate as a white solid.

$^1$H-NMR(250 MHz, DMSO-d$_6$): δ2.50 (m, partially obscured, 1H); 2.65 (dd, 1H); 2.81 (m, 1H); 3.06 (dd, 1H); 3.66 (s, 3H); 3.71 (s, 3H); 3.86 (d, 1H); 4.35 (m, 2H); 4.74 (m, 2H); 6.60 (d, 1H); 6.74 (d, 1H); 8.74 (d, 1H); 10.03 (s, 1H) ppm

EXAMPLE 32 p-Nitrobenzyl 2-bromomethyl-3-(tert-butyldimethylsilyloxy)-5-methoxybenzoate was reacted with methyl (R)-2-[(R)-3-hydroxy-3-methoxycarbonyl-propionylamino]-3-mercapto-propionate in an analogous manner to the procedure described in Example 1(f), and the product was subjected in an analogous manner to a sequence of procedures described in Example 13(f) and in Example 21 to yield dimethyl (4R, 8S)-14-(tert-butyldimethylsilyloxy)-1,3,4,5,6,7,8,10-octahydro-12-methoxy-6,10-dioxo-9,2,5-benzoxathiaazacyclododecine-4,8-dicarboxylate as a white solid. This material was treated with ammonium fluoride in methanol in an analogous manner to the procedure described in Example 13 to yield, after crystallization from ethyl acetate/hexane, dimethyl (4R, 8S)-1,3,4,5,6,7,8,10-octahydro-14-hydroxy-12-methoxy-6,10-dioxo-9,2,5-benzoxathiaazacyclododecine-4,8-dicarboxylate as a white solid.

$^1$H-NMR(250M/{z, DMSO-d$_6$): δ2.62(dd, J=14 Hz and 11 Hz, 1H); 2.75(dd, J=14 Hz and 3 Hz, 1H); 2.90 (dd, J=14 Hz and 12 Hz, 1H); 3.08 (dd, J=14 Hz and 4 Hz, 1H); 3.67(s,3H); 3.72(s,3H)3.73(s,3H); 3.91(d,J=10 Hz, 1H); 4.53 (d, J=10 Hz, 1H); 4.74 (m, 1H); 5.61 (dd, J=12 Hz and 3 Hz, 1H); 6.65 (d, J=2 Hz, 1H); 6.77 (d, J=2 Hz, 1H); 8.93 (d, J=9 Hz, 1H); 10.15 (s, 1H) ppm The starting material used above was prepared as follows:

(a) L-Cysteine methyl ester was acylated with (R)-hydroxy-1,4-butandioic acid 1-methyl ester in an analogous manner to the procedure described in Example 1(e) to yield after chromatographic purification and crystallization from ethyl acetate/hexane methyl (R)-2-[(R)-3-hydroxy-3-methoxycarbonylpropionylamino]-3-mercapto-propionate as white crystals of m.p. 80°–81° C.

EXAMPLE 33 p-Nitrobenzyl (R)-3-(tert-butyldimethylsilyloxy)-5-methoxy-2-[[[2-(3-trityloxypropionyl-methyl-amino)-2-(methoxycarbonyl)ethyl]thio]methyl]-benzoate was subjected in an analogous manner to a sequence of procedures described in Example 16(h) and 13(f), and the product was cyclized and subsequently the silyl groups were cleaved off in an analogous manner to the procedures described in Examples 21 and 13, to yield methyl (R)-1,3,4,5,6,7,8,10-octahydro-14-hydroxy-12-methoxy-5-methyl-6,10-dioxo-9,2,5-benzoxathiaazacyclododecine-4-carboxylate as a white solid.

$^1$H-NMR(250 MHz,DMSO-d$_6$): (inter alia) δ2.62(s,3H); 2.77(dd, J=15 Hz and 10 Hz,1H); 3.03 (dd, J=15 Hz and 5 Hz, 1H); 3.50–3.70 (m, 1H); 3.71 (s, 6H); 3.79 (d, J=10 Hz, 1H); 4.15 (d, J=10 Hz, 1H); 4.44–4.60 (m, 2H); 5.14 (m, 1H); 6.57 (d, J=2 Hz, 1H); 6.73 (d, J=2 Hz, 1H); 10.16 (s, 1H) ppm The starting material used above was prepared as follows:

(a) A solution of 0.53 g of p-nitrobenzyl alpha-bromo-3-(tert-butyldimethylsilyloxy)-5-methoxy-toluate and 0.17 g of L-cysteine methyl ester hydrochloride in 2 ml of methylene chloride/acetonitrile (1:1, v/v) was cooled to 0° C. and then treated with 0.20 g of triethylamine, a precipitate being formed immediately. The mixture was stirred for 4 hours at 0° C. Ethyl acetate was added, and the mixture was washed successively with saturated sodium bicarbonate solution and with brine. The organic layer was dried over sodium sulfate, and the solvent was evaporated in vacuo. The residual oil was chromatographed on silica gel using ethyl acetate/hexane (1:1, v/v) as eluent to yield 0.34 g of p-nitrobenzyl (R)-2-[[[2-amino-2-(methoxycarbonyl)ethyl]thio]methyl]-3-(tert-butyldimethylsilyloxy)-5-methoxybenzoate as an oil.

$^1$H-NMR(90 MHz,CDCl$_3$): δ0.29(s,6H); 1.03(s,9H); 1.87(broad s,2H); 2,05(s,3H); 2.66 (dd, J=14 Hz and 8 Hz, 1H); 2.95 (dd, J=14 Hz and 4 Hz, 1H); 3.60 (m, 1H); 3.71(s,3H); 3.80(s,3H); 4.20(m, 2H); 5.49(s,2H); 6.63 (d, J=2 Hz, 1H); 7.13 (d, J=2 Hz, 1H); 7.70 (d, J=8 Hz, 2H); 8.33 (d, J=8 Hz, 2H) ppm (b) A solution of 1.90 g of p-nitrobenzyl (R)-2-[[[2-amino-2-methoxycarbonyl-ethyl]thio]methyl]-3-(tert-butyldimethylsilyloxy)-5-methoxybenzoate and 0.91 g of methyl iodide in 5 ml of acetonitrile was stirred at room temperature for 3 hours. The solution was diluted with ethyl acetate and washed successively with saturated sodium bicarbonate solution and with brine. The organic layer was dried over sodium sulfate, and the solvent was evaporated in vacuo. The residual oil was chromatographed on silica gel using ethyl acetate/hexane (1:1, v/v) as eluent to yield 0.52 g of p-nitrobenzyl (R)-2-[[[2-methoxycarbonyl-2-(methylamino)ethyl]thio]methyl]-3-(tert-butyldimethylsilyloxy)-5-methoxybenzoate as an oil.

$^1$H-NMR(250 MHz, DMSO-d$_6$): δ0.26(s,6H); 1.00(s,9H); 2.15 (broad s, 3H); 2, 60 (m, 2H); 3.56(s,3H); 3.77(s,3H); 4.00(m, 2H); 5.47(s,2H); 6.57 (d,J=2 Hz,1H); 7.01 (d,J=2 Hz, 1H); 7.59(d,J=8 Hz,2H); 8.21 (d, J=8 Hz, 2H) ppm (c) To a stirred suspension of 3.32 g of 3-trityloxypropionic acid in 50 ml of methanol was added within 15 minutes a solution of 0.56 g of potassium hydroxyde in 10 ml of methanol. Stirring was continued for 30 minutes, and then the solvent was evaporated in vacuo. The residual foam was dissolved in 20 ml of methylene chloride, and to the stirred solution were slowly added 100 ml of diethylether to cause crystallization. There were obtained 3.40 g of potassium 3-trityloxypropionate as a white solid.

To a suspension of 3.30 g of potassium 3-trityloxypropionate in 75 ml of toluene, cooled to 0° C., was added 0.5 ml of pyridine, and subsequently 15 ml of oxalyl chloride were added within 10 minutes. The mixture was stirred for 30 minutes at room temperature and then evaporated in vacuo. The oily residue was taken up in 30 ml of toluene, and the solvent was evaporated in vacuo. The residue was taken up in 50 ml of methylene chloride and 50 ml of hexane, and the solution was stirred at 0° C. Unsoluble material was filtered off, and the filtrate was evaporated in vacuo to yield 2.81 g of 3-trityloxypropionyl chloride as a white solid.

(d) A solution of 0.64 g of p-nitrobenzyl (R)-2-[[[2-(methoxycarbonyl)-2-(methylamino)-ethyl]thio]methyl]-3-(tert-butyldimethylsilyloxy)-5-methoxybenzoate and 0.58 g of 3-trityloxypropionyl chloride in 6 ml of methylene chloride was treated at 0° C. with 0.17 g of triethylamine. The mixture was stirred at 0° C. for 30 minutes, then diluted with methylene chloride, and washed successively with 5% sodium bicarbonate solution and brine. The organic layer was dried over sodium sulfate, and the solvent was evaporated in vacuo. The residual oil was chromatographed on silica gel using ethyl acetate/hexane (1:2, v/v) as eluent to yield 0.65 g of p-nitrobenzyl (R)-3-(tert-butyldimethylsilyloxy)-5-methoxy-2-[[[2-(3-trityloxypropionyl-methylamino)-2-methoxycarbonyl-ethyl]thio]methyl]-benzoate as an oil.

$^1$H-NMR(250 MHz, CDCl$_3$): inter alia, δ0.23(s,3H); 0.26(s, 3H); 0.96(s.9H); 2.84(m, 2H); 2.87(s,3H); 3.19(m,2H); 3.53(s,3H); 3.76(s,3H);d,J=14 Hz, 1H); 4.78(m, 1H); 5.42(s,2H); 6.54(d,J=2 Hz, 1H); 6.99(d,J=2 Hz, 1H); 7.2–7.4 (m, 16H); 7.68(d,J=8 Hz,2H); 8.20 d,J=8 Hz,2H) ppm

EXAMPLE 34

Crude p-nitrobenzyl 2-bromomethyl-3-(tert-butyldimethylsilyloxy)-5-methoxy-6-methylbenzoate, as obtained in Example 23 (d), was subjected in an analogous manner to a sequence of procedures described in Example 33 (a, b, d), and the product was cyclized and subsequently the silyl groups were cleaved off in in analogous manner to the procedures described in Examples 21 and 13, to yield methyl (R)-1,3,4,5,6,7,8,10-octahydro-14-hydroxy-12-methoxy-5,11-dimethyl-6,10-dioxo-9,2,5-benzoxathiaazacyclododecine-4-carboxylate as a white solid.

$^1$H-NMR(250 MHz, DMSO-d$_6$): inter alia; δ1.90 (s, 3H); 2.60 (s, 3H); ~2.80 (m, 2H); 3.00 (dd, J=15 Hz and 5 Hz, 1H); 3.41(d,J=10 Hz, 1H); 3.70(s,3H); 3.72 (s,3H); 3.76(d,J=10 Hz, 1H); 6.47(s, 1H); 9.62(s,1H) ppm

EXAMPLE 35

2-[[[(R)-2-[(S)-1-tert-Butoxyformamido)-3-hydroxypropionylamino ]-2-(methoxycarbonyl)ethyl]thio]methyl]-3-(tert-butyldimethylsilyloxy)-4-chlorobenzoic acid was cyclized and the tert-butyldimethylsilyl groups subsequently cleaved off in an analogous manner to the procedure described in Examples 21 and 13. The product obtained was subjected in an analogous manner to the procedure described in Example 14 (a), the resulting amine was acylated with N-(tert-butoxycarbonyl)-L-serine in an analogous manner to the procedure described in Example 14, and the resulting product was stirred in trifluoroacetic acid at 0° C. to give, after evaporation of the solvent and trituration of the residue with diethyl ether, methyl (4R, 7S)-13-chloro-1,3,4,5,6,7,8,10-octahydro-14-hydroxy-6,10-dioxo-7-(L-serylamino)-9,2,5-benzoxathiaazacyclododecine-4-carboxylate trifluoroacetate as a white solid.

$^1$H-NMR(250 MHz, DMSO-d$_6$): δ2.85(dd, J=14 Hz and 11 Hz, 1H); 3.19(dd, J=14 Hz and 4 Hz, 1H); 3.64(s,3H); ,3.65–3.90(m,2H); 3.98(t,6 Hz, 1H); 4.04 (d,J=10 Hz, 1H); 4.34(dd, J=12 Hz and 2 Hz, 1H); 4.42(d,J=10 Hz, 1H); 4.50–4.65 (m, 1H); 4.68–4.75 (m, 1H); 4.94 (dd, J=12 Hz and 2 Hz, 1H); 6.01(broad t,1H); 7.36(d,J=9 Hz, 1H); 7.44(d,J=9 Hz, 1H); 8.51 (d, J=8 Hz, 1H); 9.11 (d, J=8 Hz, 1H) ppm The starting material used above was prepared as follows:

(a) To a suspension of 22.8 g of 3-hydroxy-2-methylbenzoic acid in 300 ml of water, cooled to 2° C., were added 55 ml of 3N sodium hydroxyde to adjust the pH to 10. To the clear solution were added within 20 minutes, at 2° to 6° C., 125 ml of 1.2N sodium hypochlorite solution, the pH being raised to 12.5. Then, 90 ml of 3N hydrochloric acid were added at once, a precipitate being formed immediately. The mixture was stirred at 0° C. for 30 minutes, and subsequently the precipitate was isolated by filtration and crystallized from diethylether/hexane to give 15.0 g of 4-chloro-3-hydroxy-2-methylbenzoic acid as white crystals of m.p. 191° C.

(b) To a solution of 1.86 g 4-chloro-3-hydroxy-2-methylbenzoic acid in 20 ml of methylene chloride, cooled to 0° C., were added 3.80 g of g of tert-butyldimethylchlorosilane, 0.12 g of 4-dimethylaminopyridine, and 2.25 g of triethylamine. After 5 minutes, the ice-bath was removed, and stirring was continued for 3 hours at 20° C. The mixture was diluted with methylene chloride and successively extracted with ice-cold water and with ice-cold 10% sodium chloride solution. The organic layer was dried over sodium sulfate, and the solvent was evaporated in vacuo to give 3.5 g of tert-butyldimethylsilyl 3-(tert-butyldimethylsilyloxy)-4-chloro-2-methylbenzoate as an oil.

$^1$H-NMR (90 MHz,CDCl$_3$): δ0.24(s,3H); 0.37(s,3H); 1.01(s,9H); 1.04(s,9H); 2.52(s,3H); 7.24 (d, J=9 Hz, 1H); 7.55 (d, J=9 Hz, 1H) ppm (c) tert-Butyldimethylsilyl 3-(tert-butyldimethylsilyloxy)-4-chloro-2-methylbenzoate was subjected in an analogous manner to the procedure described in Example 1(d) to give tertbutyldimethylsilyl 2-bromomethyl-3-(tert-butyldimethylsilyloxy)-4-chlorobenzoate as an oil.

$^1$H-NMR(90 MHz, CDCl$_3$): δ0.34(s,3H); 0.42(s,3H); 1.03(s,9H); 1.09(s,9H); 4.90 (s, 2H); 7.40(d,J=9 Hz,1H); 7.61 d,J=9 Hz, 1H) ppm d) To a solution of 5.1 g of tert-butyldimethylsilyl 2-bromomethyl-3-(tert-butyldimethylsilyloxy)-4-chlorobenzoate and 3.52 g of N-[N-(tert-butoxycarbonyl)-L-seryl]-L-cysteine methyl ester in 55 ml of methylene chloride was added within 30 minutes, at 0° C., a solution of 1.59 g of 1,8-diazabicyclo [5.4.0]undec-7-ene (DBU) in 15 ml of methylene chloride. Stirring was continued for 3 hours at 0° C., and subsequently the mixture was diluted with methylene chloride and stirred together with 100 ml of 1N aqueous acetic acid. The organic phase was washed with 10% sodium chloride solution, dried over sodium sulfate, and the solvent was evaporated in vacuo. The residue was chromatographed on MCI-Gel CHP20P using as eluent a mixture of acetonitrile-water containing 40–0% water. The product was eluted with pure acetonitrile. Evaporation of the solvent afforded 2.7 g of 2-[[[(R)-2-[(S)-1-tert-butoxyformamido )-3-hydroxypropionylamino]-2-methoxycarbonyl-ethyl ]thio]methyl]-3-(tert-butyldimethylsilyloxy)-4-chlorobenzoic acid as a white foam.

¹H-NMR(250 MHz, CDCl₃): δ0.27(s,3.H); 0.30(s,3H); 1.05(s,9H); 1.46(s,9H); 2.74–3.15 (m, 2H); 3.72(S,3H); 3.81(m, 1H); 4.09(dd, J=12 Hz and 4 Hz,1H); 4.50 (m, 2H); 5.85 (broad d; 1H); 7.18 (d, J=8 Hz, 1H); 7.29 (d, J=9 Hz, 1H); 7.50 (d, J=9 Hz, 1H) ppm

EXAMPLE 36

2,4-Dichloro-5-hydroxy-6-methylbenzoic acid was subjected in an analogous manner to a sequence of reactions described in Example 35(b,c,d), and the resulting product was subjected in an analogous manner to a sequence of reactions used in Example 35 to give, after crystallization from diethylether/toluene, methyl (4R, 7S)-11,13-dichloro-1,3,4,5,6,7,8,10-octahydro-14-hydroxy- 6,10-dioxo-7-(L-serylamino)-9,2,5-benzooxathiaazacyclododecine-4-carboxylate as a white solid.

¹H-NMR (250 MHz, DMSO-d₆): δ2.86(dd, J=14 Hz and 10 Hz, 1H); 3.21(dd, J=14 Hz and 4 Hz, 1H); 3.60(d,J=10 Hz, 1H); 3.63(s,3H); 3.67–3.84(m, 2H); 3.88 (d,J=10 Hz, 1H); 4.03(t,J=5H,1H); 4.15(dd, J=12 Hz and 3 Hz, 1H); 4.43–4.56(m, 1H); 4.76–4.84 (m, 1H); 5.31(dd, J=12 Hz and 2 Hz, 1H); 5.81(t,J=3H,1H); 7.62(s, 1H); 8.40(d,J=8 Hz,1H); 9.02 (d, J=8 Hz, 1H) ppm The starting material used above was prepared as follows:

(a) To a stirred suspension of 10.0 g of 3-hydroxy-2-methylbenzoic acid in 50 ml of glacial acetic acid, cooled to 2° C., were added 18.8 g of sulfuryl chloride. Stirring was continued for 5 minutes at 5° C., and for 30 minutes at 20° C. The solution was concentrated in vacuo to a volume of about 20 ml, and then cooled to 0° C. The precipitate formed was isolated by filtration, washed with water, and crystallized from diethylether/hexane to give 7.2 g of 2,4-dichloro-5-hydroxy-6-methylbenzoic acid as white crystals of m.p. 135° C.

EXAMPLE 37

3-Hydroxy-2-methylbenzoic acid was subjected in an analogous manner to a sequence of reactions described in Example 35(b,c,d), the resulting product was cyclized in an analogous manner to the procedure described in Example 21, the cyclization product was subjected in an analogous manner to a sequence of reactions described in Example 14(a)/14 to give, after crystallization from methylene chloride/diethylether, methyl (4R, 7S)-7-[(S)-2-(1-tert-butoxyformamido)-3-hydroxypropionylamino]-1,3,4,5,6,7,8,10-octahydro-14-hydroxy-6,10-dioxo-9,2,5-benzoxathiaazacyclododecine-4-carboxylate as a white solid.

¹H-NMR(250 MHz, DMSO-d₆): δ1.36(s,9H); 2.70(dd, J=14 Hz and 12 Hz,1H); 3.12(dd, J=14 Hz and 4 Hz, 1H); 3.46–3.76(m,2H) superimposed by 3.63(s,3H); 3.96 (d, J=10 Hz, 1H); 4.20–4.30 (m, 1H); 4.33 (dd, J=12 Hz and 2 Hz, 1H); 4.45 (d, J=10 Hz, 1H); 4.52–4.72 (m, 2H); 4.85 (dd, J=12 Hz and 2 Hz, 1H); 5.52 (t, J=3H, 1H); 6.83 (d, J=8 Hz, 1H); 7.08 (dd, J=8 Hz and 1 Hz, 1H); 7.20 (dd, J=8 Hz and 8 Hz, 1H); 7.36 (dd, J=8 Hz and 1 Hz, 1H); 8.54(d,J=9 Hz,1H); 8.60(d,J=7 Hz, 1H); 10.01(s, 1H) ppm

EXAMPLE 38

Methyl (9S, 12R)-9-amino-6,10-dioxo-2,2-diphenyl-6,8,9,10, 11,12,13,15-octahydro-1,3-dioxolo-[4,5-n][9,2,5]-benzooxathiaazacyclododecine-12-carboxylate was acylated with N-(tert-butoxytcarbonyl)-L-serine in an analogous manner to the procedure described in Example 14. The product obtained was dissolved in 95% aqueous trifluoroacetic acid. The solution was stirred at room temperature for 75 minutes, and then evaporated in vacuo. The residue was was partitioned between ethyl acetate and water. The pH of the concentrated aqueous layer was adjusted to 2.5 by the addition of 0.5N sodium hydroxide, and the solution was then chromatographed on MCI-Gel CHP20P using 20% aqueous acetonitrile as eluent. The product-containing fractions were combined and lyophilized to give methyl (4R, 7S)-1,3,4,5,6,7,8,10-octahydro-13,14-dihydroxy-6,10-dioxo-7-(L-serylamino)-9,2,5-benzoxathiaazacyclododecine-4-carboxylate as a white powder.

¹H-NMR(250MHZ,DMSO-d₆): δ2.75 (dd, 1H); 3.10 (dd, 1H); 3.40–3.70 (m, 3H) superimposed by 3.64 (s, 3H); 4.01 (d, 1H); 4.23 (dd, 1H); 4.43 (dd, 1H); 4.50–4.70 (m, 2H); 4.75 (dd, 1H); 6.78 (d, 1H); 7.32 (d, 1H); 8.50 (d, 1H) ppm The starting material used above was prepared as follows:

(a) To a suspension of 23.0 g of lithium 2,2-diphenyl-1, 3-benzodioxole-5-carboxylate in 200 ml of dimethylformamide were added 27.0 g of O-benzotriazol-1-yl-N,N,N',N'-tetramethyluronium-hexafluorophosphate. The mixture was stirred at 20° C. for 2 hours, then 25 ml of methylamine were added, and stirring was continued for another 2 hours. The mixture was partitioned between ethyl acetate and water, the organic layer was washed successively with 2N potassium hydrogensulfate solution, saturated sodium carbonate solution and brine, and dried over magnesium sulfate. The solvent was evaporated in vacuo, and the solid residue was crystallized from ethanol to give 15.6 g of N-methyl-2,2-diphenyl-1,3-benzodioxole-5-carboxamide, m.p. 144°–145° C.

(b) To a solution of 3.30 g of N-methyl-2,2-diphenyl-1, 3-benzodioxole-5-carboxamide in 20 ml of tetrahydrofuran, cooled to –78° C., were added 12.5 ml of a 1.6M solution of n-butyllithium in hexane. The solution was stirred for 1 hour, the temperature being allowed to warm up to 20° C. Then, 1.37 g of methyl iodide were added, and stirring was continued for 1 hour. After the addition of 20 ml saturated ammonium chloride solution, the mixture was extracted with ethyl acetate. The organic layer was washed successively with 2N potassium hydrogensulfate solution, saturated potassium bicarbonate solution and brine, and dried over magnesium sulfate. The solvent was evaporated in vacuo, and the solid residue was crystallized from ethanol to give 15.6 g of N, 4-dimethyl-2,2-diphenyl-1,3-benzodioxole-5-carboxamide, m.p. 178°–180° C.

(c) A solution of 1.60 g of N,4-dimethyl-2,2-diphenyl-1, 3-benzodioxole-5-carboxamide and 1.00 g of sodium hydroxide in 10 ml of ethylene glycol was heated to 190° C. for 2.5 hours. After cooling, the mixture was partitioned between water and ethyl acetate. The aqueous phase was washed with ethyl acetate, adjusted to pH 2 by the addition of 3N hydrochloric acid, and then the product was extracted with ethyl acetate. The organic layer was washed with brine and dried over magnesium sulfate. The solvent was evaporated in vacuo, and the solid residue was crystallized from ethanol to give 0.53 g of 4-methyl-2,2-diphenyl-1,3-benzodioxole-5-carboxylic acid, m.p. 263°–265° C.

(d) 4-Methyl-2,2-diphenyl-1,3-benzodioxole-5-carboxylic acid was subjected in an analogous manner to a sequence of procedures described in Examples 1(d, f), 21 and 14(a) to yield, after crystallization from ethyl acetate/hexane, methyl (9S, 12R)-9-amino-6,10-dioxo-2,2-diphenyl-6,8,9,10,11,12,13,15-octahydro-1,3-dioxolo-[4,5-n][9,2,5]-benzoxathiaazacyclododecine-12-carboxylate as white solid.

EXAMPLE 39

Crude p-nitrobenzyl 3, 5-bis (tert-butyldimethylsilyloxy)-(α-bromo-2,6-xylate, as obtained in Example 13 (e), was reacted with N-[(S)-2,3-dihydroxypropionyl]-L-cysteine methyl ester in an analogous manner to the procedure described in Example 1(f), and the product was subjected in an analogous manner to a sequence of procedures described in Example 13(f) and Example 21 to yield methyl (4R, 7S)-12, 14-bis-(tert-butyldimethylsilyloxy)-1,3,4,5,6, 7,8, 10-octahydro-7-hydroxy-11-methyl-6,10-dioxo-9,2,5-benzooxathiaazacyclododecine-4-carboxylate. This material was treated with ammonium fluoride in methanol in an analogous manner to the procedure described in Example 13 to yield, after crystallization from acetonitrile, methyl (4R, 7S)-7,12,14-trihydroxy1,3,4,5,6,7,8,10-octahydro-11-methyl-6,10-dioxo-9,2,5-benzooxathiaazacyclododecine-4-carboxylate as a white solid.

$^1$H-NMR(250 MHz, DMSO-$d_6$): δ1.87 (s, 3H); 2.89 (dd, 1H); 3.04 (dd, 1H); 3.45 (d, 1H); 3.65 (s, 3H); 3.97 (d, 1H); 4.21 (dd, 1H); 4.33 (m, 1H); 4.71 (m, 1H); 5.07 (dd (1H); 6.33 (d, 1H); 6.44 (s, 1H); 8.07 (d, 1H); 9.44 (s, 1H); 9.47 (s, 1H) ppm The starting material used above was prepared as follows:

(a) To a solution of 60.0 g of sodium-[(S)-2,2-dimethyl-1,3-dioxolan-4-yl]carboxylate in 500 ml of dimethylformamide were added 136.0 g of O-benzotriazol-1-yl-N,N,N',N'-tetramethyluronium-hexafluorophosphate. The mixture was stirred at 20° C. for 0.5 hours, then 62 g L-cysteine methyl ester hydrochloride and subsequently 36.7 g of N-methylmorpholine were added. The mixture was stirred at 20° C. for 3.5 hours. The solvent was evaporated in vacuo and the oily residue was partitioned between water and ethyl acetate. The organic layer was washed successively with saturated sodium carbonate solution, saturated potassium hydrogensulfate solution, and brine, and then dried over magnesium sulfate. The solvent was evaporated in vacuo, and the residual oil was heated at reflux in a mixture of 50 ml of trifluoroacetic acid and 500 ml of methanol for 2.5 hours. The solvent was evaporated in vacuo, and the residue was crystallized from tert-butyl-methyl-ether to give 33.4 g of N-[(S)-2,3-dihydroxypropionyl]-L-cysteine methyl ester as white crystals of m.p. 90°–92° C.

EXAMPLE 40

Operating in an analogous manner as described in Example 39, but using in the cyclization step 2 molequivalents of both diethyl azodicarboxylate and triphenylphoshine, there was obtained, after crystallization from methylene chloride, methyl [(4R,7S)-7-[(ethoxycarbonyl)oxy]-1,3,4,5,6,7,8,10-octahydro-12,14-dihydroxy-11-methyl-6,10-dioxo-9,2,5-benzoxathiaazacyclododecine-4-carboxylate as white crystals of m.p. 224°–225° C.

EXAMPLE 41

Operating in an analogous manner to the sequence of procedures described in Example 39, but using as starting material crude p-nitrobenzyl 2-bromomethyl-3-(tert-butyldimethylsilyloxy)-5-methoxy-6-methylbenzoate as obtained in example 23 (d), there was obtained methyl (4R, 7S)-14-(tert-butyldimethylsilyloxy)-1,3,4,5,6,7,8,10-octahydro-7-hydroxy-12-methoxy-11-methyl-6,10-dioxo-9,2,5-benzoxathiaazacyclododecine-4 -carboxylate. This material was treated with ammonium fluoride in methanol in an analogous manner to the procedure described in Example 13 to yield, after crystallization from ethyl acetate/hexane, methyl (4R, 7S)-1,3,4, 5,6,7,8,10-octahydro-7,14 -dihydroxy-12-methoxy-11-methyl-6,10-dioxo-9,2,5-benzoxathiaazacyclododecine-4-carboxylate as a white solid, m.p. 237°–240° C.

EXAMPLE 42

To a solution of 100 mg of the 12, 14-bis-(tert-butyldimethylsilylated)-product of Example 39, 30 mg of 2,4-dinitrophenol, and 43 mg of triphenylphosphine in 1 ml of methylene chloride were added 34 mg of diethyl azodicarboxylate. The solution was stirred at 20° C. for 24 hours, then 43 mg of triphenylphosphine and 34 mg of diethyl azodicarboxylate were added, and stirring was continued for 72 hours. The solvent was evaporated in vacuo, and the residue was chromatographed on silica gel using ethyl acetate/hexane (1:3, v/v) as eluent. The 12,14-bis-(tert-butyldimethylsilylated)-product obtained was treated with ammonium fluoride in methanol in an analogous manner to the procedure described in Example 13 to yield 6 mg of methyl (4R, 7S)-1,3,4,5,6,7,8,10-octahydro-12,14-dihydroxy-11-methyl-7-(2,4-dinitro-phenoxy)-6,10-dioxo-9,2,5-benzooxathiaazacyclododecine-4-carboxylate as a white solid.

$^1$H-NMR(250 MHz, DMSO-$d_6$): δ1.85 (s, 3H); 2.72 (dd, 1H); 3.12 (dd, 1H); 3.60 (s, 3H); 3.64 (d, 1H); 3.88 (d, 1H) ;4.66(dd, 1H); 4.80(m, 1H); 5.19(dd, 1H); 5.77(m, 1H); 6.48 (s, 1H); 7.65 (d, 1H); 8.24 (d, 1H); 8.62 (dd, 1H); 8.85 (d, 1H); 9.52 (s, 1H); 9.54 (s, 1H) ppm

EXAMPLE 43

To a solution of 50 mg of the 12,14-bis-(tert-butyldimethylsilylated)-product of Example 39 in 1 ml of methylene chloride were added at 0° C. 21 mg of pivaloyl chloride and 199 mg of 4-dimethylaminopyridine, and the mixture was stirred for 1 hour at 20° C. The solvent was evaporated in vacuo, and the residue was chromatographed on silica gel using ethyl acetate/hexane (1:1, v/v) as eluent. The 12,14-bis-(tert-butyldimethylsilylated)-product obtained was treated with ammonium fluoride in methanol in an analogous manner to the procedure described in Example 13 to yield methyl (4R, 7S)-7-(2,2-dimethylpropionyloxy)-1,3,4, 5,6,7,8,10-octahydro-12,14-dihydroxy-11-methyl- 6,10-dioxo-9,2,5-benzoxathiaazacyclododecine-4-carboxylate as a white solid.

$^1$H-NMR (250 MHz, DMSO-$d_6$): δ1.22(s,9H); 1.86(s,3H); 2.92(dd, 1H); 3.10(rid, 1H); 3.59(d, 1H); 3.65 (s, 3H); 3.82 (d, 1H); 4.66 (dd, 1H); 4.77 (m, 1H); 4.92 (dd, 1H); 5.39 m, 1H); 6.48(s,1H); 7.74(d, 1H); 9.51(s, 1H); 9.56(s, 1H) ppm

EXAMPLE 44

Methyl (R)-12,14-bis-(tert-butyldimethylsilyloxy)-1,3,4, 5,6,7,8,10-octahydro-11-methyl-6,7,10-trioxo-9,2,5-benzoxathiaazacyclododecine-4-carboxylate was treated with ammonium fluoride in methanol in an analogous manner to the procedure described in Example 13 to yield, after crystallization from methylene chloride, methyl (R)-12,14-dihydroxy-6,7,10-trioxo-1,3,4,5,6,7,8,10-octahydro-9,2,5-benzoxathiaazacyclododecine-4-carboxylate of a as a white solid, partly in form of its 7-hydrate.

$^1$H-NMR(250 MHz, DMSO-d$_6$): (inter alia) δ1.87(s,3H); 2.62 (dd, 1H); 3.04 (dd, 1H); 3.66(s,3H); 3.68 (d, 1H); 3.82 (d, 1H); 4.60 (m, 1H); 4.83 (d, 1H); 5.25 (d, 1H); 6.49 (d, 1H); 9.33(d, 1H); 9.57(s,1H); 9.61(s, 1H) ppm; in addition, signals of the 7-hydrated form were observed.

The starting material used above was prepared as follows:

(a) Using in an analogues manner the procedure described in Example 16(d), but replacing 3-trityloxy-1-propanol by a sample of 385 mg of the 12,14-bis-(tert-butyldimethylsilylated)-product of Example 39, there were obtained, after chromatographic purification on silica gel using ethyl acetate/hexane (1:1, v/v) as eluent, 184 mg of methyl (R)-12,14-bis-(tert-butyldimethylsilyloxy)-1,3,4,5,6,7,8,10-octahydro-11-methyl-6,7,10-trioxo-9,2,5-benzoxathiaazacyclododecine-4-carboxylate as a white solid, possibly in the form of its 7-hydrate.

EXAMPLE 45

A solution of 100 mg of methyl (R)-12,14-bis-(tert-butyldimethylsilyloxy)-1,3,4,5,6,7,8,10-octahydro-11-methyl-6,7,10-trioxo-9,2,5-benzoxathiaazacyclododecine-4-carboxylate and 11 mg of hydroxylamine hydrochloride in 2 ml dimethylformamide was stirred at 20° C. for 3 hours. The solvent was evaporated in vacuo, and the residue was chromatographed on silica gel using ethyl acetate/hexane (1:2, v/v) as eluent. The 12,14-bis-(tert-butyldimethylsilylated)-product obtained was treated with ammonium fluoride in methanol in an analogous manner to the procedure described in Example 13 to yield methyl (E or Z)-(R)-1,3,4,5,6,7,8,10-octahydro-12,14-dihydroxy-7-hydroxyimino-11-methyl-6,10-dioxo-9,2,5-benzoxathiaazacyclododecine-4-carboxylate as a white solid.

$^1$H-NMR (250 MHz, DMSO-d$_6$): δ1.88(s,3H); 2.68(dd, 1H); 3.10(dd, 1H); 3.60(d, 1H); 3.65(s,3H); 3.75 (d, 1H); 4.72 (m, 1H); 4.98 (d, 1H); 5.56 (d, 1H); 6.44 (s, 1H); 8.77 (d, 1H); 9.49 (s. 1H); 9.54 (s, 1H); 11.98 (s, 1H) ppm

EXAMPLE 46

Operating in an analogues manner as described in the previous example, but replacing hydroxylamine hydrochloride by O-methyl-hydroxylamine hydrochloride, there was obtained methyl (E or Z)-(R)-1,3,4,5,6,7,8,10-octahydro-12,14-dihydroxy-7-methoxyimino-11-methyl-6,10-dioxo-9,2,5-benzoxathiaazacyclododecine-4-carboxylate as a white solid.

$^1$H-NMR(250 MHz,DMSO-d$_6$): δ1.88 (s, 3H); 2.67 (dd, 1H); 3.0 9 (dd, 1H); 3.60 (d, 1H); 3.66 (s, 3H); 3.74 (d, 1H); 3.98 (s, 3H); 4.70 (m, 2H); 5.00 (d, 1H); 5.52 (d, 1H); 6.45 (s, 1H); 8.96(d, 1H); 9.50(s, 1H); 9.55(s, 1H) ppm

EXAMPLE 47

Operating in an analogues manner as described in Example 45, but replacing hydroxylamine hydrochloride by O-(tert-butyl)hydroxylamine hydrochloride, there was obtained methyl (E or Z)-(R)-7-tert-butoxyimino-1,3,4,5,6,7,8,10-octahydro-12,14-dihydroxy-11-methyl-6,10-dioxo-9,2,5-benzoxathiaazacyclododecine-4-carboxylate as a white solid.

$^1$H-NMR(250 MHz, DMSO-d$_6$): δ1.33(s,9H); 1.88(s,3H); 2.73(dd, 1H); 3.11(dd, 1H ; 3.57–3.75 (m, 2H) superimposed by 3.67 (s, 3H); 4.74 (m, 1H); 5.06 (d, 1H); 5.47 (d, 1H); 6.46 (s, 1H); 8.73 (d, 1H); 9.50 (s, 1H); 9.53 (s, 1H) ppm

EXAMPLE 48

A solution of 100 mg of methyl (R)-14-(tert-butyldimethylsilyloxy)-1,3,4,5,6,7,8,10-octahydro-12-methoxy-11-methyl-6,7,10-trioxo-9,2,5-benzoxathiaazacyclododecine-4-carboxylate and 120 mg of triphenylphosporanylideneacetic acid tertbutylester in 1 ml of toluene was stirred at 40° C. for 3 hours. The solvent was evaporated, and the residue was chromatographed on silica gel using ethyl acetate/hexane (1:3, v/v) as eluent. The two bis-(tert-butyldimethylsilylated)products obtained were treated separately with ammonium fluoride in methanol in an analogous manner to the procedure described in Example 13 to yield (i) methyl (Z)-(R)-14-hydroxy-1,3,4,5,6,7,8,10-octahydro-12-methoxy-11-methyl-7-tert-butoxycarbonylmethylene-6,10-dioxo-9,2,5-benzoxathiaazacyclododecine-4-carboxylate as white crystals, m.p. 146°–149° C. (from acetonitrile), and (ii) methyl (E)-(R)-14-hydroxy-1,3,4,5,6,7,8,10-octahydro-12-methoxy-11-methyl-7-tert-butoxycarbonylmethylene-6,10-dioxo-9,2,5-benzoxathiaazacyclododecine-4-carboxylate as a white solid.

$^1$H-NMR(250 MHz, DMSO-d$_6$) (E-isomer): δ1.49 (s, 9H); 1.91 (s, 3H); 2.67 (dd, 1H); 3.12 (dd, 1H); 3.59 (d, 1H); 3.66 (s, 3H); 3.72 (s, 3H); 3.79 (d, 1H); 4.68 (m, 1H); 5.27 (d, 1H); 5.89 (d, 1H); 6.13(s,1H); 6.50(s, 1H); 8.99(d, 1H); 9.73(s, 1H) ppm The starting material used above was prepared as follows:

(a) Using in an analogues manner the procedure described in Example 16(d), but replacing 3-trityloxy-1-propanol by the 14-(tert-butyldimethylsilylated)-product of Example 41, there was obtained methyl (R)-14-(tert-butyldimethylsilyloxy)-1,3,4,5,6,7,8,10-octahydro-12-methoxy-11-methyl-6, 7,10-trioxo-9,2,5-benzoxathiaazacyclododecine-4-carboxylate as a white solid, partly in the form of its 7-hydrate.

EXAMPLE 49

The product of Example 48 (a) was subjected in an analogues manner to the procedure described in Example 45, but replacing hydroxylamine hydrochloride by O-methyl-hydroxylamine hydrochloride to yield methyl (E or Z) (R)-1,3,4,5,6,7,8,10-octahydro-14-hydroxy-12-methoxy-7-methoxyimino-11-methyl-6,10-dioxo-9,2,5-benzoxathiaazacyclododecine-4-carboxylate as white crystals of m.p. 234°–236° C. (from acetonitrile).

EXAMPLES 50–57

Using as starting material the products of examples 16, 21, 28, 120, 119, 130, 150, and 118, respectively, and operating in an analogous manner as described in Example 3, the following compounds were prepared:

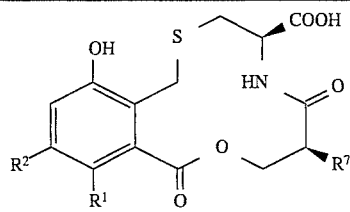

| Example No | R¹ | R² | R⁷ | ¹H-NMR (250 MHz, DMSO-d₆) δ, inter alia, ppm |
|---|---|---|---|---|
| 50 | Me | OH | H | 1.86(s, 3H); 2.42(m, 1H); 2.58(dd, 1H); 2.91 (m, 1H); 3.06(dd, 1H); 3.64(d, 1H); 3.73 (d, 1H); 4.44–4.72(m, 3H); 6.42(s, 1H); 8.44 (d, 1H); 9.48(d, 1H); 12.86(broad s, 1H) |
| 51 | Me | OMe | NHCOOBuᵗ | 1.41(s, 9H); 1.94(s, 3H); 2.91(dd, 1H); 3.05 (dd, 1H); 3.72(s, 3H); 3.92(d, 1H); 4.18 (dd, 1H); 4.30(m, 1H); 4.44(m, 1H); 4.92 (dd, 1H); 6.51(s, 1H); 7.38(d, 2H); 7.89 (d, 2H); 9.72(s, 1H) |
| 52 | H | OMe | NHCOOBuᵗ | 1.42(s, 9H); 2.90(dd, 1H); 3.07(dd, 1H); 3.7 1(s, 3H); 3.83(d, 1H); 4.24(dd, 1H); 4.30-4.44(m, 2H); 4.56(m, 1H); 4.80(dd, 1H); 6.59 (d, 1H); 6.78(d, 1H); 7.50(d, 1H); 8.08 (d, 1H); 10.02(s, 1H); 12.40(broad s, 1H) |
| 53 | Me | OH | NHCOMe | 1.90(s, 3H); 1.95(s, 3H); 2.83(dd, 1H); 3.08 (dd, 1H); 3.90(d, 1H); 4.10(dd, 1H); 4.36 (m, 1H); 4.59(s, 1H); 5.12(dd, 1H); 6.44 (s, 1H); 7.94(d, 1H); 8.37(d, 1H); 9.48 (s, 1H); 9.50(s, 1H); 12.80(broad s, 1H) |
| 54 | Me | OMe | NHCOMe | 1.94(s, 3H); 1.95(s, 3H); 2.90(dd, 1H); 3.08 (dd, 1H); 3.42(d, 1H); 3.72(s, 3H); 3.86 (d, 1H); 4.07(dd, 1H); 4.35(m, 1H); 4.61 (m, 1H); 5.11(dd, 1H); 6.51(s, 1H); 8.00 (d, 1H); 8.34(d, 1H)9.73(s, 1H); 12.90 (s, 1H); |
| 55 | Me | OMe | NHCHO | 1.93(s, 3H); 2.88(dd, 1H):3.07(dd, 1H); 3.46(d, 1H); 3.72(s, 3H); 3.84(d, 1H); 4.10 (dd, 1H); 4.37(m, 1H); 4.69(m, 1H); 5.17 (dd, 1H); 6.51(s, 1H); 8.08(d, 1H); 8.13 (s, 1H); 8.62(d, 1H); 9.73(s, 1H) |
| 56 | Me | OH | NHCH(Me)₂ | 1.01(d, 3H); 1.03(d, 3H); 1.89(s, 3H); 2.81 (m, 1H); 3.00(m, 1H); 3.09(d, 1H); 3.87 (d, 1H); 4.00–4.18(m, 2H); 4.98(dd, 1H); 6.41(s, 1H); 8.36(d, 1H); 9.44(s, 1H); 9.48 (s, 1H); |
| 57 | Me | OH | —NHC(O)CH₂CH₂N(H)Me | 1.91(s, 3H); 2.42(s, 3H); 2.52–3.20(m, 7H); 3.82(m, 1H); 3.98(dd, 1H); 4.40(m, 1H); 5.20 (dd, 1H), 6.46(s, 1H); 7.68(d, 1H); 9.14 (d, 1H); 9.52(broad s, 1H) |

EXAMPLE 58

To a solution of 114 mg of sodium borohydride in 1.5 ml of 80% aqueous methanol, cooled to 0° C., was added within 5 minutes a solution of 214 mg of tert-butyl (4R, 7S)-12, 14-bis(tert-butyldimethylsilyloxy)-1,3,4,5,6,7,8,10-octahydro-4-(methoxycarbonyl)-11-methyl-6,10-dioxo-9,2,5-benzoxathiaazacyclododecine-7-carbamate in 1.5 ml of methanol/tetrahydro-furan (1:1, v/v). The solution was stirred at 0° C. for 30 minutes, and then poured into ice-cold 0.5N hydrochloric acid. The mixture was extracted with ethyl acetate, and the organic layer was washed with brine, and dried over sodium sulfate. The solvent was evaporated in vacuo to yield 181 mg of tert-butyl (4R, 7S)-12, 14-bis (tert-butyldimethylsilyloxy)-1,3,4,5,6,7,8, 10-octahydro-4-hydroxymethyl-11-methyl-6,10-dioxo-9,2,5-benzoxathiaazacyclododecine-7-carbamate as an amorphous solid. This material was treated with ammonium fluoride in methanol in an analogous manner to the procedure described in Example 13 to yield, after crystallization from ethyl acetate/methanol/hexane, tert-butyl (4R, 7S)-1,3,4,5,6,7,8,10-octahydro-12, 14-dihydroxy-4-hydroxymethyl-11-methyl-6,10-dioxo-9,2, 5-benzoxathiaazacyclododecine-7-carbamate as a white solid.

¹H-NMR(250 MHz, DMSO-d₆): δ1.41(s,9H); 1.89,(s,3H); 2.53(dd, 1H); 2.83(dd, 1H); 3.24–3.50 (m, 3H); 3.74–3.93(m, 2H); 4.16(dd, 1H); 4.30(m, 1H); 4.79(t,1H); 4.93(dd, 1H); 6.44(s, 1H); 7.13(d, 1H); 7.60(d, 1H); 9.45(s, 1H); 9.49 (s, 1H) ppm

EXAMPLES 59–61

Using as starting material the 12,14-bis (tert-butyldimethylsilylated)-product of Example 16, and the 14-(tert-butyldimethylsilylated)-products of Examples 21 and 32, respectively, and operating in an analogous manner as described in Example 58, the following compounds were prepared.

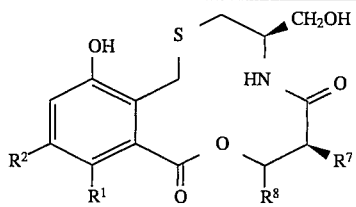

| Example No | R¹ | R² | R⁷ | R⁸ | $^1$H-NMR (250 MHz, DMSO-$d_6$) δ, inter alia, ppm |
|---|---|---|---|---|---|
| 59 | Me | OH | H | H | 1.86(s, 3H); 2.33(m, 1H); 2.75–2.90 (m, 1H); 3.20–3.45(m, 2H); 3.61(d, 1H) 3.70(d, 1H); 3.94(m, 1H); 4.48(m, 1H); 4.64(m, 1H); 4.78(t, 1H); 6.41(s, 1H); 7.86(d, 1H); 9.40(s, 1H); 9.46(s, 1H) |
| 60 | Me | OMe | NHCOOBu$^t$ | H | 1.41(s, 9H); 1.93(s, 3H); 2.83(dd, 1H); 3.26–3.42(m, 2H); 3.45(d, 1H); 3.72 (s, 3H); 3.85(d, 1H); 4.15(dd, 1H); 4.27 (m, 1H); 4.79(t, 1H); 4.95(dd, 1H); 6.51 (s, 1H); 7.13(d, 1H); 7.59(d, 1H); 9.68 (s, 1H) |
| 61 | H | OMe | H | CH$_2$OH | 2.30–2.72(m, 4H); 3.22–3.42(m, 2H); 3.52(t, 1H); 3.70(s, 3H); 3.83(d, 1H); 4.02(m, 1H); 4.52(d, 1H); 4.78(t, 1H); 4.98(t, 1H); 5.46(m, 1H); 6.55(d, 1H); 6.61(d, 1H); 7.98(d, 1H); 9.91(s, 1H) |

EXAMPLE 62

A solution of 50 mg of tert-butyl (4R, 7S)-12,14-bis(tertbutyldimethylsiiyloxy)-1,3,4,5,6,7,8,10-octahydro-4-hydroxy-methyl-11-methyl-6,10-dioxo-9,2,5-benzoxathiaazacyclodecine-7-carbamate in 1 ml of acetic anhydride was treated with 20 mg of pyridine, and then stirred for 3 hours at 20° C. The solution was evaporated in vacuo, and the residue was dissolved in ethyl acetate. The solution was washed with 5% sodium bicarbonate solution and with brine, and then dried over sodium sulfate. The solvent was evaporated in vacuo to yield 52 mg of tert-butyl (4R,7S)-4-acetoxymethyl-12,14-bis( tert-butyldimethylsilyloxy)-1,3,4,5,6,7,8,10-octahydro-11-methyl-6,10-dioxo-9,2,5-benzoxathiaazacyclododecine-7carbamate. This material was treated with ammonium fluoride in methanol in an analogous manner to the procedure described in Example 13 to yield, after crystallization from ethyl acetate/methanol/hexane, tert-butyl (4R, 7S)-4-acetoxymethyl-1,3,4,5,6,7,8,10 -octahydro-12,14 -dihydroxy-11-methyl-6,10-dioxo-9,2,5-benzoxathiaazacyclododecine-7-carbamate as a white solid.
$^1$H-NMR (250 MHz, DMSO-$d_6$): δ1.41 (s, 9H); 1.89 (s, 3H); 1.98 (s, 3H); 2.53 (dd, 1H); 2.82 (dd, 1H); 3.47 (d, 1H); 3.82 (d, 1H); 3.90–4.16 (m, 3H); 4.21 (dd, 1H); 4.32 (m, 1H); 4.95 (m, 1H); 6.44 (s, 1H); 7.02 (d, 1H); 7.78 (d, 1H); 9.48 (s, 1H); 9.51 (s, 1H) ppm

EXAMPLE 63

The 12,14-bis (tert-butyldimethylsilylated)-product of Example 59 was subjected in an analogous manner to the procedure described in Example 62 to give [(R)-1,3,4,5,6,7,8,10-octahydro-12,14-dihydroxy-11-methyl-6,10-dioxo-9,2,5-benzoxathiaazacyclododecin-4-yl]-methyl acetate as a white solid.
$^1$H-NMR (250 MHz, DMSO-$d_6$): δ1.88(s,3H); 2.01(s,3H); 2.33–2.47(m,2H); 2.75–2.89(m, 2H); 3.69 (dd, 2H); 3.89 (dd, 1H); 3.99 (dd, 1H); 4.17 (m, 1H); 4.51 (m, 1H); 4.61 (m, 1H); 6.41(s, 1H); 8.05(d, 1H); 9.43(s,1H); 9.48(s, 1H) ppm

EXAMPLE 64

The 14-(tert-butyldimethylsilylated)-product of Example 60 was subjected in an analogous manner to the procedure described in Example 62 to give tert-butyl (4R, 7S)-4-acetoxymethyl-1,3,4,5,6,7,8,10-octahydro-14-hydroxy-12-methoxy-11-methyl-6,10-dioxo-9,2,5-benzoxathiaazacyclododecine-7-carbamate as a white solid.
$^1$H-NMR(250 MHz, DMSO-$d_6$): δ1.41 (s, 9H); 1.92 (s, 3H); 1.98 (s, 3H); 2.53 (dd, 1H); 2.83 (dd, 1H); 3.50 (d, 1H); 3.72 (s,3H); 3.86(d, 1H); 3.90–4.15(m, 1H); 4.20(dd, 1H); 4.29 (m, 1H); 4.95(m, 1H); 6.51(s, 1H); 7.01(d, 1H); 7.79(d, 1H); 9.72 (s, 1H) ppm

EXAMPLE 65

A solution of 74 mg of the 12,14-bis(tert-butyldimethylsilylated)-product of Example 59, 23 mg of phtalic anhydride, and 19 mg of 4-dimethylaminopyridine in 2 ml of methylene chloride was heated at reflux for 3 hours. The solution was diluted with methylene chloride, washed with 3N hydrochloric acid and with brine, and then dried over sodium sulfate. The solvent was evaporated in vacuo, the residue was taken up in 2.6 ml of methanol, and 26 mg of ammonium fluoride were added. The mixture was stirred for 30 minutes at 20° C., and then partitioned between water and ethyl acetate. The aqueous phase was concentrated and chromatographed on MCI-Gel CHP20P using 0–20% aqueous acetonitrile as eluent. The product-containing fractions were combined and lyophilized to give [(R)-1,3,4,5,6,7,8, 10-octahydro-12,14-dihydroxy-11-methyl-6,10-dioxo9,2,5-benzoxathiaazacyclododecin-4-yl]-methyl hydrogen phtalate as a white powder.
$^1$H-NMR(250 MHz, DMSO-$d_6$): δ1.67(s,3H); 2.22–2.56(m, 2H); 2.77–2.97(m, 2H); 3.70(m, 2H); 4.10–4.40 (m, 3H); 4.47–4.71 (m, 2H); 6.42 (s, 1H); 7.60–7.80 (m, 4H); 8.17 (d, 1H); 9.43(s,1H); 9.48(s, 1H); 13.35(broad s; 1H) ppm

EXAMPLE 66

A solution of 103 mg of tert-butyl (4R, 7S)-12, 14-bis (tertbutyldimethylsilyloxy)-1,3,4,5,6,7,8, 10-octahydro-4- hydroxymethyl-11-methyl-6,10-dioxo-9,2,5-benzoxathi-aazacyclododecine-7-carbamate in 2 ml of methylene chloride was treated with 99 mg of carbontetrabromide and 79 mg of triphenylphosphine, and then stirred at 20° C. for 15 minutes. The solution was chromatographed on silica gel using ethyl acetate/hexane (1:3, v/v) as eluent to yield tert-butyl (4R, 7S)-4-bromomethyl-12,14-bis-(tert-butyldimethylsilyloxy)-1,3,4,5,6,7,8,10-octahydro-11-methyl-6,10-dioxo-9,2,5-benzooxathiaazacyclododecine-7-carbamate. This material was treated with ammonium fluoride in methanol in an analogous manner to the procedure described in Example 13 to yield, after crystallization from ethyl acetate/hexane, tert-butyl (4R, 7S)-4-bromomethyl- 1,3,4,5,6,7,8,10-octahydro-12,14-dihydroxy-11-methyl-6,10-dioxo-9,2,5-benzoxathiaazacyclododecine-7-carbamate as a white solid.

Mass spectrum: m/z (inter alia) 540 (M+Na); 465/463 (M+H-$C_4H_8$)

EXAMPLE 67

A solution of 61 mg of tert-butyl (4R, 7S)-14-(tert-butyldimethylsilyloxy)-1,3,4,5,6,7,8,10-octahydro-12-methoxy-4-methoxycarbonyl-11-methyl-6,10-dioxo-9,2,5-benzoxathiaazacyclododecine-7-carbamate and 11.4 mg of tetraisopropyl orthotitanate in 2 ml of ethanol was heated at reflux for 40 hours. The solution was diluted with ethyl acetate and washed successively with 1N hydrochloric acid and with brine. The organic layer was dried over sodium sulfate and evaporated in vacuo. The residue was chromatographed on silica gel using ethyl acetate/hexane (1:2, v/v) as eluent to yield tert-butyl (4R, 7S)-14-(tert-butyldimethylsilyloxy)-4-ethoxycarbonyl-1,3,4,5,6,7,8,10-octahydro-12-methoxy-11-methyl-6,10-dioxo-9,2,5-benzoxathiaazacyclododecine-7-carbamate. This material was treated with ammonium fluoride in methanol in an analogous manner to the procedure described in Example 13 to yield, after crystallization from ethyl acetate/hexane, tert-butyl (4R, 7S)-4-ethoxycarbonyl-1,3,4,5,6,7,8,10-octahydro-14-hydroxy-12-methoxy-11-methyl-6,10-dioxo-9,2,5-benzoxathiaazacyclododecine-7-carbamate as a white solid.

$^1$H-NMR(250 MHz,DMSO-$d_6$): δ1.17(t,J=7 Hz,3H); 1.41(s, 9H); 1.93(s,3H); 2.85(dd, J=14 Hz and 10 Hz, 1H); 3.03 (dd, J=14 Hz and 4 Hz, 1H); 3.43 (d, J=10 Hz, 1H); 3.72 (s,3H); 3.83(d,J=10 Hz, 1H); 4.09(q,J=7 Hz,2H); 4.21(dd, J=10 Hz and 4 Hz, 1H); 4.34 (m, 1H); 4.48 (m, 1H); 4.85 (m, 1H); 5.51 (s, 1H); 7,26(d,J=8 Hz, 1H); 8.14(d,J=5Hz, 1H); 9.73(s, 1H) ppm

EXAMPLES 68–77

Operating in an analogues manner as described in the previous example, the product of Example 2 was transesterified with n-propanol (1 hour at 100° C.), the product of Example 130 with ethanol (24 hours at reflux), the 14-(tert, butyldimethylsilylated)-product of Example 21 with 2-methoxy-ethanol (20 hours 120° C.),with cyclopropylmethanol (40 hours at 120° C.), and with 4-hydroxy-tetrahydropyran (36 hours at 100° C.), the 14-(tert-butyldimethylsilylated)-product of Example 130 with 2-methoxy-ethanol (20 hours 120° C.), and the 12,14-bis-(tert-butyldimethylsilylated)-product of Example 13 with cyclopentanol (36 hours at 120° C.), with 3-butin-1-ol (48 hours at reflux), and with 2,5-dimethoxybenzyl alcohol (48 hours at 120° C.), and the 12,14-(tert-butyldimethylsilylated)-product of Example 16 with allyl alcohol to give the following compounds:

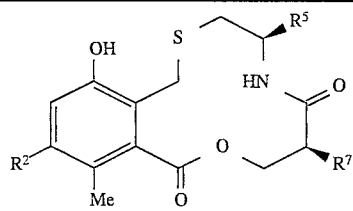

| Example No | $R^2$ | $R^5$ | $R^7$ | $^1$H-NMR (250 MHz, DMSO-$d_6$) δ, inter alia, ppm |
|---|---|---|---|---|
| 68 | OH | COOCH$_2$CH$_2$CH$_3$ | NHCOOBu$^t$ | 0.87(t, 3H); 1.41(s, 9H); 1.57(q, 2H); 1.90(s, 3H); 2.87(dd, 1H); 3.04(dd, 1H); 3.42(d, 1H); 3.79(d, 1H); 4.00(t, 2H); 4.19(dd, 1H); 4.34(m, 1H); 4.47(m, 1H); 4.83(m, 1H); 6.41(s, 1H); 7.21(d, 1H); 8.13(d, 1H); 9.49(s, 1H); 9.51(s, 1H) |
| 69 | OMe | COOCH$_2$CH$_3$ | NHCHO | 1.17(t, 3H); 1.93(s, 3H); 2.87(dd, 1H); 3.09(dd, 1H); 3.57(d, 1H); 3.72(s, 3H); 3.76(d, 1H); 4.07(q, 2H); 4.13(dd, 1H); 4.39(m, 1H); 4.71(m, 1H); 5.10(dd, 1H); 6.49(s, 1H); 8.10(s, 1H); 0.31(d, 1H); 8.53(d, 1H); 9.68(s, 1H) |
| 70 | OMe | COOCH$_2$CH$_2$OCH$_3$ | NHCOOBu$^t$ | 1.41(s, 9H); 1.93(s, 3H); 2.81(dd, 1H) 3.05(dd, 1H); 3.25(s, 3H); 3.42–3.54 (m, 3H); 3.72(s, 3H); 3.82(d, 1H); 4.07–4.25(m, 3H); 4.35(m, 1H); 4.48(m, 1H); 4.87(dd, 1H); 6.51(s, 1H); 7.20(d, 1H) 8.19(d, 1H); 9.73(s, 1H) |
| 71 | OMe | COOCH$_2$—◁ | NHCOOBu$^t$ | 0.26(m, 2H); 0.50(m, 2H); 1.07(m, 1H) 1.41(s, 9H); 1.93(s, 3H); 2.87(dd, 1H); 3.06(dd, 1H); 3.45(d, 1H); 3.72(s, 3H); 3.84(d, 1H); 3.89(m, 2H); 4.20(dd, 1H); 4.35(m, 1H); 4.49(m, 1H); 4.85(m, 1H); 6.51(s, 1H); 7.24(d, 1H); 8.14(d, 1H) 9.74(s, 1H) |

-continued

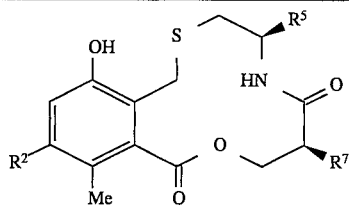

| Example No | R² | R⁵ | R⁷ | ¹H-NMR (250 MHz, DMSO-d₆) δ, inter alia, ppm |
|---|---|---|---|---|
| 72 | OMe | COO-(tetrahydropyranyl) | NHCOOBuᵗ | 1.41(s, 9H); 1.48–1.64(m, 2H); 1.75–1.91(m, 2H); 1.93(s, 3H); 2.89(dd, 1H) 3.06(dd, 1H); 3.38–3.54(m, 3H); 3.66–3.87(m, 3H) superimposed by 3.72 (s, 3H); 4.25(dd, 1H); 4.32–4.52(m, 2H); 4.81(dd, 1H); 4.89(m, 1H); 6.50(s, 1H) 7.26(d, 1H); 8.25(d, 1H); 9.73(s, 1H) |
| 73 | OMe | COOCH₂CH₂OCH₃ | NHCHO | 1.93(s, 3H); 2.87(dd, 1H); 3.10(dd, 1H); 3.25(s, 3H); 3.51(t, 2H); 3.57(d, 1H) 3.72(s, 3H); 3.74(d, 1H); 4.07–4.23 (m, 3H); 4.40(m, 1H); 4.72(m, 1H); 5.11 (dd, 1H); 6.51(s, 1H); 8.12(s, 1H); 8.39 (d, 1H); 8.53(d, 1H); 9.70(broad s, 1H) |
| 74 | OH | COO-(cyclopentyl) | NHCOOBuᵗ | 1.41(s, 9H); 1.44–1.86(m, 9H); 1.89 (s, 3H); 2.86(dd, 1H); 3.02(dd, 1H); 3.34 (s, 3H); 3.41(d, 1H); 3.76(d, 1H); 4.21 (dd, 1H); 4.30–4.45(m, 2H); 4.79m, 1H); 5.06(m, 1H); 6.41(s, 1H); 7.27(d, 1H); 8.15(d, 1H); 9.48(s, 1H); 9.50(s, 1H) |
| 75 | OH | COOCH₂CH₂C≡CH | NHCOOBuᵗ | 1.41(s, 9H); 1.89)s, 3H); 2.83(dd, 1H); 2.90(t, 1H); 3.04(dd, 1H); 3.48(d, 1H); 3.77(d, 1H); 4.11(m, 2H); 4.20(dd, 1H); 4.36(m, 1H); 4.48(m, 1H); 4.85(dd, 1H); 6.43(s, 1H); 7.18(d, 1H); 8.26(d, 1H); 9.49(s, 1H); 9.51 |
| 76 | OH | COOCH₂-(2,5-dimethoxyphenyl) | NHCOOBuᵗ | 1.39(s, 9H); 1.89(s, 3H); 2.87(dd, 1H); 3.06(dd, 1H); 3.41(d, 1H); 3.70(s, 3H); 3.74(s, 3H); 3.81(d, 1H); 4.15(dd, 1H); 4.34(m, 1H); 4.56(m, 1H); 4.88(dd, 1H); 5.03(d, 1H); 5.13(d, 1H); 6.45(s, 1H) 6.84–6.98(m, 3H); 7.20(d, 1H); 8.21 (d, 1H); 9.50(s, 1H); 9.52(s, 1H) |
| 77 | OH | COOCH₂CH=CH₂ | H | 1.86(s, 3H); 2.60(dd, 1H); 2.90(m, 1H) 3.08(dd, 1H); 3.65–3.54(m, 3H); 4.45–4.75(m, 6H); 5.30(dd, 1H); 5.38(dd, 1H) 5.90(m, 1H); 6.42(s, 1H); 8.60(d, 1H) 9.46(s, 1H); 9.50(s, 1H) |

EXAMPLE 78

A solution of 291 mg of the product of Example 2 was dissolved in 6 ml of saturated methanolic ammonia which had been prepared by the introduction of dry ammonia into methanol at 10° C. The solution was kept at 20° C. for 7 hours, and then evaporated in vacuo. The residue was crystallized from ethyl acetate to yield 243 mg of tert-butyl (4R, 7S)-4-carbamoyl-1,3,4,5,6,7,8,10-octahydro-12,14-dihydroxy-11-methyl-6,10-dioxo-9,2,5-benzoxathiaazacyclododecine-7-carbamate as a white solid.

¹H-NMR(250 MHz, DMSO-d₆): δ1.41 (s, 9H); 1.90 (s, 3H); 2.75 (dd, 1H); 3.01 (dd, 1H); 3.32 (d, 1H); 3.89 (d, 1H); 4.15(dd, 1H); 4.22(m, 1H); 4.39(m, 1H); 4.93(dd, 1H); 6.44 (s, 1H); 7.25 (s, 1H); 7.38 (s, 1H); 7.54 (d, 1H); 7.88 (d, 1H); 9.46 (s, 1H); 9.49 (s, 1H) ppm

EXAMPLE 79

The product of Example 32 was subjected in an analogous manner to the procedure described in the previous example to yield, after crystallization from ethyl acetate/hexane, (4R,8S)-1,3,4,5,6,7,8,10-octahydro-14-hydroxy-12-methoxy-6,10-dioxo-9,2,5-benzoxathiaazacyclododecine-4,8-dicarbamate as a white solid.

¹H-NMR(250 MHz,DMSO-d₆): δ2.85 (dd, 1H); 3.03 (dd, 1H); 3.72 (s. 3H); 3.90 (d, 1H); 4.57–4.71 (m, 2H); 5.52(dd, 1H); 6.61(d, 1H); 6.76(d, 1H); 6.93(s,1H); 7.24 (s, 1H); 7.50(s, 1H); 7.73(s,1H); 8.56(d, 1H); 10.03(s,1H) ppm

EXAMPLE 80

A solution of 40 mg of the product of Example 39 in 0.5 ml of methanol and 0.1 ml of 40% aqueous methylamine was stirred at 20° C. for 1 hour. The solution was evaporated in vacuo, and the residue was chromatographed on silica gel using ethyl acetate/methanol (9:1, v/v) as eluent. The purified product was triturated with chloroform to yield 20 mg of (4R,7S)-7,12,14-trihydroxy- 1,3,4,5,6,7,8,10-octahydro-11-methyl-6,10-dioxo-9,2,5-benzoxathiaazacyclododecine-4 -carboxylic acid methylamide as a white solid, m.p. 275°–277° C.

$^1$H-NMR (250 MHz,DMSO-d$_6$): δ1.87 (s, 3H); 2.59 (d, 3H); 2.73 (dd, 1H); 2.99 (dd, 1H); 3.32 (s, 3H); 3.38 (d, 1H); 3.93(d, 1H); 4.18(dd, 1H); 4.29(m, 1H); 4.48(m, 1H); 5.07 (dd, 1H); 6.25 (d, 1H); 6.43 (s, 1H); 7.79 (d, 1H); 7.91 (d, 1H); 9.44 (d, 1H) ppm

EXAMPLE 81

A solution of 154 mg of the product of Example 119 and 1.52 g of allylamine in 2 ml of methanol was heated to 50° C. for 2 hours. The solution was evaporated in vacuo, and the residue was dissolved in 3 ml of methanol. The solution was diluted with ethyl acetate and washed successively with 3N hydrochloric acid and with brine. The organic layer was dried over sodium sulfate and evaporated in vacuo. The residue was crystallized from methanol/diethylether to give 85 mg of (4R, 7S)-7-acetylamino-1,3,4,5,6,7,8,10-octahydro-14-hydroxy-12-methoxy-11-methyl-6,10-dioxo-9,2,5-benzoxathiaazacyclododecine-4-carboxylic acid allylamide as a white solid.

$^1$H-NMR (250 MHz, DMSO-d$_6$): δ1.93(s,3H); 1.96(s,3H); 2.78(dd, 1H); 3.08(dd, 1H); 3.40(d, 1H); 3.65–3.88(m, 2H) superimposed by 3.72(s,3H); 3.93(d, 1H); 4.11 (dd, 1H); 4.38–4.51 (m, 2H); 5.05 (dd, 1H); 5.13 (dd, 1H); 5.19 (dd, 1H); 5.78 (m, 1H); 6.52 (s, 1H); 7.85 (d, 1H); 7.96 (t, 1H); 8.51 (d, 1H); 9.73 (s, 1H) ppm

EXAMPLE 82

To a solution of 188 mg of the product of Example 3 in 6 ml of acetonitrile, cooled to 0° C., were added 46 mg of N-hydroxysuccinimide and 83 mg of dicyclohexyl-carbodiimide. The mixture was stirred at 0° C. for 3 hours, and then allowed to warm up to 20° C. within 1 hour. A solution of 144 mg of L-alanine 2,2,2-trichloroethylester in 1 ml of acetonitrile was added to the mixture, and stirring was continued at 20° C. for 1.5 hours. The precipitate was removed by filtration, and the filtrate was diluted with ethyl acetate and washed successively with 3N hydrochloric acid, water, saturated sodium carbonate solution, and brine. The organic layer was dried over sodium sulfate and evaporated in vacuo. The residue was chromatographed on silica gel using ethyl acetate/hexane (2:1, v/v) as eluent to yield 156 mg of N-[[(4R, 7S)-1,3,4,5,6,7,8,10-octahydro-12,14-hydroxy-7-(tert-butoxycarbonylamino)-11-methyl-6,10-dioxo-9,2,5-benzoxathiaazacyclododecin-4-yl]-carbonyl]-L-alanine 2,2,2-trichloroethylester. A sample of 121 mg of this material was subjected in an analogous manner to the procedure described in Example 1 (g) to yield after crystallization from ethyl acetate/hexane 90 mg of N-[[(4R, 7S)-1,3,4,5,6,7,8,10-octahydro-12,14-hydroxy-7-(tertbutoxycarbonylamino)-11-methyl-6,10-dioxo-9,2,5-benzooxathiaazacyclododecin-4-yl]-carbonyl]-L-alanine as a white solid.

$^1$H-NMR(250 MHz, DMSO-d$_6$): δ1.24 (d, 1H); 1.41 (s, 9H); 1.90 (s, 3H); 2.64 (dd, 1H); 3.01 (dd, 1H); 3.38 (d, 1H); 3.92 (d, 1H); 4.00–4.18 (m, 2H); 4.30 (m, 1H); 4.58m, 1H); 4.97 (dd, 1H); 6.45 (s, 1H); 7.43(d, 1H); 7.94(d, 1H); 8.23 (d, 1H); 9.52(s,1H); 9.55(s, 1H) ppm

EXAMPLE 83

To a suspension of 107 mg of the product of Example 54 in 5 ml of acetonitrile, cooled to 0° C., were added 43 mg of N-hydroxysuccinimide and 72 mg of N-(dimethylaminopropyl)-N'-ethylcarbodiimide hydrochloride. The mixture was stirred at 0° C. for 3 hours, then 68 mg of β-alanine tert-butylester hydrochloride and 38 mg of 4-methylmorpholine were added, and stirring was continued for for 15 hours at 20° C. The mixture was diluted with ethyl acetate and washed successively with 3N hydrochloric acid, water, saturated sodium bicarbonate solution, and brine. The organic layer was dried over sodium sulfate and evaporated in vacuo. The residue was dissolved in 2.5 ml of trifluoroacetic acid, and the solution was stirred at 0° C. for 30 minutes. The solvent was evaporated in vacuo, and the residue was taken up in 1 ml of water and chromatographed on MCI-Gel CHP20P using 0–20% aqueous acetonitrile as eluent. The product-containing fractions were combined and lyophilized to give 9 mg of N-[[(4R,7S)-7-acetylamino-1,3, 4,5,6,7,8,10-octahydro-14-hydroxy-12-methoxy-11-methyl-6,10-dioxo-9,2,5-benzoxathiaazacyclododecine-4-yl]-carbonyl]β-D-alanine as a white powder.

$^1$H-NMR (250 MHz, DMSO-d$_6$): δ1.82–2.09 (m, ~3H) superimposed by 1.93 (s, 3H) and 1.98 (s. 3H); 2.66 (dd, 1H); 3.04–3.22 (m, 3H); 3.59 (d, 1H); 3.71 (s, 3H); 3.73 (d, 1H); 4.45 (m, 1H); 4.75 (dd, 1H); 6.52 (s, 1H); 8.39 (d, 1H); 8.68 (t, 1H); 9.15 (d, 1H); 10.10 (broad s, 1H) ppm

EXAMPLE 84

To a solution of 97 mg of the product of Example 51 in 6 ml of acetonitrile, cooled to 0° C., were added 34.5 mg of N-hydroxysuccinimide and 57.5 mg of N-(dimethylaminopropyl)-N'-ethylcarbodiimide hydrochloride. The mixture was stirred at 0° C. for 3 hours, then a solution of 23 mg of allylamine in 1 ml of acetonitrile was added, and stirring was continued for 1.5 hours at 20° C. The mixture was diluted with ethyl acetate and washed successively with 3N hydrochloric acid, water, saturated sodium carbonate solution, and brine. The organic layer was dried over sodium sulfate and evaporated in vacuo. The residue was chromatographed on silica gel using ethyl acetate/hexane (2:1, v/v) as eluent to yield, after crystallization from ethyl acetate/hexane, 30 mg of (4R,7S)-7-tert-butoxycarbonylamino-1,3,4,5,6,7,8,10-octahydro-14-hydroxy-12-methoxy-11-methyl-6,10-dioxo-9, 2,5-benzoxathiaazacyclododecine-4-carboxylic acid allylamide as a white solid.

$^1$H-NMR (250 MHz, DMSO-d$_6$): δ1.82–2.09 (m, 2H) superimposed by 1.93 (s, 3H) and 1.98 (s, 3H); 2.66 (dd, J=13 Hz and 10 Hz, 1H); 3.04–3.22 (m, 3H); 3.59 (d,J=10 Hz, 1H); 3.71(s,3H); 3.73(d,J=10 Hz, 1H); 4.20–4.37 (m, 2H); 4.45(m, 1H); 4.75(m, 1H); 6.52(s, 1H); 8.39(d,J=8 Hz, 1H); 8.68 (t, J=5 Hz, 1H); 9.15 (d, J=7 Hz, 1H); 10.10 (broad s, 1H) ppm

EXAMPLES 85–91

Operating in an analogues manner as described in the previous example, but reacting the product of Example 3 with decylamine, the product of Example 54 with β-alanine methylester, and the product of Example 51 with aminomethyl-cyclohexane, propargyl-amine, (4-trifluoromethyl-benzyl)-amine, ethyl 4-amino-1-piperidine-carboxylate, and cyclopentylamine, respectively, the following compounds were obtained.

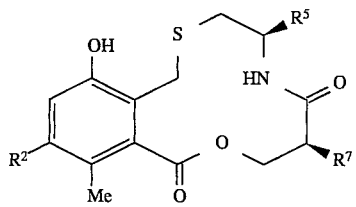

| Example No | R² | R⁵ | R⁷ | ¹H-NMR (250 MHz, DMSO-d₆) δ, inter alia, ppm |
|---|---|---|---|---|
| 85 | OH | CONH(CH₂)₉CH₃ | NHCOOBuᵗ | 1.1–1.5(m, 16H) superimposed by 1.41(s, 9H); 1.89(s, 3H); 2.68(dd, 1H); 2.91–3.13(m, 3H); 3.33(s, 3H); 3.38(d, 1H); 3.89(d, 1H); 4.16(dd, 1H); 4.25(m, 1H); 4.35(m, 1H); 4.96(dd, 1H)6.44(s, 1H); 7.50(d, 1H); 7.84(t, 1H); 7.92(d, 1H); 9.48(s, 1H); 9.50(s, 1H) |
| 86 | OMe | CONH–CH₂–COOMe | NHCOMe | 1.93(s, 3H); 1.96(s, 3H); 2.70(dd, 1H); 3.02(dd, 1H); 3.20–3.44(m, 2H); 3.60 (s, 3H); 3.72(s, 3H); 3.92(d, 1H); 4.06 (dd, 1H); 4.30–4.58(m, 2H); 5.18 (dd, 1H); 6.49(s, 1H); 7.77(d, 1H); 7.88(t, 1H); 8.49(d, 1H); 9.71(s, 1H) |
| 87 | OMe | CONHCH₂–cyclohexyl | NHCOOBuᵗ | 0.85(m, 2H); 1.39(m, 3H); 1.3–1.5 (m, 1H) superimposed by 1.41(s, 9H) 1.93(s, 3H); 2.69(dd, 1H); 2.82–3.10 (m, 3H); 3.38(d, 1H); 3.72(s, 3H); 3.92 (d, 1H); 4.17(dd, 1H); 4.25(m, 1H); 4.47 (m, 1H); 4.96(dd, 1H); 6, 51(s, 1H); 7.49 d, 1H); 7.77–7.97(m, 2H); 9.70(s, 1H) |
| 88 | OMe | CONH–CH=CH₂ | NHCOOBuᵗ | 1.42(s, 9H); 1.93(s, 3H); 2.66(dd, 1H) 3.00(dd, 1H); 3.00(dd, 1H); 3.14(t, 1H) ; 3.43(s, 1H); 3.72(s, 3H); 3.86 (m, 2H); 3.91(d, 1H); 4.17(dd, 1H); 4.29 (m, 1H); 4.49(m, 1H); 4.94(dd, 1H); 6.51 (s, 1H); 7.42(d, 1H); 7.98(d, 1H); 8.38 (t, 1H); 9.71(s, 1H) |
| 89 | OMe | CONHCH₂–C₆H₄–CF₃ | NHCOOBuᵗ | 1.36(s, 9H); 1.93(s, 3H); 2.76(dd, 1H); 3.08(dd, 1H); 3.41(d, 1H); 3.72(s, 3H); 3.85(d, 1H); 4.20(d, 1H); 4.32(m, 1H); 4.40(m, 2H); 4.54(m, 1H); 4.98(dd, 1H); 6.52(s, 1H); 7.46(m, 3H); 7.67(d, 2H); 8.08(d, 1H); 8.52(m, 1H); 9.73(s, 1H) |
| 90 | OMe | CONH–piperidine–N.COOEt | NHCOOBuᵗ | 1.17(t, 3H); 1.41(s, 9H); 1.60–1.78 (m, 2H); 2.68(dd, 1H); 2.80–3.04 (m, 3H); 3.70–3.94(m, 2H) superimposed by 3.72(s, 3H); 4.01(q, 2H); 4.16(dd, 1H); 4.24(m, 1H); 4.46(m, 1H); 4.96(dd, 1H); 6.51(s, 1H); 7.51(d, 1H); 7.85(d, 1H); 7.90(d, 1H); 9.71(s, 1H) |
| 91 | OMe | CONH–cyclopentyl | NHCOOBuᵗ | 1.25–1.87(17H); 1.93(s, 3H); 2.65 (dd, 1H); 2.95(m, 1H); 3.72(s, 3H); 3.85–4.02(m, 2H); 4.14(dd, 1H); 4.22 (m, 1H); 4.43(m, 1H); 4.98(dd, 1H); 6.51(s, 1H); 7.52(d, 1H); 7.76– 7.92(m, 2H); 9.71(s, 1H) |

EXAMPLE 92

A solution of 97 mg of the product of Example 51, 105 mg of triphenylphosphine, and 67 mg of dipyridyl-2,2-disulfide in 2 ml of methylene chloride were stirred at 20° C. for 30 minutes, then 75 mg of 3-amino-1-methoxybenzene were added, and stirring was continued for 1 hour. The mixture was diluted with ethyl acetate and washed successively with 0.1N sodium hydroxyde solution, 1N hydrochloric acid, and with brine. The organic layer was dried over sodium sulfate and evaporated in vacuo. The residue was chromatographed on silica gel using methylene chloride/ethyl acetate (2:1, v/v) as eluent to yield, after crystallization from ethyl acetate/hexane 40 mg of (4R, 7S)-7-tert-butoxycarbonylamino-1,3,4,5,6,7,8,10-octahydro-14-hydroxy-12-methoxy-11-methyl-6,10-dioxo-9,2,5-benzooxathiaazacyclododecine-4-carboxylic acid 3-methoxyphenylamide as a white solid.

¹H-NMR (250 MHz, DMSO-d₆): δ1.42(s,9H); 1.94(s,3H); 2.76(dd, 1H); 3.09(dd, 1H); 3.47(d, 1H); 3.72(s,3H); 3.73(s,3H); 3.99(d, 1H); 4.19(dd, 1H); 4.31(m, 1H); 4.70 (m, 1H); 5.02 (dd, 1H); 6.52 (s, 1H); 6.65 (dd, 1H); 7.05–7.28 (m, 4H); 7.51(d, 1H); 8.05(d, 1H); 9.74(s,1H); 9.95(s, 1H) ppm

EXAMPLE 93

To a solution of 96 mg of the product of Example 51 in 1.6 ml of methylene chloride and 0.5 ml of dimethylformamide were added 36 mg of 1-hydroxy-benzotriazole, and 42 mg of N-(dimethylaminopropyl)-N'-ethylcarbodiimide hydrochloride. The mixture was stirred at 0° C. for 30 minutes, then 16 mg of 2-aminoethanol were added, and stirring was continued at 20° C. for 1.5 hours. The mixture was diluted with ethyl acetate and washed successively with 1N hydrochloric acid, water, saturated sodium bicarbonate solution, and brine. The organic layer was dried over sodium sulfate and evaporated in vacuo. The residue was chromatographed on silica gel using acetone/ethyl acetate (1:1, v/v) as eluent to yield, after crystallization from ethyl acetate/hexane, 84 mg of (4R,7S)-7-tert-butoxycarbonylamino-1,3,4,5,6,7,8,10-octahydro-14-hydroxy-12-methoxy-11-methyl-6,10-dioxo-9,2,5-benzoxathiaazacyclododecine-4-carboxylic acid 2-hydroxyethylamide as a white solid.

¹H-NMR(250 MHz, DMSO-d₆): δ1.41(s,9H); 1.93(s,3H); 2.70(dd, 1H); 3.02(dd, 1H); 3.10(m, 2H); 3.29–3.46(m, 3H); 3.72(s,3H); 3.92(d, 1H); 4.14(dd, 1H); 4.25(m, 1H); 4.48(m, 1H); 4.68(t,1H); 4.96(dd, 1H); 6.48(s, 1H); 7.44(d, 1H); 7.90 (d, 1H); 8.01(t,1H); 9.70(s,1H) ppm

EXAMPLE 94

To a solution of 188 mg of the product of Example 3 in 1.6 ml of methylene chloride and 0.5 ml of dimethylformamide were added 68 mg of 1-hydroxy-benzotriazole, and 86 mg of dicyclohexyl-carbodiimide. The mixture was stirred at 20° C. for 30 minutes, then 45 mg of morpholine were added, and stirring was continued at 20° C. for 2 hours. The precipitate was removed by filtration, the filtrate was diluted with ethyl acetate and washed successively with 3N hydrochloric acid, water, saturated sodium carbonate solution, and with brine. The organic layer was dried over sodium sulfate and evaporated in vacuo. The residue was chromatographed on silica gel using ethyl acetate as eluent to yield, after trituration with ethyl acetate/hexane, 28 mg of tert-butyl (4R, 7S)-1,3,4,5,6,7,8,10-octahydro- 12,14-dihydroxy-4-morpholinocarbonyl-11-methyl-6,10-dioxo-9,2,5-benzoxathiaazacyclododecine-7-carbamate as a white solid.

¹H-NMR(250 MHz, DMSO-d₆): δ1.40(s,9H); 1.91(s,3H); 2.62(dd, 1H); 2.85(dd, 1H); 3.28–3.66 (m, 9H); 3.93 (d, 1H); 4.14 (dd, 1H); 4.28 (m, 1H); 4.80–4.98 (m, 1H); 6.45 (s, 1H); 7.26 (d, 1H); 8.08 (d, 1H); 9.45 (s, 1H); 9.49 (s, 1H) ppm

EXAMPLES 95–99

Operating in an analogues manner as described in the previous example, but reacting the product of Example 3 with diethylamine, the product of Example 51 with glycine methylester hydrochloride, sarcosine ethylester hydrochloride, and with 2-(3-methyl-1,2,4-oxadiazol-5-yl)-ethylamine p-toluenesulfonate, and the product of Example 55 with 2-(3-methyl-1,2,4-oxadiazol-5-yl)-ethylamine p-toluenesulfonate, the following compounds were obtained. (If the amino component was added in the form of its hydrochloride or 4-toluene-sulfonate salt (Examples 96–99), 1 equivalent of 4-dimethylaminopyridine was added to the reaction mixture):

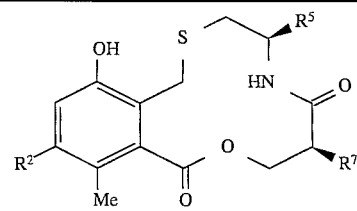

| Example No | R² | R⁵ | R⁷ | ¹H-NMR (250 MHz, DMSO-d₆) δ, inter alia, ppm |
|---|---|---|---|---|
| 95 | OH | CON(Et)₂ | NHCOOBuᵗ | 0.99(t, 3H); 1.10(t, 3H); 1.38(s, 9H); 1.91(s, 3H); 2, 61(dd, 1H); 2.85 (dd, 1H); 3.10–3.40m, 4H); 3.66(d, 1H); 3.98(d, 1H); 4.11(dd, 1H); 4.34(m, 1H); 4.87(m, 1H); 4.98(dd, 1H); 6.45(s, 1H); 7.37(d, 1H); 7.98(d, 1H); 9.45(s, 1H); 9.49(s, 1H) |
| 96 | OMe | CONHCH₂COOMe | NHCOOBuᵗ | 1.40(s, 9H); 1.93(s, 3H); 6.67(dd, 1H) 3.03(dd, 1H); 3.42(d, 1H); 3.62(s, 3H); 3.72(s, 3H); 3.85(m, 2H); 3.92(d, 1H); 4.16(m, 1H); 4.30(m, 1H); 4.56(m, 1H); 4.94(dd, 1H); 6.50(s, 1H); 7.39(d, 1H); 7.95(d, 1H); 8.48(t, 1H); 9.70(s, 1H) |
| 97 | OMe | CON—CH₂COOEt<br>\|<br>Me | NHCOOBuᵗ | 1.17(t, 3H); 1.39(s, 9H); 1.93(s, 3H); 3.03(s, 3H); 3.73(s, 3H); 2.91–4.16 (m, 3H); 4.28(m, 1H); 4.97(m, 1H); 5.57 (dd, 1H); 6.50(s, 1H); 7.35(d, 1H); 7.91 (d, 1H):9.66(s, 1H) |

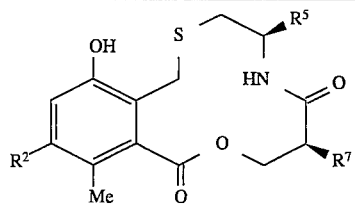

| Example No | R² | R⁵ | R⁷ | ¹H-NMR (250 MHz, DMSO-d₆) δ, inter alia, ppm |
|---|---|---|---|---|
| 98 | OMe | CONH—⟨CH₂CH₂⟩—(3-methyl-1,2,4-oxadiazol-5-yl) | NHCOOBuᵗ | 1.41(s, 9H); 1.93(s, 3H); 2.31(s, 3H); 2.62(dd, 1H); 2.88–3.08(m, 3H); 3.28–3.56(m, 3H); 3.72(s, 3H); 3.92(d, 1H); 4.15(dd, 1H); 4.27(m, 1H); 4.45(m, 1H) 4.95(dd, 1H); 6.51(s, 1H); 7.42(d, 1H); 7.91(d, 1H)8.22(t, 1H); 9.67(s, 1H) |
| 99 | OMe | CONH—⟨CH₂CH₂⟩—(3-methyl-1,2,4-oxadiazol-5-yl) | NHCHO | 1.93(s, 3H); 2.31(s, 3H); 2.66(dd, 1H); 2.96–3.10(m, 3H); 3.33–3.58(m, 3H); 3.72(s, 3H); 3.88(d, 1H); 4.07(dd, 1H); 4.39(m, 1H); 4.58(m, 1H); 5.20(dd, 1H); 6.52(s, 1H); 7.84(d, 1H); 8.10(m, 1H); 8.17(s, 1H); 8.69(d, 1H); 9.73(s, 1H) |

The starting material used in the Examples 98 and 99 was prepared as follows:

(a) A solution of 0.72 g of acetamide oxime in 60 ml of ethanol was treated with 0.6 g of a 55% dispersion of sodium hydride in mineral oil, and then stirred for 5 minutes at 20° C. To the solution were added 2.07 g of methyl 3-tritylamino-propanoate, and the mixture was heated at reflux for 2 hours. The solvent was evaporated in vacuo and the residue was partitioned between ethyl acetate and 10% sodium chloride solution. The organic layer was dried over sodium sulfate, evaporated in vacuo, and the residue was chromatographed on silica gel using ethyl acetate/hexane (1:5, v/v) as eluent to give 1.24 g of [2-(3-methyl-1,2,4-oxadiazol-5-yl)-ethyl]-trityl-amine as white crystals, m.p. 100°–101° C. (from ethyl acetate/hexane).

(b) A solution of 370 mg of [2-(3-methyl-1,2,4-oxadiazol-5-yl)-ethyl]-trityl-amine and 190 mg of p-toluene-sulfonic acid in 10 ml of ethanol was heated to 60° C. for 2 hours. The solvent was evaporated and the residue was triturated with diethylether/hexane to give 2-(3-methyl-1,2,4-oxadiazol-5-yl)ethylamine p-toluene-sulfonate as white crystals of m.p. 122°–123° C.

EXAMPLE 100

A mixture of 0.71 g of tert-butyl (4R, 7S)-12,14-bis(tert-butyldimethylsilyloxy)-1,3,4,5,6,7,8,10-octahydro-4-methoxycarbonyl-11-methyl-6,10-dioxo-9,2,5-benzoxathiaaza-cyclododecine-7-carbamate and 0.44 g 2,4-bis-(4-methoxyphenyl)-2,4-dithioxo-1,3,2,4-dithiaphosphetane in 6 ml of toluene was heated to 80° C. for 1 hour. The solvent was evaporated in vacuo, and the residue was chromatographed on silica gel using ethyl acetate/methylene chloride/hexane (1:1:1, v/v/v) as eluent. The bis-(tert-butyldimethyl-silylated)-product obtained was treated with ammonium fluoride in methanol in an analogous manner to the procedure described in Example 13 to yield, after crystallization from diethylether/hexane, 270 mg of tert-butyl (4R, 7S)-1,3,4,5,6,7,8,10-octahydro-12,14-dihydroxy-4-methoxycarbonyl-11-methyl-10-oxo-6-thioxo-9,2,5-benzooxahiaazacyclododecine-7-carbamate as a white solid.

¹H-NMR (250 MHz, DMSO-d₆): δ1.41 (s, 9H); 1.91 (s, 3H); 3.04 (d, 1H); 3.14 (m, 1H); 3.30(m, 1H); 3.66 (s, 3H); 3.94 (d, 1H); 4.28 (dd, 1H); 4.69 (m, 1H); 4.91 (m, 1H); 5.12 (m, 1H); 6.43(s,1H); 7.70(broad s, 1H); 9.49(s, 1H); 9.50(s,1H); 9.55 (d, 1H) ppm

EXAMPLE 111

Using the (tert-butyldimethylsilylated)-product of Example 31 as starting material and operating in an analogues manner as described in the previous example, there was obtained methyl (4R)-1,3, 4, 5, 6, 7,8,10-octahydro-14-hydroxy-12-methoxy-10-oxo-6-thioxo-9,2,5-benzoxathi-aazacyclododecine-4-carboxylate as a white solid.

¹H-NMR (400 MHz, DMSO-d₆): δ2.85–2.95 (m, 2H); 3.20 (dd, 1H); 3.36 (m, 1H); 3.69 (s, 3H); 3.71 (s, 3H); 3.84 (d, 1H); 4.30 (d, 1H); 4.49 (m, 1H); 4.69 (m, 1H); 5.40 (m, 1H); 6.59 (d, 1H); 6.77 (d, 1H); 10.06 (s, 1H); 10.76 (d, 1H) ppm

EXAMPLE 102

Using the 14-(tert-butyldimethylsilylated)-product of Example 67 as starting material and operating in an analogues manner as described in Example 100, there was obtained, after crystallization from ethyl acetate/hexane, ethyl (4R,7S)1,3,4,5,6,7,8,10-octahydro-14-hydroxy-12-methoxy-11-methyl-6,10-dioxo-7-thioacetamido-9,2,5-benzoxathiaazacyclododecine-4-carboxylate as a white solid.

¹H-NMR(250 MHz, DMSO-d₆): δ1.16 (t, 3H); 1.94 (s, 3H); 2.52 (s, 3H); 2.93 (dd, 1H); 3.08 (dd, 1H); 3.64 (d, 1H); 3.72(s,3H); 3.81(d, 1H); 4.07(q,2H); 4.23(dd, 1H); 4.31(m, 1H); 5.22 (dd, 1H); 5.35 (m, 1H); 6.52 (s, 1H); 8.47 (d, 1H); 9.74 (s, 1H); 10.28 (d, 1H) ppm

EXAMPLE 103

As a second product from the procedure described in the previous example, there was obtained, upon crystallization from ethyl acetate/hexane, ethyl (4R,7S)-1,3,4,5,6,7,8,10-octahydro-14-hydroxy-12-methoxy-11-methyl-10-oxo-7-thioacetamido-6-thioxo- 9,2,5-benzoxathiaazacyclodode-cine-4-carboxylate as a white solid.

¹H-NMR (250 MHz, DMSO-d₆): 1.16 (t, 3H); 1.95 (s, 3H); 2.55 (s, 3H); 3.18–3.25 (m, 2H ); 3.31 (dd, 1H); 3.72 (s, 3H); 3.94 (d, 1H); 4.08 (m, 2H); 4.36 (dd, 1H); 5.01 (m, 1H); 5.23 (dd, 1H); 5.60(m, 1H); 6.50(s,1H); 9.62(d, 1H); 9.76(s,1H); 10.33 (d, 1H) ppm

EXAMPLE 104

A sample of 270 mg of tert-butyl (4R, 7S)-12,14-bis-(tertbutyldimethylsilyloxy)-4-carbamoyl-1,3,4,5,6,7,8,10-octahydro11-methyl-6,10-dioxo-9,2,5-benzoxathiaazacyclododecine-7-carbamate was subjected in an analogues manner to the procedure described in Example 100, and the crude reaction product was treated with ammonium fluoride in methanol in an analogous manner to the procedure described in Example 13, to yield, after chromatographic purification on silica gel using ethyl acetate/hexane (1:1, v/v) as eluent, and crystallization from ethyl acetate/hexane, 86 mg of (4R, 7S)-7-(tert-butoxycarbonylamino)-1,3,4,5,6,7,8,10-octahydro-12,14-dihydroxy-11-methyl-6,10-dioxo-9,2,5-benzoxathiaazacyclododecine-4-thiocarboxamide as a white solid.

¹H-NMR(250 MHz, DMSO-d₆): δ1.41 (s, 9H); 1.90 (s, 3H); 2.73 (dd, 1H); 3.11 (dd, 1H); 3.36 (d, 1H); 3.92 (d, 1H); 4.15 (dd, 1}{); 4.19 (m, 1H); 4.73 (m, 1H); 5.02 (dd, 1H); 6.45 (s, 1H); 7.60 (d, 1H); 8.00 (d, 1H); 9.16 (s, 1H); 9.48 (s, 1H); 9.51 (s, 1H); 9.79 (s,1H) ppm The starting material used above was prepared as follows:
(a) The product of Example 78 was subjected in an analogous manner to the procedure described in Example 13 (d) to yield tert-butyl (4R, 7S)-12,14-bis-(tert-butyldimethylsilyloxy)-4-carbamoyl-1,3,4,5,6,7,8,10-octahydro-11-methyl-6,10-dioxo-9,2,5-benzoxathiaazacyclododecine-7 -carbamate.

EXAMPLE 105

A solution of 28 mg of the product of Example 127 in 0.44 ml of trifluoroacetic acid was stirred at 0° C. for 30 minutes. The solvent was evaporated in vacuo, and the residue was taken up in 2 ml of 1M pH7 sodium phosphate buffer. The pH was adjusted to 8.5 by the addition of 1N sodium hydroxide solution, and the solution was then chromatographed on MCI-Gel CHP20P using 0–40% aqueous acetonitrile as eluent. The product-containing fractions were combined and lyophilized to give 19 mg of [(4R,7S)-7-[(N-L-alanyl-1-alanyl)-amino]-1,3,4,5,6,7,8,10-octahydro-12, 14-dihydroxy-11-methyl-6,10-dioxo-9,2,5-benzoxathiaazacyclododecin-4-yl]-methyl acetate as a white powder.

¹H-NMR (250 MHz, DMSO-d₆): δ1.10(d,3H); 1.29(d, 3H); 1.88(s,3H); 1.99(s,3H); 2.90(dd, 1H); 3.52 (d, 1H); 3.56–3.73 (m, 2H); 3.96–4.27 (m, 6H); 4.55 (m, 1H); 5.04 (dd, 1H); 6.45(s,1H); 7.51(d, 1H); 8.14(d, 1H); 9.53(broad s,2H) ppm

EXAMPLE 106

A solution of 120 mg of the 14-(tert-butyldimethylsilylated)product of Example 21 in 2 ml of trifluoroacetic acid was stirred at 0° C. for 1 hour. The solvent was evaporated in vacuo, and the residue was taken up in 4 ml of methanol. After the addition of 40 mg of ammonium fluoride, the mixture was stirred at 20° C. for 1 hour. The solvent was evaporated in vacuo, and the residue was taken up in 2 ml of 1M pH7 sodium phosphate buffer. The pH was adjusted to 8.5 by the addition of 1N sodium hydroxide solution, and the solution was then chromatographed on MCI-Gel CHP20P using 0–30% aqueous acetonitrile as eluent. The product-containing fractions were combined and lyophilized to give 18 mg of methyl [(4R, 7S)-7-amino-1,3,4,5,6,7,8, 10-octahydro-14-hydroxy-12-methoxy-11-methyl-6,10-dioxo-9,2,5-benzoxathiaazacyolododecine-4-carboxylate as a white powder.

¹H-NMR (250 MHz, DMSO-d₆): δ1.91 (S, 3H); 2.87 (dd, 1H); 3.09 (dd, 1H); 3.43 (d, 1H); 3.66 (s, 3H); 3.72 s, 3H); 3.86 (d, 1H); 4.12 (dd, 1H); 4.64 (m, 1H); 5.14 (dd, 1H); 6.51 (s,1H); 8.43(d, 1H); 9.70(s,1H) ppm

EXAMPLES 107–111

Using as starting material the products of Examples 78 and 94, the 14-(tert-butyldimethylsilylated)-product of Example 28, and the 12,14-bis-(tert-butyldimethylsilylated)-products of Examples 18 and 58, and operating in an analogues manner as described in Examples 105 and 106, the following compounds were obtained:

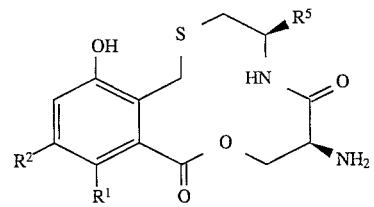

| Example No | R¹ | R² | R⁵ | ¹H-NMR (250 MHz, DMSO-d₆) δ,inter alia, ppm |
|---|---|---|---|---|
| 107 | Me | OH | CONH₂ | 1.87(s, 3H); 2.73(dd, 1H); 3.03(dd, 1H); 3.55–3.68(m, 3H); 3.87(d, 1H); 4.11 (dd, 1H); 4.45(m, 2H); 5.15(dd, 1H); 6.45 (s, 1H); 7.23(s, 1H); 7.49(s, 1H); 8.24 (d, 1H); 9.52(broad s, 1H) |
| 108 | Me | OH | CON⟨⟩O | in D₂O: δ 2.03(s, 3H); 2.85(dd, 1H); 3.14(dd, 1H); 3.45–4.00(m, 10H); 4.40 (dd, 1H); 5.13(dd, 1H); 5.31(dd, 1H); 6.54(s, 1H) |
| 109 | H | OMe | COOMe | 2.32(broad s, 2H); 2.86(dd, 1H); 3.05 dd, 1H); 3.66 (s, 3H); 3.82(d, 1H); 4.17 |

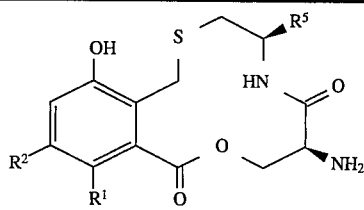

| Example No | R¹ | R² | R⁵ | ¹H-NMR (250 MHz, DMSO-d₆) δ, inter alia, ppm |
|---|---|---|---|---|
| 110 | H | OH | COOMe | (dd, 1H); 4.34(d, 1H); 4.71(m, 1H); 4.83 (dd, 1H); 6.49(d, 1H); 6.69(d, 1H); 8.59 (d, 1H); 9.64(s, 1H); 9.84(s, 1H) 2.89(dd, 1H); 3.06(dd, 1H); 3.66(s, 3H); 3.71(s, 3H); 3.84(d, 1H); 4.18(dd, 1H); 4.36(d, 1H); 4.71(m, 1H); 4.85(dd, 1H); 6.60(d, 1H); 6.79(d, 1H); 8.60(d, 1H); 10.06(broad s, 1H) |
| 111 | Me | OH | CH₂OH | 1.87(s, 3H); 2.20(broad s, 2H); 2.51 (dd, 1H); 2.89(dd, 1H); 3.34–3.49 (m, 3H); 3.56(broad s, 1H); 3.78 (d, 1H); 3.94(m, 1H); 4.07(dd, 1H); 4.81 (t, 1H); 5.16(dd, 1H); 6.43(s, 1H); 7.83 (d, 1H); 9.44(s, 1H); 9.47(s, 1H) |

EXAMPLE 112

To a solution of 1.30 g of methyl (4R, 7S)-7-amino-12, 14-bis(tert-butyldimethylsilyloxy)-1,3,4,5,6,7,8,10-octahydro-6,10-dioxo-9,2,5-benzoxathiaazacyclododecine-4 -carboxylate and 0.23 g of triethylamine in 50 ml of methylene chloride, was added at 0° C. within 2 minutes a solution of 0.25 g of chloro-acetyl chloride in 3 ml of methylene chloride. The mixture was stirred at 0° C. for 30 minutes, then diluted with methylene chloride and washed successively with 0.03N hydrochloric acid and water. The organic layer was dried over sodium sulfate and evaporated in vacuo. The residue was chromatographed on silica gel using ethyl acetate/hexane (1:1, v/v) as eluent to yield 1.20 g of methyl (4R, 7S)-12,14-bis (tert-butyldimethylsilyloxy)-7-(2-chloroacetamido)-1,3,4,5,6,7,8,10-octahydro-6,10-dioxo-9,2,5-benzoxathiaazacyclododecine-4-carboxylate as a white solid. A sample of 287 mg of this material was treated with ammonium fluoride in methanol in an analogous manner to the procedure described in Example 13 to yield, after crystallization from ethyl acetate, 115 mg of methyl (4R, 7S)-7-(2chloroacetamido)-1,3,4,5,6,7,8,10-octahydro-12, 14-dihydroxy6,10-dioxo-9,2,5-benzoxathiaazacyclododecine-4 -carboxylate as a white solid, m.p. 182° C. (dec.).

¹H-NMR (250 MHz, DMSO-d₆): δ2.87(dd, 1H); 3.11(dd, 1H); 3.63(S,3H); 3.90(d, 1H); 4.15–4.33(m, 2H) superimposed by 4.23 (s, 2H); 4.50–4.68 (m, 2H); 4.87 (dd, 1H); 6.52 (dd, 1H); 6.73 (dd, 1H); 8.53 (d, 1H); 8.70 (d, 1H); 9.63 (s, 1H); 9.83 (s, 1H) ppm The starting material used above was prepared as follows:

(a) tert-Butyl (4R, 7S)-12, 14-bis (tert-butyldimethylsilyloxy)-1,3,4,5,6,7,8,10-octahydro-4-methoxycarbonyl-6,10-dioxo-9,2,5-benzoxathiaazacyclododecine-7-carbamate was subjected in an analogous manner to the procedure described in Example 14 (a) to give methyl (4R, 7S)-7-amino-12, 14-bis (tert-butyldimethylsilyloxy)- 1,3,4,5,6,7,8,10-octahydro-6,10-dioxo-9,2,5-benzoxathiaazacyclododecine-4-carboxylate.

EXAMPLE 113

A solution of 45 mg of methyl (4R, 7S)-7-(2-chloroacetamido)-1,3,4,5,6,7,8,10-octahydro-12,14-dihydroxy-6,10-dioxo-9,2,5-benzoxathiaazacyclododecine-4-carboxylate in 0.5 ml of morpholine was stirred at 20° C. for 15 minutes. The solution was evaporated in vacuo, and to the residue were added 5 ml of 0.1N hydrochloric acid, a white precipitate forming immediately. The precipitate was isolated by centrifugation, washed with water and dried to yield 33 mg of methyl 4-[(4R, 7S)-1,3,4,5,6,7,8,10-octahydro-12, 14-dihydroxy-4-methoxycarbonyl-6,10-dioxo-9,2,5-benzoxathiaazacyclododecin-7-yl-carbamoyl-methyl]-morpholine hydrochloride as a white solid.

¹H-NMR(250 MHz,DMSO-d₆): δ2.45 (m, 4H); 2.93 (dd, 1H); 3.02 (d, 1H); 3.10 (d, 1H); 3.14 (dd, 1H); 3.50(m, 1H); 3.63(s,3H); 3.88(d, 1H); 4.09(d, 1H); 4.29(dd, 1H); 4.48 (m, 1H); 4.68 (m, 1H); 4.86 (dd, 1H); 6.50 (d, 1H); 6.63 (d, 1H); 8.25 (d, 1H); 8.45(d, 1H); 9.64(s,1H); 9.85(s,1H) ppm

EXAMPLE 114–116

By operating in an analogues manner as described in the previous example, but replacing morpholine by 1-methylpiperidine, pyridine or by 1,4-diazabicyclo[2.2.2]octane, the following compounds were obtained.

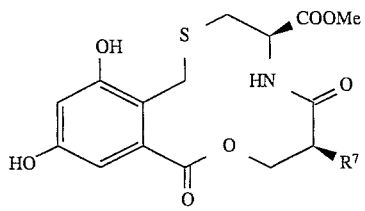

| Example No | R7 | $^1$H-NMR (250 MHz, DMSO-d$_6$) δ, inter alia, ppm |
|---|---|---|
| 114 | NHCOCH$_2$—N⌢N— .HCl | 2.65(s, 3H); 2.94(dd, 1H); 3.15(dd, 1H); 3.20 (s, 2H); 3.63(s, 3H); 3.89(d, 1H); 4.16 (d, 1H); 4.26(dd, 1H); 4.49(m, 1H); 4.68 (m, 1H); 4.87(m, 1H); 6.56(d, 1H); 6.67 (d, 1H); 8.34(d, 1H); 8.54(d, 1H); 9.70 (s, 1H); 9.93(s, 1H); 10.41 (broad s, 1H) |
| 115 | NHCOCH$_2$—$^+$N⌢(pyridinium) Cl$^-$ | 3.03(dd, 1H); 3.16(dd, 1H); 3.61(s, 3H); 4.00 (d, 1H); 4.25(dd, 1H); 4.40(d, 1H); 4.50–4.67 (m, 2H); 4.94(dd, 1H); 5.56(d, 1H); 5.80 (d, 1H); 6.60(d, 1H); 6.75(d, 1H); 8.22 (t, 2H); 8.68(t, 1H); 8.87(d, 1H); 9.08 (d, 2H); 9.39(d, 1H); 9.73(s, 1H); 9.97(s, 1H) |
| 116 | NHCOCH$_2$—$^+$N⌢N Cl$^-$ | 2.90–3.16(m, 8H); 3.39–3.60(m, 6H); 3.61 (s, 3H); 3.95(d, 1H); 4.12–4.30(m, 3H); 4.37 (d, 1H); 4.61(m, 1H); 4.71(m, 1H); 4.94 (dd, 1H); 6.60(d, 1H); 6.73(d, 1H); 8.75 (d, 1H); 9.33(d, 1H); 9.73(s, 1H); 9.98(s, 1H) |

EXAMPLE 117

A solution of 51 mg of methyl (4R, 7S)-7-(2-chloroacetamido)-1,3,4,5,6,7,8,10-octahydro-12,14-dihydroxy-6,10-dioxo-9,2,5-benzoxathiaazacyclododecine-4-carboxylate, 18 mg of tetrahydro-2-methyl-3-thioxo-as-triazine-5,6-dione, and 12 mg of triethylamine in 1 ml of dimethylformamide was stirred for 4 days at 20° C. The solvent was evaporated in vacuo, and the residue was taken up in 20% aqueous acetonitrile and chromatographed on MCI-Gel CHP20P using 0–30% aqueous acetonitrile as eluent. The product-containing fractions were combined and lyophilized to give 32 mg of methyl (4R, 7S)-7-[2-[((2,5-dihydro-6-hydroxy-2-methyl-5-oxo-as-triazin-3-yl)thio]acetamido]-1, 3,4,5,6,7,8,10-octahydro-12,14-dihydroxy-6,10-dioxo-9,2, 5-benzoxathiaazacyclododecine-4-carboxylate as a white solid.

$^1$H-NMR(250 MHz, DMSO-d$_6$): δ3.09 (m, 2H); 3.53 (s, 3H); 3.64 (s, 3H); 3.94 (d, 1H): 4.04 (d, 1H); 4.10 (d, 1H); 4.20(d, 1H); 4.47(d, 1H); 4.57(m, 1H); 4.76(m, 2H); 4.87 (dd, 1H); 6.54 (d, 1H); 6.80 (d, 1H); 7.84 (d, 1H); 9.07 (d, 1H); 9.64 (s, 1H); 9.84 (s, 1H) ppm

EXAMPLE 118

To a mixture of 245 mg of methyl (4R, 7S)-7-amino-12, 14-bis (tert-butyldimethylsilyloxy)-11-methyl-1,3,4,5,6,7,8, 10-octahydro-6,10-dioxo-9,2,5-benzoxathiaazacyclododecine-4-carboxylate and 102 mg of 3[N-(tert-butoxycarbonyl)methylamino]-propionic acid in 6 ml of acetonitrile, cooled to 0° C., were added 95 mg of N-(dimethylaminopropyl)-N'-ethylcarbodiimide hydrochloride. The mixture was stirred at 0° C. for 3 hours, and then diluted with ethyl acetate and washed successively with 3N hydrochloric acid, water, saturated sodium carbonate solution, and brine. The organic layer was dried over sodium sulfate and evaporated in vacuo. The residue was dissolved in 5 ml of cold trifluoroacetic acid, and the solution was stirred at 0° C. for 30 minutes. The solvent was evaporated in vacuo, the residue was taken up in ethyl acetate, and the solution was washed with saturated sodium bicarbonate solution, and with brine. The organic layer was dried over sodium sulfate end evaporated in vacuo. The residue was treated with ammonium fluoride in methanol in an analogous manner to the procedure described in Example 13. The resulting product was purified by chromatography on MCI-Gel CHP20P which had been pretreated with 1% aqueous acetic acid. Using 0–20% aqueous acetonitrile as eluent, there were obtained, alter lyophilization of the product-containing fractions, 49 mg of methyl (4R, 7S)-1,3,4,5,6,7,8,10-octahydro-12,14-dihydroxy-11-methyl-7-[3-(methylamino)propionamido]-6,10-dioxo-9,2,5-benzo oxathiaazacyclododecine-4-carboxylate acetate as a white solid.

$^1$H-NMR (250 MHz,DMSO-d$_6$): δ1.89 (s, 3H), 2.24 (s, 3H); 2.66–2.82 (m, 3H); 3.09 (dd, 1H); 3.55 (d,1H); 3.63(s, 3H); 3.86(d,1H); 4.05(dd, 1H)4.62(m, 1H); 5.35 (dd, 1H); 6.46 (s, 1H); 8.51 (d, 1H); 8.65 (d, 1H) ppm

EXAMPLE 119

A solution of 63 mg of methyl (4R,7S)-7-amino-14-(tert-butyldimethylsilyloxy)-1,3,4,5,6,7,8,10-octahydro-12-methoxy-11-methyl-6,10-dioxo-9,2,5-benzoxathiaazacyclododecine-4-carboxylate and 20 ml of pyridine in 2 ml of acetic anhydride was heated to 60° C. for 1 hour. The solution was evaporated in vacuo, the residue was dissolved in ethyl acetate, and the solution was washed with saturated sodium bicarbonate solution, and with brine. The organic layer was dried over sodium sulfate and evaporated in vacuo. The residue was treated with ammonium fluoride in methanol in an analogous manner to the procedure described in Example 13 to yield, after crystallization from methanol/ ethyl acetate/hecate, 30 mg of methyl (4R, 7S)-7-acetylamino-1,3,4,5,6,7,8,10-octahydro-14-hydroxy-12-methoxy-11-methyl-6,10-dioxo-9,2,5-benzoxathiaazacyclododecine-4-carboxylate as a white solid.

$^1$H-NMR (250 MHz, DMSO-d$_6$): δ1.94 (s, 6H): 2.87 (dd, 1H); 3.08 (dd, 1H); 3.54 (d, 1H); 3.63 (s, 3H); 3.72 (s,3H); 3.80(d, 1H); 4.11(dd,1H); 4.45(m, 1H); 4.67(m, 1H); 5.10 (dd, 1H); 6.51 (s,1H); 8.27(d, 1H); 9.73 (s, 1H)ppm The starting material used above was prepared as follows:

(a) The 12,14-bis (tert-butyldimethylsilylated)-product of Example 21 was subjected in an analogous manner to the procedure described in Example 14 (a) to give methyl (4R, 7S)-7-amino-14-(tert-butyldimethylsilyloxy)-1,3,4,5,6,7,8,10-octahydro-12-methoxy-11-methyl-6,10-dioxo-9,2,5-benzoxathiaazacyclododecine-4-carboxylate.

EXAMPLE 120

A sample of 156 mg of the product of Example 14(a) was subjected in an analogues manner to the procedure described in Example 119 to give, after crystallization from acetone/hexane, 79 mg of methyl (4R,7S)-7-acetylamino-1,3,4,5,6,7,8,10-octahydro-12,14-dihydroxy-11-methyl-6,10-dioxo-9,2,5-benzoxathiaazacyclododecine-4-carboxylate as a white solid.

$^1$H-NMR(250 MHz, DMSO-d$_6$): δ1.90(s,3H); 1.94(s,3H); 2.89(dd, 1H); 3.10(dd, 1H); 3.50(d, 1H); 3.63 (s, 3H); 3.77 (d, 1H); 4.09 (dd, 1H); 4.45 (m, 1H); 4.67 (m, 1H); 5.10 (dd, 1H); 6.45(s,1H); 8.26(d, 1H); 8.29(d, 1H); 9.49(s,1H); 9.51(s,1H) ppm

EXAMPLE 121

The 12,14-bis(tert-butyldimethylsilylated)-Product of Example 108 was subjected in an analogues manner to the procedure described in Example 119 to give N-[(4R, 7S)-1,3,4,5,6,7,8,10-octahydro-12,14-dihydroxy-11-methyl-4-(morpholinocarbonyl)-6,10-dioxo-9,2,5-benzoxathiaazacyclododecin-7-yl]acetamide as a white solid.

$^1$ H-NMR (250 MHz, DMSO-d$_6$): δ1.91(s,3H); 1.94(s,3H); 2.75(dd, 1H); 2.89(dd, 1H); 3.22–3.70 (m, ~5H); 3.96 (d, 1H); 4.03 (dd, 1H); 4.55 (m, 1H); 4.87 (m, 1H); 5.17 (dd, 1H); 6.48 (s, 1H); 8.02 (d, 1H); 8.28 (d, 1H); 9.57 (broad s, 1H) ppm

EXAMPLE 122

To a mixture of 61 mg of methyl (4R,7S)-7-amino-12,14-bis-(tert-butyldimethylsilyloxy)-11-methyl-1,3,4,5,6,7,8,10-octahydro-6,10-dioxo-9,2,5-benzoxathiaazacyclododecine-4-carboxylate and 16 mg of 3-methoxypropionic acid in 2 ml of acetonitrile, cooled to 0° C., were added 29 mg of N-(dimethylaminopropyl)-N'-ethylcarbodiimide hydrochloride. The mixture was stirred at 0° C. for 3 hours, and then diluted with ethyl acetate and washed successively with 3N hydrochloric acid, water, 5% sodium bicarbonate solution, and with brine. The organic layer was dried over sodium sulfate and evaporated in vacuo. The residue was chromatographed on silica gel using ethyl acetate/hexane (1:1, v/v) as eluent, and the (tert-butyldimethylsilylated)-product obtained was treated with ammonium fluoride in methanol in an analogous manner to the procedure described in Example 13 to yield, after crystallization from ethyl acetate/hexane, 24 mg of methyl (4R, 7S)-7-(3-methoxypropionylamino)-1,3,4,5,6,7,8,10-octahydro-12,14-dihydroxy-11-methyl-6,10-dioxo-9,2,5-benzoxathiaazacyclododecine-4-carboxylate as a white solid.

$^1$H-NMR(250 MHz, DMSO-d$_6$): δ1.90 (s, 3H); 2.48 {m, 2H ); 2.84(dd, 1H); 3.09(dd, 1H); 3.21(s,3H); 3.49 (d, 1H); 3.55 (t, 1H); 3.62(s,3H); 3.76(d, 1H); 4.08(dd, 1H); 4.44 (m, 1H); 4.67 (m, 1H); 5.07 (dd, 1H); 6.45 (s, 1H); 8.14 (d, 1H); 8.32 (d, 1H); 9.45 (s, 1H); 9.52 (s, 1H) ppm

EXAMPLE 123–129

Operating in an analogues manner as described in the previous example, the product of Example 14 (a) was acylated with trans-N-(tert-butoxycarbonyl)-4-hydroxy-L-proline, N-(tert-butoxycarbonyl)-L-threonine, 3-cyclopentyl-propionic acid, and with 3-phenyl-propionic=acid, the 12,14-bis-(tert-butyldimethylsilylated)-product of Example 64 was first treated with trifluoroacetic acid in an analogues manner as described in Example 105 and the resulting product was acylated with N-(tert-butoxycarbonyl)-L-alanyl-L-alanine, the product of Example 119(a) was acylated with cyclopropane-carboxylic acid and with 3,4-dihydroxy-cinnamic acid, yield the following compounds:

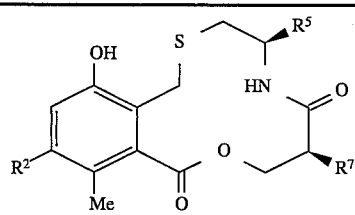

| Example No | R2 | R5 | R7 | $^1$H-NMR (250 MHz, DMSO-d$_6$) δ, inter alia, ppm |
|---|---|---|---|---|
| 123 | OH | COOMe | COOBu$^t$ N NHCO—⟨ H ⟩–OH | 1.31(s, 9H); 1.78–2.00(m, 1H) superimposed by 1.90(s, 3H); 2.00–2.20 (m, 1H); 2.80–3.14(m, 2H); 3.30–3.50 (m, 3H); 3.62(s, 3H); 3.80(d, 1H); 4.12 (m, 1H); 4.24(m, 1H); 4.33(m, 2H); 4.68 (m, 1H); 4.95(m, 1H); 5.02(d, 1H); 6.45 (s, 1H); 8.20(d, 1H); 8.52(d, 1H); 9.51 (s, 1H); 9.53(s, 1H) |

-continued

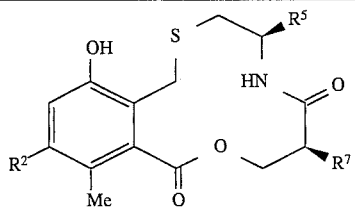

| Example No | R2 | R5 | R7 | ¹H-NMR (250 MHz, DMSO-d₆) δ, inter alia, ppm |
|---|---|---|---|---|
| 124 | OH | COOMe | NHCO−CH(H)−CH(Me)(OH), NHCOOBuᵗ on α-C | 1.04(d, 3H); 1.37(s, 9H); 1.90(s, 3H); 2.72(dd, 1H); 3.12(dd, 1H); 3.48(d, 1H); 3.60(s, 3H); 3.73(d, 1H); 4.00(m, 1H); 4.11(dd, 1H); 4.21(m, 1H); 4.45(m, 1H); 4.68(m, 1H); 5.13(d, 1H); 5.22(m, 1H); 6.47(s, 1H); 6.54(d, 1H); 8.21(d, 1H); 8.34(d, 1H); 9.54(s, 1H); 9.56(s, 1H) |
| 125 | OH | COOMe | NHCO−CH₂−cyclopentyl | 0.96–1.16(m, 2H); 1.40–1.80(m, 10H); 1.90(s, 3H); 2.24(m, 2H); 2.87(dd, 1H); 3.06(dd, 1H); 3.47(d, 1H); 3.62(s, 3H); 3.77(d, 1H); 4.10(dd, 1H); 4.40(m, 1H); 4.64(m, 1H); 5.00(dd, 1H); 6.45(s, 1H); 8.18(d, 1H); 8.24(d, 1H); 9.50(s, 1H); 9.52(s, 1H) |
| 126 | OH | COOMe | NHCO−CH₂−Ph | 1.90(s, 3H); 2.53(m, 2H); 2.75–2.95 (m, 3H); 3.08(dd, 1H); 3.48(d, 1H); 3.62 (s, 3H); 3.74(d, 1H); 4.03(dd, 1H); 4.38 (m, 1H); 4.65(m, 1H); 5.01(dd, 1H); 6.45 (s, 1H); 7.10–7.30(m, 5H); 8.23(d, 1H); 8.30(d, 1H); 9.50(s, 1H); 9.52(s, 1H) |
| 127 | OH | CH₂OAc | NHCO−CH(Me)−NH−CO−CH(Me)−NHCOOBuᵗ | 1.12(d, 3H); 1.26(d, 3H); 1.35(s, 9H); 1.89(s, 3H); 1.99(s, 3H); 2.90(dd, 1H); 3.49(d, 1H); 3.74(d, 1H); 3.88–4.06 (m, 4H); 4.14(dd, 1H); 4.26(m, 1H); 4.57 (m, 1H); 5.05(dd, 1H); 6.45(s, 1H); 6.91 (d, 1H); 7.57(d, 1H); 8.06(d, 1H); 8.14 (d, 1H); 9.49(s, 1H); 9.51(s, 1H) |
| 128 | OMe | COOMe | NHCO−cyclopropyl | 0.70(m, 4H); 1.83(m, 1H); 1.94(s, 3H); 2.93(dd, 1H); 3.10(dd, 1H); 3.57(d, 1H); 3.63(s, 3H); s, 72(s, 3H); 3.78(d, 1H); 4.15(dd, 1H); 4.35(m, 1H); 4.71(m, 1H); 5.00(dd, 1H); 6.52(s, 1H); 8.32(d, 1H); 8.56(d, 1H); 9.75(s, 1H) |
| 129 | OMe | COOMe | NHCO−CH=CH−(3,4-dihydroxyphenyl) | 1.94(s, 3H); 2.90(dd, 1H); 3.09(dd, 1H); 3.56(d, 1H); 3.62(s, 3H); 3.73(s, 3H); 3.82(d, 1H); 4.45(m, 1H); 4.79(m, 1H); 5.17(dd, 1H); 6.53(s, 1H); 6.64(d, 1H); 6.74(d, 1H); 6.88(dd, 1H); 6.97(d, 1H); 7.30(d, 1H); 8.35(d, 1H); 8.39(d, 1H); 9.15(s, 1H); 9.43(s, 1H); 9.75(s, 1H) |

EXAMPLE 130

A solution of 52 mg of methyl (4R, 7S)-7-amino-14-(tert-butyldimethylsilyloxy)-1,3,4,5,6,7,8,10-octahydro-12-methoxy-11-methyl-6,10-dioxo-9,2,5-benzoxathiaazacyclododecine-4-carboxylate and 100 mg of 4-nitrophenyl formate in 2 ml of methylene chloride was heated at reflux for 18 hours. The solution was evaporated in vacuo, and the residue was chromatographed on silica gel using ethyl acetate/hexane (2:1, v/v) as eluent. The (tert-butyldimethylsilylated)-product obtained was treated with ammonium fluoride in methanol in an analogous manner to the procedure described in Example 13 to yield, after crystallization from acetone/hexane, 20 mg of methyl (4R, 7S)-7-formylamino-1,3,4,5,6,7,8,10-octahydro-14-hydroxy-12-methoxy-11-methyl-6,10-dioxo-9,2,5-benzoxathiaazacyclododecine-4-carboxylate as a white solid.

¹H-NMR (250MHZ, DMSO-d₆): δ1.93(s,3H); 2.86(dd, 1H); 3.10(dd, 1H); 3.57(d, 1H); 3.63(S,3H); 3.72 (s,3H); 3.76(d, 1H); 4,12(dd, 1H); 4.44(m, 1H); 4.72(m, 1H); 5.12 (dd, 1H); 6.52(s, 1H); 8.14 (s, 1H); 8.40(d, 1H); 8.58(d, 1H); 9.74 (s, 1H) ppm

EXAMPLE 131

Methyl (4R, 7S)-7-amino-14-(tert-butyldimethylsilyloxy)-1,3,4,5,6,7,8,10-octahydro-12-methoxy-6,10-dioxo-9,2,5-benzoxathiaazacyciododecine-4-carboxylate was acylated with allylacetic acid in an analogues manner as described in Example 122 and the protection groups were subsequently cleaved off using the procedure described in Example 13 to yield methyl (4R,7S)-7-(pent-4-enoylamino)-1,3,4,5,6,7,8,10-octahydro-14-hydroxy-12-methoxy-6,10-dioxo-9,2,5-benzooxathiaazacyclododecine-4-carboxylate as a white solid.

¹H-NMR (250 MHz,CDCl₃): δ2.30–2.50 (m, 4H); 3.11 (dd, 1H); 3.21 (dd, 1H); 3.77 (s, 3H); 3.80 (s,3H); 3.94(d, 1H); 4.14 (d, 1H); 4.56(dd, 1H); 4.82–5.22(m, ~5H); 5.50–6.00 (m, ~2H); 6.63 (d, 1H); 6.79 (d, 1H); 6.91 (d, 1H); 7.17 (d, 1H) ppm The starting material used above was prepared as follows:

(a) tert-Butyl (4R, 7S)-14-(tert-butyldimethylsilyloxy)-1,3,4,5,6,7,8,10-octahydro-12-methoxy-4-methoxycarbonyl-6,10-dioxo-9,2,5-benzoxathiaazacyclododecine-7-carbamate was subjected in an analogous manner to the procedure described in Example 14 (a) to give methyl (4R, 7S)-7-amino-14-(tert-butyldimethylsilyloxy)-1,3,4,5,6,7,8,10-octahydro-12-methoxy-6,10-dioxo9,2,5-benzoxathiaazacyclododecine-4-carboxylate.

EXAMPLE 132

To a solution of 51 mg of the product of Example 119(a) in 0.7 ml of methylene chloride were added at 0° C. 14 mg of propionyl chloride, and of 18 mg 4-dimethylaminopyridine. The mixture was stirred at 0° C. for 1.5 hours, then diluted with ethyl acetate and washed successively with 3N hydrochloric acid, water, 5% sodium bicarbonate solution, and with brine. The organic layer was dried over sodium sulfate and evaporated in vacuo. The residue was chromatographed on silica gel using ethyl acetate/hexane (1:1, v/v) as eluent, and the (tert-butyldimethylsilylated)-product obtained was treated with ammonium fluoride in methanol in an analogous manner to the procedure described in Example 13 to yield, after crystallization from ethyl acetate/hexane, 10 mg of methyl (4R, 7S)-1,3,4,5,6,7,8,10-octahydro-14-hydroxy-12-methoxy-11-methyl-6,10-dioxo- 7-propionylamino-9,2,5-benzoxathiaazacyclododecine-4-carboxylate as a white solid.

¹H-NMR(250 MHz, DMSO-d₆): δ1.01 (t, 3H); 1.93 (s, 3H); 2.24 (q, 2H); 2.88 (dd, 1H); 3.08 (dd, 1H); 3.50 (d, 1H); 3.62 (s, 3H); 3.72 (s, 3H); 3.78 (d, 1H); 4.12 (dd, 1H); 4.64 (m, 1H); 5.03 (dd, 1H); 6.51 (s, 1H); 8.18 (d, 1H); 8.21 (d, 1H); 9.75 (s, 1H) ppm

EXAMPLES 133–141

Operating in an analogues manner as described in the previous example, the product of Example 14 (a) was acylated with 3,4,5-trimethoxy-benzoyl chloride and with methanesulfonyl chloride, the product of Example 112 (a) was acylated with 2,3-dioxosulfinyl-benzoyl chloride, the product of example 119(a) was acylated with pyridine-3-carboxylic acid chloride and with methyl chloroformate, the product of Example 131 (a) was acylated with oxalylic acid mono-methylester chloride and with pyridine-3-sulfonyl chloride, and methyl (4R, 7S)-14-(tert-butyldimethylsilyloxy)-1,3,4,5,6,7,8, 10-octahydro-12-methoxy-11-methyl-7-methylamino-6,10-dioxo-9,2,5-benzoxathiaazacyclododecine-4-carboxylate was acylated with acetyl chloride and with benzoyl chloride, to yield the following compounds:

| Example No | R¹ | R² | R⁷ | ¹H-NMR (250 MHz, DMSO-d₆) δ, inter alia, ppm |
|---|---|---|---|---|
| 133 | Me | OH | NHCO-C₆H₂(OMe)₃ (3,4,5-trimethoxybenzamido) | 1.92(s, 3H); 2.86(dd, 1H); 3.10 (dd, 1H); 3.60(s, 3H); 3.61(d, 1H); 3.70 (d, 1H); 3.71(s, 3H); 3.84(s, 6H); 4.38–4.53(m, 2H); 4.85–4.99(m, 2H); 6.46 (s, 1H); 7.21(s, 2H); 8.49(d, 1H); 8.57(d, 1H); 9.51(s, 1H); 9.54(s, 1H) |
| 134 | Me | OH | NHSO2Me | 1.99(s, 3H); 2.90(dd, 1H); 3.01(s, 1H); 3.10(dd, 1H); 3.49(d, 1H); 3.63(s, 3H); 3.70(d, 1H); 4.20–4.50(m, 2H); 4.93 (dd, 1H); 6.48(s, 1H); 7.86(d, 1H); 8.49 (d, 1H); 9.50(s, 1H); 9.52(s, 1H) |
| 135 | H | OH | NHCO-C₆H₃(OH)₂ (2,3-dihydroxybenzamido) | 2.91(dd, 1H); 3.07(dd, 1H); 3.61 (s, 3H); 3.92(d, 1H); 4.33(dd, 1H); 4.37 (d, 1H); 4.63(m, 1H); 4.83(m, 1H); 4.97 (dd, 1H); 6.47(d, 1H); 6.53(d, 1H); 6.75 (d, 1H); 6.80(dd, 1H); 7.30(dd, 1H); 8.47(d, 1H) |

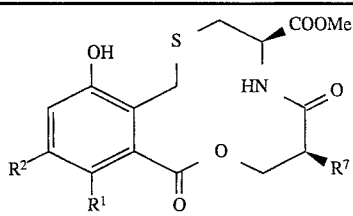

| Example No | R¹ | R² | R⁷ | ¹H-NMR (250 MHz, DMSO-d₆) δ, inter alia, ppm |
|---|---|---|---|---|
| 136 | Me | OMe | NHCO—(3-pyridyl) | 1.96(s, 3H); 2.82(dd, 1H); 3.08 (dd, 1H); 3.58(d, 1H); 3.60(s, 3H); 3.73 (s, 3H); 3.82(d, 1H); 4.37(dd, 1H); 4.52 (m, 1H); 4.88(m, 1H); 5.06(dd, 1H); 6.53 (s, 1H); 7.55(dd, 1H); 8.24(m, 1H); 8.47 (d, 1H); 8.75(dd, 1H); 8.88(d, 1H); 9.05 (d, 1H); 9.75(broad s, 1H) |
| 137 | Me | OMe | NHCOOMe | 1.92(3.3H), 2.83(dd, 1H); 3.07 (dd, 1H); 3.54(d, 1H); 3.60(s, 3H); 3.63 (s, 3H); 3.72(s, 3H); 3.79(d, 1H); 4.21 (dd, 1H); 4.37–4.54(m, 2H); 4.99 (dd, 1H); 6.51(s, 1H); 7.51(d, 1H); 8.33 (d, 1H); 9.71(s, 1H) |
| 138 | H | OMe | NHCOCOOMe | 2.85(dd, 1H); 3.12(dd, 1H); 3.64 (s, 3H); 3.72(s, 3H); 3.81(s, 1H); 3.88 (d, 1H); 4.23(d, 1H); 4.37(dd, 1H); 4.50–4.75(m, 2H); 4.86(dd, 1H); 6.62(d, 1H); 6.82(d, 1H); 8.65(d, 1H); 8.93(d, 1H):10.05(s, 1H) |
| 139 | H | OMe | NHSO₂—(3-pyridyl) | 2.86–3.16,(m, 2H); 3.63(s, 3H); 3.70 (s, 3H); 3.89(d, 1H); 4.16–4.33(m, 2H); 4.49–4.75(m, 2H); 6.60(d, 1H); 6.79 (d, 1H).; 7.73(m, 1H); 8.26(m, 1H); 8.63 (d, 1H); 8.84(m, 2H); 9.02(d, 1H); 10.07 (s, 1H) |
| 140 | Me | OMe | N(Me)COMe | 1.90(s, 3H); 2.08(s, 3H); 2.73(dd, 1H); 3.12(s, 3H); 3.18(dd, 1H); 3.64(s, 3H); 3.72(s, 3H); 4.24(dd, 1H); 4.40–4.74 (m, 2H); 5.39(m, 1H); 6.51(s, 1H); 8.29 (d, 1H); 9.71(s, 1H) |
| 141 | Me | OMe | N(Me)CO—Ph | 1.90(s, 3H); 2.76(m, 1H); 3.00–3.25 (m, 4H); 3.60–3.80(m, 5H) superimposed by 3.72(s, 3H); 4.18–4.70 (m, 3H); 5.46(m, 1H); 6.51(s, 1H); 7.42 (s, 5H); 9.70(s, 1H) |

EXAMPLE 142

A sample of 59 mg of the product of Example 119(a) was acylated with 60 mg of 3-trityloxypropionyl chloride in an analogues manner to the proceduree described in Example 132. To a suspension of the 14-(tert-butyldimethylsilylated)-product obtained in 2 ml of methanol were added 8 mg of p-toluenesulfonic acid mono-hydrate, and the mixture was stirred at 50° C. for 8 minutes. The solvent was evaporated, and the residue was chromatographed on silica gel using ethyl acetate as eluent. The 14-(tert-butyldimethylsilylated)-product obtained was treated with ammonium fluoride in methanol in an analogous manner to the procedure described in Example 13 to yield, after crystallization from methanol/diethylether, 10 mg of methyl (4R, 7S)-1,3,4,5,6,7,8,10-octahydro-14-hydroxy-7-(3-hydroxy-propionylamino)-12-methoxy-11-methyl-6,10-dioxo-9,2,5-benzoxathiaazacyclododecine-4-carboxylate as a white solid.

¹H-NMR (250 MHz, DMSO-d₆): δ1.93 (s, 3H); 2.30–2.50 (m, 4H); 2.82 (dd, 1H); 3.08 (dd, 1H); 3.52 (d, 1H); 3.60–3.78 (m, 2H) superimposed by 3.63 (s, 3H) and 3.72 (s, 3H); 3.80 (d, 1H); 4.10 (dd, 1H); 4.44 (m, 1H); 4.64 (m, 1H); 4.76 (t, 1H); 5.13(dd, 1H); 6.52(s, 1H); 8.23(d, 1H); 8.28(d, 1H); 9.75(s, 1H) ppm

EXAMPLE 143

The product of Example 14(a) was acylated with 2,2-diphenyl-1,3-benzodioxole-5-sulfonyl chloride in an analogues manner the procedure described in Example 132. The resulting product was stirred in 80% aqueous trifluoroacetic acid, and then the mixture was evaporated in vacuo. The residue was stirred with diethylether/hexane and the crystals formed were isolated by filtration to yield methyl (4R, 7S)-12, 14-dihydroxy-7-(3,4-dihydroxybenzenesulfonamido)-1,3,4,5,6,7,8,10-octahydro-11-methyl-6,10-dioxo-9, 2,5-benzoxathiaazacyclododecine-4-carboxylate.

¹H-NMR (250 MHz, DMSO-d₆): δ1.86 (s, 3H); 2.84 (dd, 1H); 3.03 (dd, 1H); 3.39 (d, 1H); 3.62 (s, 3H); 3.79(d, 1H); 3.81(m, 1H); 3.92(m, 1H); 4.42(m, 1H); 4.88(dd, 1H); 6.46 (s, 1H); 6.87 (d, 1H); 7.38 (dd, 1H); 7.43 (d, 1H); 8.39 (d, 1H); 8.44 (d, 1H); 9.50(s,1H); 9.52(s,1H); 9.63(s,1H); 9.94(s, 1H) ppm

EXAMPLE 144

A solution of 28 mg of the product of Example 131(a) and 5.2 mg of methylisothiocyanate in 2 ml of tetrahydrofuran is heated to 60° C. for 3 hours. The solvent was evaporated in vacuo and the residue was crystallized from diethylether/pentane to yield 25 mg of methyl (4R, 7S)-14-(tertbutyldimethylsilyloxy)-1,3,4,5,6,7,8,10-octahydro-12-methoxy7-(3-methyl-thioureido)-6,10-dioxo-9,2,5-benzoxathiaazacyclododecine-4-carboxylate.

A sample of 22 mg of this material was treated with ammonium fluoride in methanol in an analogous manner to the procedure described in Example 13 to yield, after crystallization from ethyl acetate/pentane, 15 mg of methyl (4R, 7S)-1,3,4,5,6,7,8,10-octahydro-14-hydroxy-12-methoxy-7-(3-methyl-thioureido)-6,10-dioxo-9,2,5-benzoxathiaazacyclododecine-4-carboxylate as a white solid.

¹H-NMR(250 MHz, DMSO-d₆): δ2.89(d, 3H); 2.99(dd, 1H); 3.11(dd, 1H); 3.63(s,3H); 3.71(s,3H); 3.92 (d, 1H); 4.18 (d, 1H); 4.25 (m, 1H); 4.41 (m, 1H); 5.00 (m, 1H); 5.23 (m, 1H); 6.58 (d, 1H); 6.75 (d, 1H); 7.75 (m, 1H); 7.88 (m, 1H); 8.62 (d, 1H); 10.06(s, 1H) ppm

EXAMPLES 145–149

By the reaction of the product of Example 131 (a) with benzoylisothiocyanate and with benzoyl-isocyanate in an analogous manner as described in the previous example, and by the reaction of the product of Example 112 (a) with 4-bromophenylisocyanate in refluxing acetonitrile, and with potassium cyanate in acetic acid at 20° C. with subsequent cleavage of the (tert-butyldimethylsilyl)-groups using the procedure described in Example 13, and by the reaction of the product of Example 110 with 4-chlorophenyl-isothiocyanate, the following compounds were obtained:

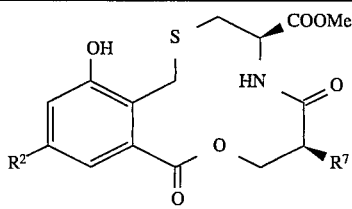

| Example No | R² | R⁷ | ¹H-NMR (250 MHz, DMSO-d₆) δ, inter alia, ppm |
|---|---|---|---|
| 145 | OMe | NHCSNHCO—⟨phenyl⟩ | 2.98(dd, 1H); 3.14(dd, 1H); 3.64 (s, 3H); 3.71(s, 3H); 3.96(d, 1H); 4.16 (d, 1H); 4.38–4.60(m, 2H); 5.19 (dd, 1H); 5.27(m, 1H); 6.60(d, 1H); 6.74 (d, 1H); 7.48(t, 2H); 7.63(t, 1H); 7.93 (d, 1H); 8.94(d, 1H); 10.11(s, 1H); 11.69(s, 1H) |
| 146 | OMe | NHCONHCO—⟨phenyl⟩ | 2.92(dd, 1H); 3.02(dd, 1H); 3.64 (s, 3H); 3.72(s, 3H); 3.93(d, 1H); 4.21 (d, 1H); 4.34(dd, 1H); 4.58(m, 1H); 4.74 (m, 1H); 5.13(dd, 1H); 6.60(d, 1H); 6.74 (d, 1H); 7.51(m, 2H); 7.63(m, 1H); 8.00 (m, 2H); 8.83(d, 1H); 9.50(d, 1H); 10.14 (s, 1H); 11.02(s, 1H) |
| 147 | OH | NHCONH—⟨phenyl⟩—Br | 2.96(dd, 1H); 3.14(dd, 1H); 3.63 (s, 3H); 3.92(d, 1H); 4.23(d, 1H); 4.50–4.64(m, 2H); 4.99(dd, 1H); 6.51 (d, 1H); 6.67(d, 1H); 6.79(d, 1H); 7.40 (m, 4H); 8.64(d, 1H); 9.00(s, 1H); 9.65 (s, 1H) 9.85(s, 1H) |
| 148 | OH | NHCONH2 | 2.95(dd, 1H); 3.09(dd, 1H); 3.64 (s, 1H); 3.89(d, 1H); 4.14(dd, 1H); 4.22 (d, 1H); 3.48(m, 1H); 3.53(m, 1H); 3.90 (dd, 1H); 5.87(s, 2H); 6.49(d, 1H); 6.56 (d, 1H); 6.67(d, 1H); 8.39(d, 1H); 9.63 (s, 1H); 9.83(s, 1H) |
| 149 | OH | NHCSNH—⟨phenyl⟩—Cl | 3.02(dd, 1H); 3.15(dd, 1H); 3.64 (s, 3H); 3.94(d, 1H); 4.21(d, 1H); 4.37 (dd, 1H); 4.44(m, 1H); 5.07(dd, 1H); 5.29 (m, 1H); 6.51(d, 1H); 6.66(d, 1H); 7.37 (d, 2H); 7.67(d, 2H); 8.16(d, 1H); 8.79 (d, 1H); 9.66(s, 1H); 9.86(s, 1H); 10.15 (s, 1H) |

EXAMPLE 150

To a solution of 184 mg of the product of Example 14 (a), 240 mg of acetone, and 49 mg of sodium acetate in 1 ml of 25% aqueous acetic acid, cooled to 0° C., were added portionwise within 1 hour 80 mg of sodium borohydride. The mixture was diluted with ethyl acetate and washed with saturated sodium carbonate solution and with brine. The organic layer was dried over sodium sulfate and evaporated in vacuo. The residue was chromatographed on silica gel using ethyl acetate/hexane (1:3, v/v) to give, after crystallization from diethylether/hexane, 54 mg 12,14-bis(tert-butyldimethylsilylated)-product. A sample of 34 mg of this material was treated with ammonium fluoride in methanol in an analogous manner to the procedure described in Example 13 to yield, after crystallization from methylene chloride/hexane, 15 mg of methyl (4R, 7S)-1,3,4,5,6,7,8,10-octahydro-12,14-dihydroxy-7-(isopropylamino)-11-methyl-6,10-dioxo-9,2,5-benzoxathiaazacyclododecine-4-carboxylate as a white solid.

$^1$H-NMR(250 MHz, DMSO-d$_6$): δ1.01(d, 3H); 1.04(d, 3H); 1.88(s,3H); 2.91(dd, 1H); 3.07(dd, 1H); 3.38 (d, 1H); 3.45 (m, 1H); 3.64 (s, 3H); 3.80 (d, 1H); 4.23 (dd, 1H); 4.55 (m, 1H); 4.88 (dd, 1H); 6.44(s, 1H); 8.49 (d, 1H); 9.48 (s, 1H); 9,50 (s, 1H) ppm

EXAMPLE 151

Operating in an analogues manner as described in the previous example, but replacing acetone by p-hydroxybenzaldehyde, there was obtained methyl (4R, 7S)-1,3,4,5,6,7,8,10-octahydro-12,14-dihydroxy-7-[(p-hydroxybenzyl)amino]-11-methyl-6,10-dioxo-9,2,5-benzoxathiaazacyclododecine-4-carboxylate as a white solid.

$^1$H-NMR (250 MHz, DMSO-d$_6$): δ1.87(s,3H); 2.88(dd, 1H); 3 .05 (dd, 1H); 3.38 (d, 1H); 3.55–3.77(m, 2H) superimposed by 3.68(s,3H); 3.84 (d, 1H); 4.24 (dd, 1H); 4.62(m, 1H); 4.90 (dd, 1H); 6.43(s, 1H); 6.70(d, 1H); 7.16(d, 1H); 8.42(d, 1H); 9.27 (s,1H); 9.45(s,2H) ppm

EXAMPLE 152

Operating in an analogues manner as described in Example 150, but replacing acetone by cyclopentanone, and using the product of Example 112 (a) as starting material, there was obtained methyl (4R, 7S)-7-(cyclopentylamino)-1,3,4,5,6,7,8,10-octahydro-12,14-dihydroxy-6,10-dioxo-9,2,5-benzoxathiaazacyclododecine-4-carboxylate.

$^1$H-NMR(250 MHz, DMSO-d$_6$): δ1.15–1.80 (m, ~9H); 1.88 (s, 3H); 2.87 (dd, 1H); 2.98–3.18 (m, 2H); 3.35–3.45 (m, 2H); 3.65 (s, 3H); 3.77 (d, 1H); 4.24 (dd, 1H); 4.54 (m, 1H); 4.85 (dd, 1H); 6.44 (s, 1H); 8.43 (d, H); 9.49 (s, 1H); 9.51 (s, 1H) ppm

EXAMPLE 153

To a solution of 61 mg of the product of Example 14(a) in 0.6 ml tetrahydrofuran/methanol (1:1, v/v), cooled to 0° C., were added 76 mg of sodium borohydride. The mixture was stirred for 1 hour at 0° C., then diluted with ethyl acetate, and washed with saturated sodium carbonate solution and with brine. The organic layer was dried over sodium sulfate and evaporated in vacuo. The residue was chromatographed on silica gel using ethyl acetate as eluent to give 22 mg of 12,14-bis(tert-butyldimethylsilylated)-product. This material was treated with ammonium fluoride in methanol in an analogous manner to the procedure described in Example 13 to yield, after crystallization from methylene chloride/ethyl acetate/hexane, 10 mg of (4R, 7S)-1,3,4,5,6,7,8,10-octahydro-12,14-dihydroxy-4-hydroxymethyl-7-(isopropylamino)-11-methyl-9,2,5-benzoxathiaazacyclododecine-6,10-dione as a white solid.

$^1$H-NMR (250 MHz, DMSO-d$_6$): δ(inter alia) 0.97 (d, 3H); 1 02 (d, 3H); 1.88(s,3H); 2.72–2.90 (m, 2H); 3.28–3.45 (m, 4H); 3.76 (d, 1H); 3.89 (m, 1H); 4.20 (dd, 1H); 4.82 (t,1H); 4.97(dd, 1H); 6.43(s, 1H); 7.81(d, 1H); 9.44(s, 1H); 9.47 (s, 1H) ppm

EXAMPLE 154

A solution of solution of 197 mg of tert-butyl (4R, 7S)-12,14-bis-(tert-butyldimethylsilyloxy)-1,3,4,5,6,7,8,10-octahydro-4-hydroxymethyl-11-methyl-6,10-dioxo-9,2,5-benzoxathiaazacyclododecine-7-carbamate, 78 mg of p-chlorobenzoyl chloride, and 60 mg of 4-dimethylaminopyridine was stirred at 20° C. for 3 hours. The mixture was diluted with ethyl acetate and washed successively with 3N hydrochloric acid, water, 5% sodium bicarbonate solution, and with brine. The organic layer was dried over sodium sulfate and evaporated in vacuo. The residue was dissolved in 2 ml of trifluoroacetic acid, and the solution was stirred at 0° C. for 30 minutes. The solvent was evaporated in vacuo, and the residue was treated with ammonium fluoride in methanol in an analogous manner to the procedure described in Example 13 to yield, after chromatographic purification on silica gel using ethyl acetate/hexane (1:1, v/v) as eluent, and crystallization from ethyl acetate/hexane, 28 mg of [(4R,7S)-7-amino-1,3,4,5,6,7,8,10-octahydro-12,14-dihydroxy-11-methyl-6,10-dioxo-9,2,5-benzoxathiaazacyclododecin-4-yl]methyl p-chlorobenzoate as a white solid.

$^1$H-NMR(250 MHz, DMSO-d$_6$): δ1.87(s,3H); 2.63(dd, 1H); 2.95(dd, 1H); 3.45(d, 1H); 3.61(m, 1H); 3.82 (d, 1H); 4.11(dd, 1H); 4.16–4.38(m,3H); 5.17(m, 1H); 6.44(s, 1H); 7.61 (d, 2H); 7.98 (d, 2H); 8.13 (d, 1H); 9.46 (s, 1H); 9.48 (s, 1H) ppm

EXAMPLE 155

Methyl (4R, 7S)-14-(tert-butyldimethylsilyloxy)-1,3,4,5,6,7,8,10-octahydro-12-methoxy-11-methyl-7-dimethylamino-6,10-dioxo-9,2,5-benzoxathiaazacyclododecine-4-carboxylate was treated with ammonium fluoride in methanol in an analogous manner to the procedure described in Example 13 to yield, after crystallization from ethyl acetate/hexane, 11 mg of methyl (4R, 7S)-1,3,4,5,6,7,8,10-octahydro-14-hydroxy-12-methoxy-11-methyl-7-dimethylamino-6,10-dioxo-9,2,5-benzoxathiaazacyclododecine-4-carboxylate as a white solid.

$^1$H-NMR(250 MHz, DMSO-d$_6$): δ1.92(s,3H); 2.31(s,6H); 2.83(dd, 1H); 3.06(dd, 1H); 3.43(d, 1H); 3.64 (s, 3H); 3.72 (s, 3H); 3.85 (d, 1H); 4.37 (dd, 1H); 4.55 (m, 1H); 4.82 (dd, 1H); 6.50 (s, 1H); 8.10 (d, 1H); 9.75 (s, 1H) ppm The starting material used above was prepared as follows:

(a) A solution of 100 mg of the product of Example 119(a) and 1.0 g of methyl iodide in 2 ml of acetonitrile was stirred at 20° C. for 3 hours. The solution was diluted with ethyl acetate and washed successively with saturated sodium bicarbonate solution and with brine. The organic layer was dried over sodium sulfate and evaporated in vacuo, and the residual oil was chromatographed on silica gel using ethyl acetate/hexane (2:1, v/v) as eluent to yield 17 mg of methyl (4R, 7S)-14-(tert-butyldimethylsilyloxy)-1,3,4,5,6,7,8,10-octahydro-12-methoxy-11-methyl-7-dimethylamino-6,10-dioxo-9,2,5-benzoxathiaazacyclododecine-4-carboxylate, and 23 mg of methyl (4R, 7S)-14-(tert-butyldimethylsilyloxy)-1,3,4,5,6,7,8,10-octahydro-12-methoxy-11-methyl-7-methylamino-6,10-dioxo-9,2,5-benzoxathiaazacyclododecine-4-carboxylate.

EXAMPLE 156

A solution of 45 mg of the product of Example 104 and 137 mg of bromoacetone in 0.9 ml of ethanol was heated to 80° C. for 2 hours. The solution was diluted with ethyl acetate, washed successively with 5% sodium bicarbonate solution and with brine, dried over sodium sulfate, and evaporated in vacuo. The residue was chromatographed on silica gel using ethyl acetate/hexane (1:2, v/v) as eluent, and the purified product was crystallized from ethyl acetate/hexane to give 6 mg of tertbutyl (4R, 7S)-1,3,4,5,6,7,8,10-octahydro-12,14-dihydroxy-11-methyl-4-(4-methyl-thiazol-2-yl)-6,10-dioxo-9,2,5-benzoxathiaaza-cyclododecine-7-carbamate as a white solid.

$^1$H-NMR(250 MHz,DMSO-d$_6$): δ1.42(s,9H); 1.90(s,3H); 2.33(s,3H); 2.92(dd, 1H); 3.26 (m,partially obcsured, 1H); 3.56(d, 1H); 3.92 (d, 1H); 4.25(dd, 1H); 4.37 (m, 1H); 4.97(dd, 1H); 5.25(m, 1H); 6.46(s, 1H); 7.17(d, 1H); 7.21 (s, 1H); 8.48 (d, 1H); 9.50 (s, 1H); 9.53 (s, 1H) ppm

EXAMPLE 157

A mixture of 85 mg of (4R,7S)-12,14-bis-(tert-butyldimethylsilyloxy)-4-carbazoyl-4,5,6,7,8-tetrahydro-7-hydroxy-11-methyl-9,2,5-benzoxathiaazacyclododecine-6,10-dione in 5 ml of ethyl acetate and 5 ml of 1N hydrochloric acid, cooled to 0° C., was treated with 25 mg of sodium nitrite, and then stirred for 15 minutes at 0° C. The phases were separated, and the organic phase was washed with brine, dried over sodium sulfate, and evaporated in vacuo. The residue was taken up in 1 ml of dimethylformamide, 25 mg of N-hydroxyacetamide were added, and the mixture was heated to 100° C. for 1.5 hours. The solvent was evaporated in vacuo and the residue was chromatographed on silica gel using ethyl acetate/hexane (1:1, v/v) as eluent. The 12,14-bis-(tert-butyldimethylsilylated)-product obtained was treated with ammonium fluoride in methanol in an analogous manner to the procedure described in Example 13 to yield 16 mg of (4R, 7S)-1,3,4,5,6,7,8,10-octahydro-7,12,14-trihydroxy-11-methyl-4-(3-methyl-1,2,4-oxadiazol-5-yl)-9,2,5-benzoxathiaazacyclododecine-6,10-dione as a white solid, m.p. 265°–267° C.

The starting material used above was prepared as follows:

(a) A solution of 170 mg of the 12,14-bis-(tert-butyldimethylsilylated)-product of Example 39 and 0.05 ml of hydrazine hydrate in 2 ml of methanol was heated at reflux for 45 minutes. The solution was evaporated in vacuo and the residue was crystallized from ethyl acetate to give 95 mg of (4R,7S)-12,14-bis-(tert-butyldimethylsilyloxy)-4-carbazoyl-4,5,6,7,8-tetrahydro-7-hydroxy-11-methyl-9,2,5-benzoxathiaazacyclododecine-6,10-dione as white needles of m.p. 242°–244° C.

EXAMPLE 158

A solution of 97 mg of the product of Example 2 and 0.2 ml of hydrazine hydrate in 1 ml of methanol was stirred at 20° C. for 45 minutes. The solution was diluted with ethyl acetate, and washed with 0.5M sodium dihydrogenphosphate solution and with water. The organic layer was dried over sodium sulfate and evaporated in vacuo, and the residue was crystallized from methanol/ethyl acetate/hexane to give 85 mg of tert-butyl (4R, 7S)-4-carbazoyl-1,3,4,5,6,7,8,10-octahydro-12,14-dihydroxy-11-methyl-6,10-dioxo-9,2,5-benzoxathiaazacyclododecine-7-carbamate as a white solid.

$^1$H-NMR(250 MHz, DMSO-d$_6$): δ1.42 (s, 9H); 1.89 (s, 3H); 2.63 (dd, 1H): 2.94 (dd, 1H); 3.44 (d, 1H); 3.86 (d, 1H); 4.15 (dd, 1H); 4.26 (broad s, 2H); 4.47 (m, 1H); 4.92 (dd, 1H); 6.44 (s, 1H); 7.46 (d, 1H); 7.95 (d, 1H); 9.10 (s, 1H); 9.48s, 1H) ppm

EXAMPLE 159

A solution of 37.5 mg of tert-butyl (4R, 7S)-14-(tert-butyldimethylsilyloxy)-1,3,4,5,6,7,8,10-octahydro-4-methoxycarbonyl-6,10-dioxo-12-(1,3-dioxo-1,3-dihydro-isoindol-2-yl)9,2,5-benzoxathiaazacyclododecine-7-carbamate and 5.8 mg of 3-dimethylaminopropylamine in 1.5 ml of methanol was stirred at 20° C. for 3 hours. Then, 30 mg of ammonium fluoride were added, and stirring was continued for another 2 hours. The solvent was evaporated in vacuo, and the residue was partitioned between ethyl acetate and brine. The organic layer was dried over sodium sulfate, the solvent was evaporated in vacuo, and the residue was chromatographed on silica gel, using methylene chloride/methanol (19: 1, v/v) as eluent, to yield, after crystallization from diethylether, 11 mg of tert-butyl (4R, 7S)-12-amino-14-hydroxy-1,3,4,5,6,7,8,10-octahydro-4-methoxycarbonyl-6,10-dioxo-9,2,5-benzoxathiaazacyclododecine-7-carbamate as a white solid.

$^1$H-NMR (250MHZ,DMSO-d$_6$): δ1.42(s,9H); 2.82(dd, J=14 Hz and 10 Hz,1H); 3.02(dd, J=14 Hz and 10 Hz, 1H); 3.64 (s, 3H); 3.80 (d, J=10 Hz, 1H); 4.12–4.42 (m, 3H); 4.54–4.78(m,2H); 5.25(broad s,2H); 6.26(d,J=2 Hz, 1H); 6.55(broad s, 1H); 7.36(d,J=8 Hz, 1H); 8.24(d,J=8 Hz, 1H); 9.39(s, 1H) ppm The starting material used above was prepared as follows:

(a) A mixture of 7.00 g of 3,5-dihydroxy-2-methylbenzoic acid, 5.40 g of ammonium chloride, and 20 ml of 25% aqueous ammonia was heated to 180° C. for 40 hours in a pressure vessel. After cooling, the mixture was evaporated in vacuo. The residue was taken up in 230 ml of 6N hydrochloric acid, and the mixture was heated at reflux for 16 hours. After cooling, unsoluble material was removed by filtration, and the filtrate was evaporated in vacuo. The residue was supended in 100 ml of water, the pH of the suspension was adjusted to 4.5 by the addition of 3N sodium hydroxide, and the mixture was cooled to 0° C. for 30 minutes. The precipitate was isolated by filtration and dried to give 2.50 g of 5-amino-3-hydroxy-2-methylbenzoic acid as white crystals, m.p. >250° C.

$^1$H-NMR(250 MHz,DMSO-d$_6$): δ2.11(s,3H); 6.24(d,J=2.5 Hz, 1H); 6.47(d, J=2.5 Hz, 1H); 9.08 (s, 1H) ppm (b) A mixture of 300 mg 5-amino-3-hydroxy-2-methylbenzoic acid and 265 mg of phtalic anhydride in 12 ml of dimethylformamide was heated to 110° C. for 2 hours, and subsequently to 150° C. for another 2 hours. The solvent was evaporated in vacuo and the residue was crystallized from ethanol/diethylether to give 310 mg of 5-(1,3-dioxo-1,3-dihydro-isoindol-2-yl)-3-hydroxy-2-methylbenzoic acid as white crystals, m.p. >250° C.

$^1$H-NMR (250 MHz,DMSO-d$_6$): δ2.36(S,3H); 7.07 (d,J=2.5 Hz, 1H); 7.29(d,J=2.5 Hz, 1H); 7.80–8.00(4H); 10.06(S, 1H) ppm (c) A mixture of 120 mg of 5-(1,3-dioxo-1,3-dihydro-isoindol-2-yl)-3-hydroxy-2-methylbenzoic acid, 87 mg of 4-nitrobenzyl bromide and 139 mg of potassium carbonate in 3 ml of dimethylformamide was stirred at 0° C. for 4 hours. The solvent was evaporated in vacuo, and the residue was triturated with a mixture of methylene chloride and saturated sodium bicarbonate solution. The unsoluble material was isolated by filtration to yield 190 mg of p-nitrobenzyl 5-(1,3-dioxo-1,3-dihydroisoindol-2-yl)-3-hydroxy-2-methylbenzoate, m.p. 210°–244° C.

$^1$H-NMR(250 MHz, DMSO-d$_6$): δ2.35(s,3H); 5.47(s,2H); 7.10(d,J=3 Hz, 1H); 7.32(d,J=3 Hz,1H); 7.72 (d, J=9 Hz, 2H); 7.9–8.0 (m, 4H); 8.25 (d, J=9 Hz, 2H) ppm (d) To a suspension of 1.0 g of p-nitrobenzyl 5-(1,3-dioxo-1,3-dihydro-isoindol-2-yl)-3-hydroxy-2-methylbenzoate in 30 ml of dimethylformamide were added 0.71 g of tert-butyldimethylchlorosilane and 0.48 g of triethylamine, and the mixture was stirred at 20° C. for 24 hours. The solvent was evaporated in vacuo, and the residue was partitioned between 2N hydrochloric acid and ethyl acetate. The organic layer was washed with brine, dried over sodium sulfate, and the solvent was evaporated in vacuo. The residual oil was chromatographed on silica gel using methylene chloride as eluent to yield 0.90 g of p-nitrobenzyl 3-(tert-butyldimethylsilyloxy)-5-(1,3-dioxo-1,3-dihydro-isoindol-2-yl)-2-methylbenzoate as white solid, m.p. 125°–127° C.

(e) p-Nitrobenzyl 3-(tert-butyldimethylsilyloxy)-5-(1,3-dioxo-1,3-dihydro-isoindol-2-yl)-2-methylbenzoate was subjected in an analogous manner to a sequence of procedures described in Examples 1 (d, f) and 13 (f), and the resulting product was subjected in an analogous manner to the cyclization procedure described in Example 21 to give tert-butyl (4R,7S)-14-(tertbutyldimethylsilyloxy)-1,3,4,5,6,7,8,10-octahydro-4-methoxycarbonyl-6,10-dioxo-12-(1,3-dioxo-1,3-dihydro-isoindol-2-yl)-9,2,5-benzoxathiaazacyclododecine-7-carbamate as a white solid.

EXAMPLE 160

A solution of 47 mg of the product of Example 159 and 27 mg of sodium borohydride in 5 ml of tetrahydrofuran was added within 10 minutes to a mixture of 0.08 ml of 6N sulfuric acid and 0.05 ml of 40% aqueous formaldehyde in 2 ml of tetrahydrofuran at 0° C. Stirring was continued for 4 hours at 0° C. The mixture was diluted with ethyl acetate, and then washed with 10% sodium carbonate solution and with brine. The organic layer was dried over sodium sulfate and evaporated in vacuo. The residue was crystallized from ethyl acetate/diethylether to give 25 mg of tert-butyl (4R, 7S)-1,3,4,5,6,7,8,10-octahydro-14-hydroxy-4-methoxycarbonyl-12-dioxo-9,2,5-benzoxathiaazacyclododecine-7-carbamate as a white solid.

$^1$H-NMR(250MHZ,DMSO-d$_6$): δ1.42 (s, 9H); 2.60–2.85 (m, 1H) superimposed by 2.85 (s, 6H); 3.04(dd, J=14 Hz and 4 Hz, 1H); 3.64(s,3H); 3.86(d,J=10 Hz, 1H); 4.12–4.93 (m, 3H); 4.14 (m, 1H); 4.80 (m 1H); 6.38 (d, J=1.5 Hz, 1H); 6.63(broad s;1H); 7.40(d,J=7 Hz, 1H); 8.28(d,J=5Hz,1H); 9.61 (s, 1H) ppm

EXAMPLE 161

A mixture of 25 mg of the product of Example 159 and 0.1 ml of pyridine in 1.5 ml of acetic anhydride was stirred at 20° C. for 3 hours. The precipitate was collected by filtration, washed with pentane, and dissolved in 1.5 ml of methanol. After the addition of 2.6 mg of potassium carbonate, the mixture was stirred for 1.5 hours at 20° C., and then evaporated in vacuo. Water was added to the residue, and the insoluble material was isolated by filtration, to yield 7 mg of tert-butyl (4R,7S)-12-acetylamino-1,3,4,5,6,7,8,10-octahydro-14-hydroxy-4-methoxycarbonyl-6,10-dioxo-9,2,5-benzoxathiaazacyclododecine-7-carbamate as a white solid.

$^1$H-NMR(250MHZ, DMSO-d$_6$): δ1.42 (s, 9H); 2.02 (S, 3H); 2.88 (dd, 1H); 3.07 (dd, 1H); 3.64 (S, 3H); 3.88 (d, 1H); 4.24 (d, 1H); 4.28–4.44 (m, 2H); 4.58–4.83 (m, 2H); 7.38 (d, 1H); 7.48 (d, 1H); 7.63 (d, 1H); 8.28 (1H); 10.00 (s, 1H); 10.03 (s, 1H) ppm

EXAMPLE 162

A solution of 66 mg of the product of Example 119 and 0.15 ml of pyridine in 1.5 ml of acetic anhydride was stirred at 20° C. for 3 hours. The solution was evaporated in vacuo, the residue was dissolved in ethyl acetate, and the solution was washed with 10% sodium carbonate solution and with brine. The organic layer was dried over sodium sulfate and evaporated in vacuo. The residue was crystallized from methanol/diethylether to give 33 mg of methyl (4R,7S)-7-acetylamino-14-acetoxy-1,3,4,5,6,7,8,10-octahydro-12-methoxy-11-methyl-6,10-dioxo-9,2,5-benzoxathiaazacyclododecine-4-carboxylate as a white solid.

$^1$H-NMR(250 MHz, DMSO-d$_6$): δ1.93 (s, 3H); 2.05 (s, 3H); 2.91 (dd, 1H); 3.15 (dd, 1H); 3.40 (d, 1H); 3.63 (s, 3H); 3.73 (d, 1H); 3.77 (s, 3H); 4.13 (dd, 1H); 4.43 (dd, 1H); 4.69 (m, 1H); 5.09(dd, 1H); 6.88(s, 1H); 8.29(d, 1H) ppm

EXAMPLE 163

A solution of 110 mg of crude tert-butyl (4R,7S)- and tert-butyl (4S, 7S)-12,14-bis-(tert-butyldimethylsilyloxy)-1,3,4,5,6,7,8,10-octahydro-4-formyl-11-methyl-6,10-dioxo-9,2,5-benzoxathiaazacyclododecine-7-carbamate and 73 mg of triphenylphosporanylidene-acetic acid tert-butylester in 1 ml of toluene was stirred at 20° C. for 45 minutes. The solvent was evaporated, and the residue was chromatographed on silica gel using ethyl acetate/hexane (1:1, v/v) as eluent. The major bis-(tert-butyldimethylsilylated)-product obtained was treated with ammonium fluoride in methanol in an analogous manner to the procedure described in Example 13 to yield, after crystallization from ethyl acetate/hexane, 17 mg of tert-butyl (E)-3-[(4R, 7S)- or tert-butyl (E)-3-[(4S, 7S)-7-tert-butoxycarbonylamino-12,14-dihydroxy-11-methyl-6,10-dioxo-1,3,4,5,6,7,8,10-octahydro-9,2,5-benzoxathiaazacyclododecin-4-yl]-acrylate as a white solid.

$^1$H-NMR(250 MHz, DMSO-d$_6$): δ1.41 (s, 9H); 1.42 (s, 9H); 1.87 (s, 3H); 2.30 (dd, 1H); 2.95 (dd, 1H); 3.66 (d, 1H); 3.75 (d, 1H); 4.34–4.57 (m, 3H); 4.62 (m, 1H); 5.99 (d, 1H); 6.43 (s, 1H); 6.73(dd, 1H); 7.24(d, 1H); 8.52(d, 1H); 9.47(s,1H); 9.50 (s, 1H) ppm (In addition, 6 mg of the 4S- or 4R-epimer were obtained). The starting material used above was prepared as follows:

(a) Using in an analogous manner the procedure described in Example 16(d), but replacing 3-trityloxy-1-propanol by the 12, 14-bis (tert-butyldimethylsilylated)-product of Example 58, there was obtained crude tert-butyl (4R, 7S)-12,14-bis-(tertbutyldimethylsilyloxy)-1,3,4,5,6,7,8,10-octahydro-4-formyl-11-methyl-6,10-dioxo-9,2,5-benzoxathiaazacyclododecine-7-carbamate as a mixture with its 4S-epimer.

EXAMPLE 164

To a solution of 156 mg of the product of Example 119(a) in 1 ml of dimethylformamide were added 593 mg 4-bromophenacyl bromide and 219 mg of 4-dimethylamino-pyridine, and the mixture was heated to 40° C. for 4 hours. The mixture was diluted with ethyl acetate and then washed with 1N hydrochloric acid and with brine. The organic layer was dried over sodium sulfate and evaporated in vacuo. The residue was chromatographed on silica gel using ethyl acetate/hexane (2:1, v/v) as eluent. The 14-(tert-butyldimethylsilylated)-Product obtained was treated with ammonium fluoride in methanol in an analogous manner to the procedure described in Example 13 to yield, after crystallization from ethyl acetate/hexane, 36 mg of methyl (4R, 7S)-7-[2-(4-bromo-phenyl)-2-oxo-ethylamino]-1,3,4,5,6,7,8,10-octahydro-14-hydroxy-12-methoxy-11-methyl-6,10-dioxo-9,2,5-benzoxathiaazacyclododecine-4-carboxylate as a white solid.

$^1$H-NMR (250 MHz, DMSO-$d_6$): δ1.91(s,3H); 2.85(dd, 1H); 3.09(dd, 1H); 3.48(d, 1H); 3.55(m, 1H); 3.63 (s, 3H); 3.73 (s, 3H); 3.83 (d, 1H); 4.17 (dd, 1H); 4.35 (dd, 1H); 4.40 (dd, 1H); 4.62 (m, 1H); 5.04 (dd, 1H); 6.51 (s, 1H); 7.74 (d, 2H); 7.87 (d, 2H); 8.43 (d, 1H); 9.73 (d, 1H) ppm

EXAMPLE 165

A solution of 103 mg of the product of Example 119(a) and 24 mg of succinic anhydride in 2 ml of acetonitrile were heated to 70° C. for 1 hour. The solution was cooled to 20° C., and 2 ml of methanol and 40 mg of ammonium fluoride were added. The mixture was stirred for 1 hour, then diluted with ethyl acetate and extracted with 5% sodium bicarbonate solution and with water. The pH of the combined aqueous layer was adjusted to 2 by the addition of 3N hydrochloric acid, and then extracted with ethyl acetate. The ethyl acetate extract was washed with brine, dried over sodium sulfate, and evaporated in vacuo. The residue was crystallized from acetone/hexane to yield 59 mg of methyl (4R, 7S)-7-(3-carboxy-propionylamino)-1,3,4,5,6,7,8,10-octahydro-14-hydroxy-12-methoxy-11-methyl-6,10-dioxo-9,2,5-benzoxathiaazacyclododecine-4-carboxylate as a white solid.

$^1$H-NMR(250 MHz,DMSO-$d_6$): δ1.93(s,3H); 2.30–2.55(m, partially obscured, 4H); 2 .86 (dd, 1H); 3.09 (dd, 1H); 3.52 (d, 1H); 3.62 (s, 3H); 3.72 (s, 3H); 3.78 (d, 1H); 4.10 (dd, 1H); 4.46 (m, 1H); 4.64 (m, 1H); 5.10 (dd, 1H); 6.52 (s, 1H); 8.20 (d, 1H); 8.35(d, 1H); 9.74(s,1H); 12.10(broad s, 1H) ppm

EXAMPLE 166

The product of Example 110 was acylated with N-(tert-butoxycarbonyl)-β-alanine in an analogues manner to the procedure described in Example 122. The resulting product was treated with trifluoroacetic acid at 0° C. for 30 minutes to yield, after evaporation of the solvent and trituration of the residue with diethylether, methyl (4R, 7S)-7-(3-aminopropionylamino)-1,3,4,5,6,7,8,10-octahydro-12,14-dihydroxy-6,10-dioxo- 9,2,5-benzoxathiaazacyclododecine-4-carboxylate trifluoroacetate as a white solid.

$^1$H-NMR(250 MHz,DMSO-$d_6$): δ2.50–3.20 (ca. 20H); 3.62 (s, 3H); 3.80–3.95 (m, 3H); 4.14 (m, 1H); 4.34 (dd, 1H); 4.54 (m, 1H); 4.65 (m, 1H); 4.87 (m, 1H); 6.52 (d, 1H); 6.72 (d, 1H); 7.78(broad s,2H); 8.49(m, 1H); 8.67(m,1H); 9.67(s,1H); 9.89 (s, 1H) ppm

EXAMPLE 167

A mixture of 31 mg of the product of Example 14 (a), 4.3 mg of pivalaldehyde, and 12 mg of magnesium sulfate in 3 ml of methylene chloride was stirred for 5 hours at 20° C. The mixture was diluted with methylene chloride, washed with water, and the organic layer was dried over sodium sulfate. The bis-(tert-butyldimethylsilylated)-product obtained was treated with ammonium fluoride in methanol in an analogous manner to the procedure described in Example 13 to yield, after crystallization from diethylether, 8 mg of methyl (E or Z) (4R, 7S)-7-(tert-butylmethyleneamino)-1,3,4,5,6,7,8,10-octahydro-12,14-dihydroxy-11-methyl-6,10-dioxo-9,2,5-benzoxathiaazacyclododecine-4-carboxylate trifluoroacetate as a white solid.

$^1$H-NMR(250 MHz,CDCl$_3$): δ1.16 (s, 9H); 2.01 (s, 3H); 2.77 (dd, 1H); 3.08 (dd, 1H); 3.71 (d, 1H); 3.77 (s, 3H); 4.02 (m, 1H); 4.38 (d, 1H); 4.56 (dd, 1H); 4.98 (dd, 1H); 5.15–5.25 (m, 2H); 6.43 (s, 1H); 7.16 (s, 1H); 7.81 (s, 1H); 8.11 (d, 1H) ppm

EXAMPLE 168

A solution of 74 mg of trimethyloxonium tetrafluoroborate in 0.5 ml of acetonitrile was stirred at 20° C. for 3 hours, and then added to a solution of 51 mg of the product of Example 119(a) in 0.1 ml of acetonitrile, and stirring was continued for 2 hours. The solution was diluted with ethyl acetate, washed successively with saturated sodium carbonate solution and with brine, dried over sodium sulfate, and evaporated in vacuo. The residue was chromatographed on silanised silica gel using ethyl acetate/hexane (2:1, v/v) as eluent. The (tert-butyldimethylsilylated)-product obtained was treated with ammonium fluoride in methanol in an analogous manner to the procedure described in Example 13 to yield, after chromatographic purification on MCI-Gel CHP20P using 0–70% aqueous acetonitrile as eluent and lyophilization of the product-containing fractions, 14 mg of (E)- or (Z)-(4R, 7S)-7(1-methylimino-ethylamino)-1,3,4,5,6,7,8,10-octahydro-14-hydroxy-12-methoxy-11-methyl-6,10-dioxo-9,2,5-benzoxathiaazacyclododecine-4-carboxylic acid methylester as a white solid.

$^1$H-NMR(250 MHz, DMSO-$d_6$): (inter alia) δ1.88(s,3H); 2.83(dd, 1H); 2.99(dd, 1H); 3.53(d, 1H); 3.65 (s, 3H); 3.71 (s, 3H); 4.25 (d, 1H); 4.38 (dd, 1H); 4.70 (m, 2H); 4.83 (dd, 1H); 6.52 (s, 1H); 8.43 (d, 1H) ppm Mass spectrum: m/z 454 (M+H)

EXAMPLE 169

To a solution of 90 mg of (4R,7S)-7-tert-butoxycarbonylamino-14-tert-butyldimethylsilyloxy-1,3,4,5,6,7,8,10-octahydro-12-methoxy-11-methyl-6,10-dioxo-9,2,5-benzoxathiaazacyclododecine-4-carboxylic acid in 1.5 ml of tetrahydrofuran were added 49 mg of dipyridyl-2,2-disulfide and 79 mg of triphenylphosphine. The solution was stirred at 0° C. for 1 hour, and then 0.15 ml of a 1M solution of ethylmagnesium bromide in tetrahydrofuran were added. The mixture was stirred at 0° C. for 30 minutes, and then 0.5 ml of water were added, and stirring was continued for 5 minutes. The mixture was diluted with ethyl acetate and washed successively with 1N hydrochloric acid and with brine. The organic phase was dried over sodium sulfate, evaporated in vacuo, and the residual oil was chromatographed on silica gel using acetone/hexane (1:4, v/v) as eluent. The (tert-butyldimethylsilylated)-product obtained was treated with ammonium fluoride in methanol in an analogous manner to the procedure described in Example 13 to yield 5 mg of tert-butyl (4R, 7S)-1,3,4,5,6,7,8,10-octahydro- 14-hydroxy-12-methoxy-11-methyl-4-propionyl-6,10-dioxo-9,2,5-benzoxathiaazacyclododecine-7-carbamate as pale yellow foam.

¹H-NMR(400 MHz,CDCl₃): (inter alia) δ1.06(t,3H); 1.45(s, 9H); 2.06(s,3H); 2.53(m, 2H); 2.90–3.20(m, 2H); 3.49(d, 1H); 3.77(s,3H); 3.93(d, 1H); 6.50(s, 1H) ppm Mass spectrum: m/z (inter alia) 519 (M+Na); 497 (M+H); 441 (M+H-C₄H₈)

The starting material used above was prepared as follows:

(a) A mixture of 0.48 g of the product of Example 51, 0.45 g of tert-butyldimethylchlorosilane, and 0.40 g of triethylamine in 2 ml of dimethylaminoformamide was heated with stirring to 40° C. for 2 hours. The mixture was partitioned between ethyl acetate/hexane (1:1, v/v) and ice-cold 5% aqueous sodium bicarbonate solution. The organic phase was washed with 10% sodium chloride solution, dried over sodium sulfate, and evaporated in vacuo. The residual oil was dissolved in 3 ml of methanol, and the solution was stirred at 40° C. for 2 hours. The solvent was evaporated in vacuo, and the residue was stirred for 1 hour with 10 ml of hexane at 0° C. to give 0.54 g of (4R, 7S)-7-(tert-butoxycarbonylamino)-14-(tert-butyldimethylsilyloxy)-1,3,4,5,6,7,8,10-octahydro-12-methoxy-11-methyl-6,10-dioxo-9,2,5-benzoxathiaazacyclododecine-4-carboxylic acid as white crystals.

EXAMPLE 170

To a solution of 130 mg of the 12,14-bis-(tert-butyldimethylsilylated)-product of Example 120 in 4 ml of methylene chloride, cooled 0° C., were added 63 mg of 55% 3-chloroperbenzoic acid. The solution was stirred at 0° C. for 30 minutes, then diluted with methylene chloride, washed successively with saturated sodium bicarbonate solution and with brine, dried over sodium sulfate, and evaporated in vacuo. The residual oil was chromatographed on silica gel using acetone/hexane (1:5, v/v) as eluent to afford two bis-(tert-butyldimethylsilylated)-products. The product eluated first was treated with ammonium fluoride in methanol in an analogous manner to the procedure described in Example 13 to yield 34 mg of methyl (2R, 4R, 7S)- or methyl (2S, 4R, 7S)-7-acetylamino-1,3,4,5,6,7,8,10-octahydro-12,14-dihydroxy-11-methyl-6,10-dioxo-9,2,5-benzoxathiaazacyclododecine-4-carboxylate 2-oxide as a white solid.

¹H-NMR(250 MHz, DMSO-d₆): δ1.90(s,3H); 1.94(s,3H); 3.01(dd, 1H); 3.64(s,3H); 3.77(dd, 1H); 3.85 (d, 1H); 4.01 (dd, 1H); 4.18 (d, 1H); 4.62 (m, 1H); 4.98 (m, 1H); 5.09 (dd, 1H); 6.52 (s, 1H); 8.26(d, 1H); 8.79(broad s, 1H); 9.63(s, 1H); 9.73 (s, 1H) ppm

EXAMPLE 171

To a solution of 48,5 mg of the product of Example 2 in 0.5 ml of methanol were added 10.5 mg of hydroxylamine hydrochloride and 0.5 ml of a 0.3N solution of potassium hydroxyde in methanol. The solution was stirred for 20 hours at 20° C., then diluted with ethyl acetate and washed with water. The organic layer was dried over sodium sulfate and evaporated in vacuo. The residue was chromatographed on silica gel using ethyl acetate as eluent to yield, after crystallization from ethyl acetate/hexane 12 mg of tert-butyl (4R, 7S)-1,3,4,5,6,7,8,10-octahydro-12,14-dihydroxy-4-hydroxycarbamoyl-11-methyl-6,10-dioxo-9,2,5-benzoxathiaazacyclododecine-7-carbamate as a white solid.

¹H-NMR(250 MHz, DMSO-d₆): δ1.42(S,9H); 1,89(S,3H); 2.65(dd, 1H); 2.91(dd, 1H); 3.45(d, 1H); 3.87 (d, 1H); 4.15 (dd, 1H); 4.31 (m, 1H); 4.42 (m, 1H); 4.92 (dd, 1H); 6.46 (s, 1H); 7.44 (d, 1H); 7.95 (d, 1H); 8.95 (broad s, 1H); 9.53 (s, 1H); 10.68 (broad s, 1H) ppm

EXAMPLE 172

To a solution of 90 mg of (R)-2-[[(R)-2-(2-amino-2-methoxycarbonyl-ethyl) thio]methyl]-3,5-bis(tert-butyldimethylsilyloxy)-6-methyl-benzoic acid in 3 ml of acetonitrile, cooled to 0° C., were added 38 mg of N-(dimethylaminopropyl)-N'-ethylcarbodiimide hydrochloride. The mixture was stirred at 0° C. for 1 hour, then diluted with 40 ml of ethyl acetate and washed with 1N hydrochloric acid and with brine. The organic layer was dried over sodium sulfate and evaporated in vacuo. The residue was chromatographed on silica gel using ethyl acetate/hexane (1:1, v/v) as eluent to yield 36 mg of methyl (4R, 8R)-12,14-bis (tert-butyldimethylsilyloxy)-1,3,4, 5,6,7,8,10-octahydro-12,14-dihydroxy-8,11-dimethyl-6,10-dioxo-9,2,5-benzoxathiaazacyclododecine-4-carboxylate. This material was treated with ammonium fluoride in methanol in an analogous manner to the procedure described in Example 21 to yield, after crystallization from ethyl acetate/hexane, methyl (4R, 8R)-1,3,4,5,6,7,8,10-octahydro-12,14-dihydroxy-8,11-dimethyl-6,10-dioxo-9,2,5-benzoxathiaazacyclododecine-4-carboxylate as a white solid.

¹H-NMR(250 MHz, DMSO-d₆): δ1.31 (d, 3H); 1.68 (s, 3H); 2.37–2.76 (m, 3H, partially obscured); 3.08 (dd, 1H); 3.32 (d, 1H); 3.33 (s, 3H); 3.96 (d, 1H); 4.68 (m, 1H); 5.67 (m, 1H); 6.41 (s, 1H); 8.41 (d, 1H); 9.45 (s, 1H); 9.48 (s, 1H) ppm The starting material used above was prepared as follows:

(a) To a suspension of 5.5 g of L-cysteine methyl ester hydrochloride in 80 ml of dioxane were added 3.6 g of 4-methylmorpholine and 7.0 g of di-tert-butyl-dicarbonate. After being stirred at 20° C. for 15 hours, the mixture was poured into ice-cold 0.2N hydrochorid acid, and the product was extracted with ethyl acetate. The organic layer was washed with brine, dried over sodium sulfate, and the solvent was evaporated in vacuo. The residual oil was chromatographed on silica gel using ethyl acetate/hexane (1:4, v/v) as eluent to yield 2.87 g of N-(tert-butoxycarbonyl-L-cysteine methyl ester as an oil.

(b) A solution of 5.0 g of p-Nitrobenzyl 2-bromomethyl-3-(tert-butyldimethylsilyloxy)-5-methoxybenzoate and 1.88 g of N-(tert-butoxycarbonyl-L-cysteine methyl ester in 40 ml of methylene chloride, cooled to 0° C., was treated with 0.81 of triethylamine. The mixture was stirred for 30 minutes at 0° C. and for 1 hour at room temperature, then diluted with ethyl acetate and washed with 0.5N hydrochloric acid and with brine. The organic layer was dried over sodium sulfate, and the solvent was evaporated in vacuo. The residual oil was chromatographed on silica gel using ethyl acetate/ methylene chloride/hexane (1:2:4, v/v/v) as eluent to yield 3.64 g of p-nitrobenzyl (R)-2-[[[(2-tert-butoxycarbonylamino-2-methoxycarbonyl)ethyl]thio]methyl] -3,5-bis (tert-butyldimethylsilyloxy)-6-methyl-benzoate as an oil.

(c) The product of the previous experiment was subjected in an analogous manner to the procedure described in Example 13 (f) to yield (R)-2-[[[(2-tert-butoxycarbonylamino-2-methoxycarbonyl)ethyl]thio]methyl]-3,5-bis (tert-butyldimethylsilyloxy)-6-methyl-benzoic acid.

(d) A solution of 1.05 g of the product of the previous experiment, 0.52 g of tert-butyl (S)-3-hydroxybutyrate, and 0.85 g of triphenylphosphine in 40 ml of toluene was cooled to 0° C. Then, 0.57 g of diethyl azodicarboxylate were added, and the mixture was stirred for 15 minutes at 0° C. and for 2 hours at room temperature. The solvent was evaporated in vacuo. The residue was stirred with diethylether/hexane 0° C. for 15 minutes, unsoluble material was filtered off, and the filtrate was evaporated in vacuo. The residue was chromatographed on silica gel using ethyl acetate/hexane (1:4, v/v) as eluent to give 0.92 g of (R)-2-[[[(2-tert-butoxycarbonylamino-2-methoxycarbonyl) ethyl]thio]methyl]-3,5-bis (tert-butyldimethylsilyloxy)-6-methyl-benzoic acid (R)-2-tert-butoxycarbonyl-1-methyl-ethyl ester as an oil.

(e) A solution of 0.79 g of the product of the previous experiment in 4 ml of trifluoroacetic acid was stirred at 20° C. for 30 minutes. The solution was evaporated in vacuo, and the residue was chromatographed on silica gel using ethyl acetate/hexane (1:2, v/v) as eluent, to give 0.32 g of (R)-2-[[(R)-2-(2-amino-2-methoxycarbonyl-ethyl) thio]methyl]-3,5-bis (tert-butyldimethylsilyloxy)-6-methyl-benzoic acid as an oil.

EXAMPLE A

Manufacture of Dry Ampoules for Intramuscular Administration

A lyophilisate of 1 g of t-butyl (4R,7S)-1,3,4,5,6,7,8,10-octahydro-12,14-dihydroxy-4-methoxycarbonyl-11-methyl-6,10-dioxo-9,2,5-benzoxathiaazabicyclododecine-7-carbamate is prepared in the usual manner and filled into an ampoule. Prior to the administration, the lyophilisate is treated with 2.5 ml of a 2% aqueous lidocaine hydrochloride solution.

EXAMPLE B

Interlocking gelatin capsules each containing the following ingredients are manufactured in the usual manner:

| | |
|---|---|
| t-butyl (4R,7S)-1,3,4,5,6,7,8,10-octahydro-12,14-dihydroxy-4-methoxycarbonyl-11-methyl-6,10-dioxo-9,2,5-benzoxathiaazacyclododecine-7-carbamate | 500 mg |
| Luviskol (water-soluble polyvinylpyrrolidone) | 20 mg |
| Mannitol | 20 mg |
| Talc | 15 mg |
| Magnesium stearate | 2 mg |
| | 557 mg |

We claim:
1. Process for the manufacture of N-[[(4R,7S)-1,3,4,5,6,7,8,10-octahydro-12,14-dihydroxy-7-[[(3R)-3-hydroxy-1-L-seryl-L-prolyl]amino]-11-methyl-6,10-dioxo-9,2,5-benzoxathiaazacyclododecin-4-yl]carbonyl]-L-alanine and of pharmaceutically acceptable salts thereof, which comprises cultivating a subculture of the microorganism Streptomyces sp. NR0484 FERM-BP-1982 under submerged, aerobic conditions in an aqueous carbohydrate solution containing nitrogenous nutrients and sodium choride, thereafter isolating the desired compound from the fermentation broth and, if desired. converting the product obtained into a pharmaceutically acceptable salt thereof.

2. A biologically pure culture of Streptomyces sp. NR0484 FERM-BP-1982.

* * * * *

UNITED STATES PATENT AND TRADEMARK OFFICE
CERTIFICATE OF CORRECTION

PATENT NO. : 5,486,466
DATED : January 23, 1996
INVENTOR(S) : Mikio Arisawa, et al.

It is certified that error appears in the above-indentified patent and that said Letters Patent is hereby corrected as shown below:

In claim 1, column 104, line 25, delete "choride" and insert therefor -- chloride --.

In claim 1, column 104, line 27, delete "desired." and insert therefor -- desired, --.

Signed and Sealed this

Thirtieth Day of April, 1996

Attest:

BRUCE LEHMAN

*Attesting Officer*     *Commissioner of Patents and Trademarks*